United States Patent [19]

Shah et al.

[11] Patent Number: 5,521,300

[45] Date of Patent: May 28, 1996

[54] OLIGONUCLEOTIDES COMPLEMENTARY TO MYCOBACTERIAL NUCLEIC ACIDS

[75] Inventors: Jyotsna S. Shah, Nashua, N.H.; Ray M. Nietupski, Millbury; Jing Liu, Framingham, both of Mass.

[73] Assignee: Norval B. Galloway

[21] Appl. No.: 744,282

[22] Filed: Aug. 13, 1991

[51] Int. Cl.⁶ ............................ C07H 21/02; C07H 21/04
[52] U.S. Cl. ............................ 536/24.32; 435/6
[58] Field of Search .................... 435/6; 536/2.7, 536/24.32, 27; 935/78

[56] References Cited

U.S. PATENT DOCUMENTS

| 4,358,535 | 11/1982 | Falkow et al. | 435/5 |
| 4,410,660 | 10/1983 | Straus | 525/54.1 |
| 4,489,158 | 12/1984 | Straus | 435/7 |
| 4,575,484 | 3/1986 | Straus | 435/7 |

FOREIGN PATENT DOCUMENTS

| 8803957 | 6/1988 | WIPO. |  |
| PCT/US87/ 03009 | 6/1988 | WIPO. |  |
| WO 90/08841 | 2/1990 | WIPO | C12Q 1/68 |

OTHER PUBLICATIONS

Regensburger, A., et al. Complete nucleotide sequence of a 23S ribosomal RNA gene from *Micrococcas luteus* Nucl. Acids Res. (19889) 16:2344.

GenBank Locus MLRN23S from Regensburger et al. compared with GenBank Locus ML5S23S from Liesacker et al. reference of record.

B. Böddinghaus et al. J. Clin. Microbiol. 28, 1751–1759 (1990).

D. A. Stahl and J. W. Urbance J. Bacteriol. 172, 116–124 (1990).

J. Neefs et al. Nucl. Acids Res. 18 (suppl.), 2237–2317 (1990).

W. Liesack et al. FEBS Lett. 281, 114–118 (1991).

Wallace and Miyada Methods in Enzymology 152, 432–442 (1987).

Zainuddin and Dale, *Journal of General Microbiology* 135:2347–2355 (1989).

Conville et al., *Diagn. Microbiol. Infect. Dis.* 12: 217–219 (1989).

Butcher et al., *Gut* 29:1222–1228 (1988).

Ellner et al., *Journal of Clinical Microbiology* 26:1349–1352 (1988).

Colombrita et al., *J. Med. Microbiol.* 32:271–273 (1990).

Stockman and Roberts, *Abst. Annu. Meet. Am. Soc. Microbiol.* 88:137 (1988).

Primary Examiner—Margaret Parr
Assistant Examiner—David Schreiber
Attorney, Agent, or Firm—Norval B. Galloway

[57] ABSTRACT

Disclosed are nucleic acid oligonucleotides which are substantially complementary to nucleic acids from Mycobacteria, and subgeneric classes thereof. More specifically, the oligonucleotides are complementary to ribosomal RNA (rRNA) and the DNA encoding rRNA (rDNA). Uses for such oligonucleotides include detection of Mycobacteria by hybridization and amplification of Mycobacterial nucleic acid by polymerase chain reaction.

6 Claims, No Drawings

SEQUENCE LISTING ( 1 ) GENERAL INFORMATION:

( i i i ) NUMBER OF SEQUENCES: 127

( 2 ) INFORMATION FOR SEQ ID NO:1:

( i ) SEQUENCE CHARACTERISTICS:
       ( A ) LENGTH: 55 base pairs
       ( B ) TYPE: nucleic acid
       ( C ) STRANDEDNESS: double
       ( D ) TOPOLOGY: linear ( i i ) MOLECULE TYPE: RNA (genomic)

( x i ) SEQUENCE DESCRIPTION: SEQ ID NO:1:

GUCUGGGAAA CUGCCUGAUG GAGGGGGAUA ACUACUGGAA ACGGUAGCUA AUACC   55

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

AGTTTCCCAG GCTTATCCCG AAGTGCAGGG CAG   33

( 2 ) INFORMATION FOR SEQ ID NO:3:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TAGACCCAGT TTCCCAGGCT TATCCCGGA   29

( 2 ) INFORMATION FOR SEQ ID NO:4:

( i ) SEQUENCE CHARACTERISTICS:
        ( A ) LENGTH: 56 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:4:

ACGUGGGUGA UCUGCCCUGC ACUUCGGGAU AAGCCUGGGA AACUGGGUCU AAUACC   56

( 2 ) INFORMATION FOR SEQ ID NO:5:

( i ) SEQUENCE CHARACTERISTICS:
        ( A ) LENGTH: 56 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:5:

ACGUGGGCAA UCUGCCCUGC ACUUCGGGAU AAGCCUGGGA AACUGGGUCU AAUACC   56

( 2 ) INFORMATION FOR SEQ ID NO:6:

( i ) SEQUENCE CHARACTERISTICS:
        ( A ) LENGTH: 56 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:6:

ACGUGGGCAA UCUGCCCUGC ACACCGGGAU AAGCCUGGGA AACUGGGUCU AAUACC      56

( 2 ) INFORMATION FOR SEQ ID NO:7:

( i ) SEQUENCE CHARACTERISTICS:
        ( A ) LENGTH: 56 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:7:

ACGUGGGUAA UCUGCCCUGC ACUUUGGGAU AAGCCUGGGA AACUGGGUCU AAUACC      56

( 2 ) INFORMATION FOR SEQ ID NO:8:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:8:

CGGGUUGUAA AGUACUUUCA GCGGGGAGGA AGGGAGUAAA GUUAAUACCU UUGCUCAUUG      60

ACGUUACCCG CAGAAGAAGC ACCGGCUAAC      90

( 2 ) INFORMATION FOR SEQ ID NO:9:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:9:

CAATCCGAGA GAACCCGGAC CTTCGTCGAT GGTGAAAG      38

( 2 ) INFORMATION FOR SEQ ID NO:10:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CTTCTCCACC TACCGTCAAT CCGAGAGAAC CCGGACCTTC GTCG      44

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

CTTCTCCACC TACCGTCAAT CCGAGAGAAC      30

( 2 ) INFORMATION FOR SEQ ID NO:12:

( i ) SEQUENCE CHARACTERISTICS:
        ( A ) LENGTH: 82 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:12:

```
CGGGUNGUAA  ACCUCUUUCA  CCAUCGACGA  AGGUCCGGGU  UCUCUCGGAU  UGACGGUAGG     60
UGGAGAAGAA  GCACCGGCCA  AC                                                 82
```

( 2 ) INFORMATION FOR SEQ ID NO:13:

( i ) SEQUENCE CHARACTERISTICS:
        ( A ) LENGTH: 82 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:13:

```
CGGGUNGUAA  ACCUCUUUCA  CCAUCGACGA  AGGUCCGGGU  UUUCUCGGAU  UGACGGUAGG     60
UGGAGAAGAA  GCACCGGCCA  AC                                                 82
```

( 2 ) INFORMATION FOR SEQ ID NO:14:

( i ) SEQUENCE CHARACTERISTICS:
        ( A ) LENGTH: 82 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:14:

```
CGGGUUGUAA  ACCUCUUUCA  CCAUCGACGA  AGGUCCGGGU  UCUCUCGGAU  UGACGGUAGG     60
UGGAGAAGAA  GCACCGGCCA  AC                                                 82
```

( 2 ) INFORMATION FOR SEQ ID NO:15:

( i ) SEQUENCE CHARACTERISTICS:
        ( A ) LENGTH: 70 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:15:

```
CGGGUNGUAA  ACCGUUUUCA  AUAGGGACGA  AGCGCAAGUG  ACGGUACCUA  UAGAAGAAGG     60
ACCGGCCAAC                                                                 70
```

( 2 ) INFORMATION FOR SEQ ID NO:16:

( i ) SEQUENCE CHARACTERISTICS:
        ( A ) LENGTH: 126 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:16:

GGGCGUAAAG CGCACGCAGG CGGUUUGUUA AGUCAGAUGU GAAAUCCCCG GGCUCAACCU        60

GGGAACUGCA UCUGAUACUG GCAGCUUGAG UCUCGUAGAG GGGGGUAGAA UUCCAGGUGU        120

AGCGGU                                                                  126

( 2 ) INFORMATION FOR SEQ ID NO:17:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

ATTTCACGAA CAACGCGACA AACCACCTAC GAG                                    33

( 2 ) INFORMATION FOR SEQ ID NO:18:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

CTCACAGTTA AGCCGTGAGA TTTCACGAAC AACGCGAC                                38

( 2 ) INFORMATION FOR SEQ ID NO:19:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

ATCGCCCGCA CGCTCACAGT TAAGCCGTGA GATTTC                                  36

( 2 ) INFORMATION FOR SEQ ID NO:20:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

CAGGAATTCC AGTCTCCCCT GCAGTACTCT AGT                                    33

( 2 ) INFORMATION FOR SEQ ID NO:21:

( i ) SEQUENCE CHARACTERISTICS:
        ( A ) LENGTH: 126 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:21:

GGGCGUAAAG AGCUCGUAGG UNGUUUGUCG CGUNGUUCGU GAAAUCUCAC GGCUUAACUG        60

UGAGCGUGCG GGCGAUNCGG GCAGACUAGA GUACUGCGGG GGAGGCUGGA AUUCCUGGUG    120

UAGCGG    126

( 2 ) INFORMATION FOR SEQ ID NO:22:

( i ) SEQUENCE CHARACTERISTICS:
        ( A ) LENGTH: 126 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:22:

GGGCGUAAAG AGCUCGUAGG UNGUUUGUCG CGUNNUUCGU GAAAUCUCAC GGCUUAAGUG    60

UGAGCGUGCG GGCGAUACGG GCAGACUAGA GUACUGCAGG GGAGACUGGA AUUCCUGGUG    120

UAGCGG    126

( 2 ) INFORMATION FOR SEQ ID NO:23:

( i ) SEQUENCE CHARACTERISTICS:
        ( A ) LENGTH: 126 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:23:

GGGCGUAAAG AGCUCGUAGG UGGUUUGUCG CGUUGUUCGU GAAAUCUCAC GGCUUAACUG    60

UGAGCGUGCG NGCGAUACGG GCAGACUAGA GUACUGCAGG GGAGACUGGA AUUCCUGGUG    120

UAGCGG    126

( 2 ) INFORMATION FOR SEQ ID NO:24:

( i ) SEQUENCE CHARACTERISTICS:
        ( A ) LENGTH: 126 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:24:

GGGCGUAAAG AGCUCGUAGG UNGUUUGUCG CGUNNUUCGU GAAAACUCAC AGCUUNACUG    60

UGGGCGUGCG GGCGAUACGG GCAGACUAGA GUACUGCNGG GGAGACUGGA AUUCCUGGUG    120

UAGCGG    126

( 2 ) INFORMATION FOR SEQ ID NO:25:

( i ) SEQUENCE CHARACTERISTICS:
        ( A ) LENGTH: 81 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:25:

UACCUGGUCU UGACAUCCAC GGAAGUUUUC AGAGAUGAGA AUGUGCCUUC GGGAACCGUG    60

AGACAGGUGC UGCAUGGCUG U    81

( 2 ) INFORMATION FOR SEQ ID NO:26:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

CTGCACACAG GCCACAAGGG AACGCCTATC TCT        33

( 2 ) INFORMATION FOR SEQ ID NO:27:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

GGCCACAAGG GAACGCCTAT CTCTAGACGC GTCCTGTGCA TAT        43

( 2 ) INFORMATION FOR SEQ ID NO:28:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

GCACCACCTG CACACAGGCC ACAAGGGAA        29

( 2 ) INFORMATION FOR SEQ ID NO:29:

( i ) SEQUENCE CHARACTERISTICS:
        ( A ) LENGTH: 80 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:29:

UACCUGGGUU UGACAUGCAC AGGUCGCGUC UAGAGAUAGG CGUUCCCUUG UGGCCUGUGU        60

GCAGGUGGUG CAUGGCUGUC        80

( 2 ) INFORMATION FOR SEQ ID NO:30:

( i ) SEQUENCE CHARACTERISTICS:
        ( A ) LENGTH: 81 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:30:

UACCUGGGUU UGACAUGCAC AGGACGCGUC UAGAGAGAGG CGUUCCCUUG UAGCCAUGUG        60

UGCAGGUGGU GCAUGGCUGU C        81

( 2 ) INFORMATION FOR SEQ ID NO:31:

( i ) SEQUENCE CHARACTERISTICS:
  ( A ) LENGTH: 80 base pairs
  ( B ) TYPE: nucleic acid
  ( C ) STRANDEDNESS: double
  ( D ) TOPOLOGY: linear ( i i ) MOLECULE TYPE: RNA (genomic)

( x i ) SEQUENCE DESCRIPTION: SEQ ID NO:31:

UACCUGGGUU UGACAUGCAC AGGACGCGUC UAGAGAUAGG CGUUCCCUUG UGGCCUGUGU        60

GCAGGUGGUG CAUGGCUGUC        80

( 2 ) INFORMATION FOR SEQ ID NO:32:

( i ) SEQUENCE CHARACTERISTICS:
    ( A ) LENGTH: 80 base pairs
    ( B ) TYPE: nucleic acid
    ( C ) STRANDEDNESS: double
    ( D ) TOPOLOGY: linear ( i i ) MOLECULE TYPE: RNA (genomic)

( x i ) SEQUENCE DESCRIPTION: SEQ ID NO:32:

UACCUGGGUU UGACAUGCAC AGGACGCCAG UAGAGAUAUU GGUUCCCUUG UNGCCUGUGU        60

GCAGGUGGUG CAUGGCUGUC        80

( 2 ) INFORMATION FOR SEQ ID NO:33:

( i ) SEQUENCE CHARACTERISTICS:
    ( A ) LENGTH: 68 base pairs
    ( B ) TYPE: nucleic acid
    ( C ) STRANDEDNESS: double
    ( D ) TOPOLOGY: linear ( i i ) MOLECULE TYPE: RNA (genomic)

( x i ) SEQUENCE DESCRIPTION: SEQ ID NO:33:

AACGAGCGCA ACCCUUAUCC UUUGUUGCCA GCGGUCCGGC CGGGAACUCA AAGGAGACUG        60

CCAGUGAU        68

( 2 ) INFORMATION FOR SEQ ID NO:34:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:34:

CGAGTCCCCA CCATTACGTG CTGGCAAC        28

( 2 ) INFORMATION FOR SEQ ID NO:35:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:35:

CGAGTCCCCG GCATTACCCG CTGGCAAC        28

( 2 ) INFORMATION FOR SEQ ID NO:36:

( i ) SEQUENCE CHARACTERISTICS:
        ( A ) LENGTH: 69 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:36:

```
CGAGCGCAAC  CCUUGUCUCA  UGUUGCCAGC  ACGUAAUGGU  GGGGACUCGU  GAGAGACUGC    60
CGGGGUUAA                                                                 69
```

( 2 ) INFORMATION FOR SEQ ID NO:37:

( i ) SEQUENCE CHARACTERISTICS:
        ( A ) LENGTH: 69 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:37:

```
CGAGCGCAAC  CCUUGUCUCA  UGUUGCCAGC  GGGUNAUGCC  GGGGACUCGU  NAGAGACUGC    60
CGGGGUCAA                                                                 69
```

( 2 ) INFORMATION FOR SEQ ID NO:38:

( i ) SEQUENCE CHARACTERISTICS:
        ( A ) LENGTH: 69 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:38:

```
CGAGCGCAAC  CCUUGUCUCA  UGUUGCCAGC  GGGUAAUGCC  GGGGACUCGU  GAGAGACUGC    60
CGGGGUCAA                                                                 69
```

( 2 ) INFORMATION FOR SEQ ID NO:39:

( i ) SEQUENCE CHARACTERISTICS:
        ( A ) LENGTH: 69 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:39:

```
CGAGCGCAAC  CCUUGUCUCA  UGUUGCCAGC  ACGUUAUGGU  GGGGACUCGU  GAGAGACUGC    60
CGGGGUCAA                                                                 69
```

( 2 ) INFORMATION FOR SEQ ID NO:40:

( i ) SEQUENCE CHARACTERISTICS:
        ( A ) LENGTH: 50 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:40:

```
    GGUUAAGCGA  CUAAGCUAC  ACGGUGGAUG  CCCUGGCAGU  CAGAGGCGAU                    50
```

( 2 ) INFORMATION FOR SEQ ID NO:41:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:41:

```
    CAACAAAAAC  CAAAGAATAT  TGCACAAAGA  ACACGCC                                  37
```

( 2 ) INFORMATION FOR SEQ ID NO:42:

( i ) SEQUENCE CHARACTERISTICS:
        ( A ) LENGTH: 64 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:42:

```
    CUGCCGGCUA  GCGGUGGCGU  GUUCUUUGUG  CAAUAUUCUU  UGGUUUUUGU  UGUGUUUGUA        60

AGUG                                                                         64
```

( 2 ) INFORMATION FOR SEQ ID NO:43:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

```
    CAAAAACCAA  AGAATAAAAT  TGCACAAAAG  AACACGC                                  37
```

( 2 ) INFORMATION FOR SEQ ID NO:44:

( i ) SEQUENCE CHARACTERISTICS:
        ( A ) LENGTH: 64 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:44:

```
    GCGUUGCUAC  GGGUAGCGUG  UUCUUUUGUG  CAAUUUUAUU  CUUUGGUUUU  UGUGUUUGUA        60

AGUG                                                                         64
```

( 2 ) INFORMATION FOR SEQ ID NO:45:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

```
    CAAAAACCAA  AAATGAGTTT  AAAAGAAATT  GCACATC                                  37
```

( 2 ) INFORMATION FOR SEQ ID NO:46:

( i ) SEQUENCE CHARACTERISTICS:
        ( A ) LENGTH: 62 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:46:

UGGUUUUGUG UGUUGAUGUG CAAUUUCUUU UAAACUCAUU UUUGGUUUUU GUGUUGUAAG    60

UG    62

( 2 ) INFORMATION FOR SEQ ID NO:47:

( i ) SEQUENCE CHARACTERISTICS:
        ( A ) LENGTH: 38 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:47:

AGCGGCGAGC GAACGGGGAG CAGCCCAGAG CCUGAAUC    38

( 2 ) INFORMATION FOR SEQ ID NO:48:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

GGTTACCCAT GCGTGCGGTT TAGCCTGTTC CGCGTTC    37

( 2 ) INFORMATION FOR SEQ ID NO:49:

( i ) SEQUENCE CHARACTERISTICS:
        ( A ) LENGTH: 58 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:49:

AGUGGCGAGC GAACSGAACA GGCUAAACCG CACGCAUGGG UAACCGGGUA GGGGUUGC    58

( 2 ) INFORMATION FOR SEQ ID NO:50:

( i ) SEQUENCE CHARACTERISTICS:
        ( A ) LENGTH: 60 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:50:

AGUGGCGAGC GAACGCGGAA CAGGCUAAAC CGCACGCAUG GGUAACCGGG UAGGGGUUGU    60

( 2 ) INFORMATION FOR SEQ ID NO:51:

( i ) SEQUENCE CHARACTERISTICS:
   ( A ) LENGTH: 37 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:51:

GGTTACCCAT GCGTGCGGTT TAGCCATGTT CCGGTTC  37

( 2 ) INFORMATION FOR SEQ ID NO:52:

( i ) SEQUENCE CHARACTERISTICS:
      ( A ) LENGTH: 60 base pairs
      ( B ) TYPE: nucleic acid
      ( C ) STRANDEDNESS: double
      ( D ) TOPOLOGY: linear ( i i ) MOLECULE TYPE: RNA (genomic)

( x i ) SEQUENCE DESCRIPTION: SEQ ID NO:52:

AGUGGCGAGC GAACCGGAAC AUGGCUAAAC CGCACGCAUG GGUAACCGGG UAGGGGUUGU  60

( 2 ) INFORMATION FOR SEQ ID NO:53:

( i ) SEQUENCE CHARACTERISTICS:
      ( A ) LENGTH: 37 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:53:

GGTATCACAT GCATACGGTT TAGCCATCCC TTCTTTC  37

( 2 ) INFORMATION FOR SEQ ID NO:54:

( i ) SEQUENCE CHARACTERISTICS:
      ( A ) LENGTH: 60 base pairs
      ( B ) TYPE: nucleic acid
      ( C ) STRANDEDNESS: double
      ( D ) TOPOLOGY: linear ( i i ) MOLECULE TYPE: RNA (genomic)

( x i ) SEQUENCE DESCRIPTION: SEQ ID NO:54:

AGUGGCGAGC GAAAGAAGGG AUGGCUAAAC CGUAUGCAUG UGAUACCGGG UAGGGGUUGU  60

( 2 ) INFORMATION FOR SEQ ID NO:55:

( i ) SEQUENCE CHARACTERISTICS:
      ( A ) LENGTH: 13 base pairs
      ( B ) TYPE: nucleic acid
      ( C ) STRANDEDNESS: double
      ( D ) TOPOLOGY: linear ( i i ) MOLECULE TYPE: RNA (genomic)

( x i ) SEQUENCE DESCRIPTION: SEQ ID NO:55:

AGUGUGUGUG UUA  13

( 2 ) INFORMATION FOR SEQ ID NO:56:

( i ) SEQUENCE CHARACTERISTICS:
      ( A ) LENGTH: 42 base pairs
      ( B ) TYPE: nucleic acid
      ( C ) STRANDEDNESS: single ( D ) TOPOLOGY: linear ( i i ) MOLECULE TYPE: DNA (genomic)

( x i ) SEQUENCE DESCRIPTION: SEQ ID NO:56:

CTGACTGCCT CTCAGCCGGG TAGCGCTGAG ACATATCCTC CC 42

( 2 ) INFORMATION FOR SEQ ID NO:57:

( i ) SEQUENCE CHARACTERISTICS:
        ( A ) LENGTH: 71 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:57:

UGUGUGCGGG GUUGUGGGAG GAUAUGUCUC AGCGCUACCG GCUGAGAGGC AGUCAGAAAG 60

GUCGUGGUU A 71

( 2 ) INFORMATION FOR SEQ ID NO:58:

( i ) SEQUENCE CHARACTERISTICS:
        ( A ) LENGTH: 70 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:58:

GUGUGCGGGG UUGUGGGAGA UAUGUCUCAG UGCUACCCGG CUGAGAGGCA GUCAGAAAGU 60

GUCGUGGUUA 70

( 2 ) INFORMATION FOR SEQ ID NO:59:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:59:

CTGACTGCCC CTCAGCCGGG TAGAGCTGAG ACGKATCGTA CCC 43

( 2 ) INFORMATION FOR SEQ ID NO:60:

( i ) SEQUENCE CHARACTERISTICS:
        ( A ) LENGTH: 72 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:60:

GUGUGCGGGG UUGUGGGAUC GAUMCGUCUC AGCUCUACCC GGCUGAGGGN CAGUCAGAAA 60

GUGUCGUGGU UA 72

( 2 ) INFORMATION FOR SEQ ID NO:61:

( i ) SEQUENCE CHARACTERISTICS:
        ( A ) LENGTH: 42 base pairs
        ( B ) TYPE: nucleic acid 5,521,300

89 90

-continued ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:61:

CTGACTACCC TCCAGCCAGG TAGAACTGGA AAAACAGGTC CC                                    42

( 2 ) INFORMATION FOR SEQ ID NO:62:

( i ) SEQUENCE CHARACTERISTICS:
                ( A ) LENGTH: 71 base pairs
                ( B ) TYPE: nucleic acid
                ( C ) STRANDEDNESS: double
                ( D ) TOPOLOGY: linear ( i i ) MOLECULE TYPE: RNA (genomic)

( x i ) SEQUENCE DESCRIPTION: SEQ ID NO:62:

GUGUGCGGGG UUGUGGGACC UGUUUUUCCA GUUCUACCUG GCUGGAGGGU AGUCAGAAAA          60

UGUCGUGGUU A                                                                      71

( 2 ) INFORMATION FOR SEQ ID NO:63:

( i ) SEQUENCE CHARACTERISTICS:
                ( A ) LENGTH: 54 base pairs
                ( B ) TYPE: nucleic acid
                ( C ) STRANDEDNESS: double
                ( D ) TOPOLOGY: linear ( i i ) MOLECULE TYPE: RNA (genomic)

( x i ) SEQUENCE DESCRIPTION: SEQ ID NO:63:

UACAAGCAGU GGGAGCACGC UUAGGCGUGU GACUGCGUAC CUUUUGUAUA AUGG               54

( 2 ) INFORMATION FOR SEQ ID NO:64:

( i ) SEQUENCE CHARACTERISTICS:
                ( A ) LENGTH: 39 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:64:

CCATCACCAC CCTCCTCCGG AGAGGAAAAG GAGGCTCTG                                         39

( 2 ) INFORMATION FOR SEQ ID NO:65:

( i ) SEQUENCE CHARACTERISTICS:
                ( A ) LENGTH: 68 base pairs
                ( B ) TYPE: nucleic acid
                ( C ) STRANDEDNESS: double
                ( D ) TOPOLOGY: linear ( i i ) MOLECULE TYPE: RNA (genomic)

( x i ) SEQUENCE DESCRIPTION: SEQ ID NO:65:

UACAAUCCGU CAGAGCCUCC UUUUCCUCUC CGGAGGAGGG UGGUGAUGGC GUGCCUUUUG          60

AAGAAUGA                                                                          68

( 2 ) INFORMATION FOR SEQ ID NO:66:

( i ) SEQUENCE CHARACTERISTICS:
                ( A ) LENGTH: 68 base pairs
                ( B ) TYPE: nucleic acid
                ( C ) STRANDEDNESS: double (D) TOPOLOGY: linear (i i) MOLECULE TYPE: RNA (genomic)

(x i) SEQUENCE DESCRIPTION: SEQ ID NO:66:

UACAAUCCGU CAGAGCCUCC UUUUCCUCUC CGGAGGAGGG UGGUGAUGGC GUGCCUUUUG    60

AAGAAUGA    68

(2) INFORMATION FOR SEQ ID NO:67:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (i i) MOLECULE TYPE: DNA (genomic)

(x i) SEQUENCE DESCRIPTION: SEQ ID NO:67:

GGCACGCCAT CACCCCACGA AAGGGCTCTG    30

(2) INFORMATION FOR SEQ ID NO:68:

(i) SEQUENCE CHARACTERISTICS:
    (A) LENGTH: 53 base pairs
    (B) TYPE: nucleic acid
    (C) STRANDEDNESS: double
    (D) TOPOLOGY: linear (i i) MOLECULE TYPE: RNA (genomic)

(x i) SEQUENCE DESCRIPTION: SEQ ID NO:68:

UACAAUCCGU CAGAGCCCUU UCGUGGGGUG AUGGCGUGCC UUUGAAGAA UGA    53

(2) INFORMATION FOR SEQ ID NO:69:

(i) SEQUENCE CHARACTERISTICS:
    (A) LENGTH: 37 base pairs
    (B) TYPE: nucleic acid
    (C) STRANDEDNESS: single
    (D) TOPOLOGY: linear (i i) MOLECULE TYPE: DNA (genomic)

(x i) SEQUENCE DESCRIPTION: SEQ ID NO:69:

GGCACGCCAT CACCCCACGA CAAAGTCGAA GGCTCTG    37

(2) INFORMATION FOR SEQ ID NO:70:

(i) SEQUENCE CHARACTERISTICS:
    (A) LENGTH: 60 base pairs
    (B) TYPE: nucleic acid
    (C) STRANDEDNESS: double
    (D) TOPOLOGY: linear (i i) MOLECULE TYPE: RNA (genomic)

(x i) SEQUENCE DESCRIPTION: SEQ ID NO:70:

UACAAUCCGU CAGAGCCUUC GACUUUGUCG UGGGGUGAUG GCGUGCCUUU UGAAGAAUGA    60

(2) INFORMATION FOR SEQ ID NO:71:

(i) SEQUENCE CHARACTERISTICS:
    (A) LENGTH: 56 base pairs
    (B) TYPE: nucleic acid
    (C) STRANDEDNESS: double
    (D) TOPOLOGY: linear (i i) MOLECULE TYPE: RNA (genomic)

( x i ) SEQUENCE DESCRIPTION: SEQ ID NO:71:

GGGAAACCGA GUCUUAACUG GGCGUUAAGU UGCAGGGUAU AGACCCGAAA CCCGGU    56

( 2 ) INFORMATION FOR SEQ ID NO:72:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:72:

GAACACGCCA CTATTCACAC GCGCGTATGC GTGTGGGTCG CCCTATTCAG    50

( 2 ) INFORMATION FOR SEQ ID NO:73:

( i ) SEQUENCE CHARACTERISTICS:
        ( A ) LENGTH: 79 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:73:

GCGAAAGCGA GUCUGAAUAG GGCGACCCAC ACGCAUACGC GCGUGUGAAU AGUGGCGUGU    60

UCUGGACCCG AAGCGGAGU    79

( 2 ) INFORMATION FOR SEQ ID NO:74:

( i ) SEQUENCE CHARACTERISTICS:
        ( A ) LENGTH: 78 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:74:

GCGAAAGCGA GUCUGAAUAG GGCGACCCAC ASCAUACGCG CGUGUGAAUA GUGGCGUGUU    60

CUGGACCCGA AGCGGAGU    78

( 2 ) INFORMATION FOR SEQ ID NO:75:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:75:

CCAGAACACC CACTACACAC GCTCGCGCGC GATACGCCCT ATTCAG    46

( 2 ) INFORMATION FOR SEQ ID NO:76:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:76:

GCGAAAGCGA GUCUGAAUAG GGCGUAUCGC GCGCGAGCGU GUGUAGUGGC GUGUUCUGGA  60

CCCGAAGCGG AGU  73

( 2 ) INFORMATION FOR SEQ ID NO:77:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:77:

CCAGAACACA CCACTACACC ACACACTACT GTGCGGATAC CCCTATTCAG  50

( 2 ) INFORMATION FOR SEQ ID NO:78:

( i ) SEQUENCE CHARACTERISTICS:
        ( A ) LENGTH: 76 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:78:

GCGAAAGCGA GUCUGAAUAG GGGUAUCCGC ACAGUAGUGU GUGGUGUAGU GGUGUGUUCU  60

GGACCCGAAG CGGAGU  76

( 2 ) INFORMATION FOR SEQ ID NO:79:

( i ) SEQUENCE CHARACTERISTICS:
        ( A ) LENGTH: 43 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:79:

CCAGAACACG CAACTACACC CCRAAGGGAT GCGCCCTATT CAG  43

( 2 ) INFORMATION FOR SEQ ID NO:80:

( i ) SEQUENCE CHARACTERISTICS:
        ( A ) LENGTH: 69 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:80:

GCGAAAGCGA GUCUGAAUAG GGCGCAUCCC UUNGGGGUGU AGUUGCNUGU UCUGGACCCG  60

AAGCGGAGU  69

( 2 ) INFORMATION FOR SEQ ID NO:81:

( i ) SEQUENCE CHARACTERISTICS:
        ( A ) LENGTH: 60 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:81:

GAAAGCUAUU UAGGUAGCGC CUCGUGAAUU CAUCUCCGGG GGUAGAGCAC UGUUUCGGCA    60

( 2 ) INFORMATION FOR SEQ ID NO:82:

( i ) SEQUENCE CHARACTERISTICS:
        ( A ) LENGTH: 61 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:82:

GAAAUGCAUU UAGGUGCAGC GUUGCGUGGU UCACCGCGGA GGUAGAGCUA CUGGAUGCCG    60
A    61

( 2 ) INFORMATION FOR SEQ ID NO:83:

( i ) SEQUENCE CHARACTERISTICS:
        ( A ) LENGTH: 61 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:83:

GAAAUGCAUU UAGGUGCAGC GUUGCGUGUU UCACCACGGA GGUAGAGCUA CUGGAUGCCG    60
A    61

( 2 ) INFORMATION FOR SEQ ID NO:84:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:84:

CTCTACCTCC AACAAGAAAC ATGTGACGCT GCACC    35

( 2 ) INFORMATION FOR SEQ ID NO:85:

( i ) SEQUENCE CHARACTERISTICS:
        ( A ) LENGTH: 61 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:85:

GAAAUGCAUU UAGGUGCAGC GUCACAUGUU UCUUGUUGGA GGUAGAGCUA CUGGAUGCCG    60
A    61

( 2 ) INFORMATION FOR SEQ ID NO:86:

( i ) SEQUENCE CHARACTERISTICS:
        ( A ) LENGTH: 51 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:86:

CAAACUGCGA AUACCGGAGA AUGUUAUCAC GGGAGACACA CGGCGGGUGC U    51

( 2 ) INFORMATION FOR SEQ ID NO:87:

( i ) SEQUENCE CHARACTERISTICS:
        ( A ) LENGTH: 50 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:87:

CAAACUCCGA AUGCCGUGGU GUAAAGCGUG GCAGUGAGAC GGCGGGGGAU    50

( 2 ) INFORMATION FOR SEQ ID NO:88:

( i ) SEQUENCE CHARACTERISTICS:
        ( A ) LENGTH: 50 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:88:

CAAACUCCGA AUGCCGUGGU GUAUAGCGUG GCAGUGAGAC GGCGGGGKAU    50

( 2 ) INFORMATION FOR SEQ ID NO:89:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:89:

CGTCTCACTG CCACACTCTT GGACTTGTCG GCATT    35

( 2 ) INFORMATION FOR SEQ ID NO:90:

( i ) SEQUENCE CHARACTERISTICS:
        ( A ) LENGTH: 53 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:90:

CAAACUCCGA AUGCCGACAA GUCCAAGAGU GUGGCAGUGA GACGGCGGGG GAU    53

( 2 ) INFORMATION FOR SEQ ID NO:91:

( i ) SEQUENCE CHARACTERISTICS:
        ( A ) LENGTH: 54 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:91:

AAGCUGCGGC AGCGACGCUU AUGCGUUGUU GGGUAGGGA GCGUUCUGUA AGCC    54

( 2 ) INFORMATION FOR SEQ ID NO:92:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:92:

```
CTACCCACAC  CCACCACAAG  GTGGATGTGC  CGCGG                          35
```

( 2 ) INFORMATION FOR SEQ ID NO:93:

( i ) SEQUENCE CHARACTERISTICS:
    ( A ) LENGTH: 55 base pairs
    ( B ) TYPE: nucleic acid
    ( C ) STRANDEDNESS: double
    ( D ) TOPOLOGY: linear ( i i ) MOLECULE TYPE: RNA (genomic)

( x i ) SEQUENCE DESCRIPTION: SEQ ID NO:93:

```
AAGCCGCGGC  ACAUCCACCU  UGUGGUGGGU  GUGGGUAGGG  GAGCGUCCCU  CAUUC    55
```

( 2 ) INFORMATION FOR SEQ ID NO:94:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:94:

```
GCTCCCCTAC  CCAACCTTGC  GGTTGTCGCG  G                              31
```

( 2 ) INFORMATION FOR SEQ ID NO:95:

( i ) SEQUENCE CHARACTERISTICS:
    ( A ) LENGTH: 45 base pairs
    ( B ) TYPE: nucleic acid
    ( C ) STRANDEDNESS: double
    ( D ) TOPOLOGY: linear ( i i ) MOLECULE TYPE: RNA (genomic)

( x i ) SEQUENCE DESCRIPTION: SEQ ID NO:95:

```
AAGCCGCGAC  AACCGCAAGG  UUGGGUAGGG  GAGCGUCCCU  CAUUC              45
```

( 2 ) INFORMATION FOR SEQ ID NO:96:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:96:

```
GCTCCCCTAC  CCAACGATAA  ATCGTTGCCG  CGG                            33
```

( 2 ) INFORMATION FOR SEQ ID NO:97:

( i ) SEQUENCE CHARACTERISTICS:

( A ) LENGTH: 47 base pairs
            ( B ) TYPE: nucleic acid
            ( C ) STRANDEDNESS: double
            ( D ) TOPOLOGY: linear ( i i ) MOLECULE TYPE: RNA (genomic)

( x i ) SEQUENCE DESCRIPTION: SEQ ID NO:97:

AAGCCGCGGC AACGAUUUAU CGUUGGGUAG GGGAGCGUCC UGCAUCC            47

( 2 ) INFORMATION FOR SEQ ID NO:98:

( i ) SEQUENCE CHARACTERISTICS:
            ( A ) LENGTH: 42 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:98:

GCTCCCCTAC CCACATCCAC CGTAAAGATG AATGTGCCGC GG            42

( 2 ) INFORMATION FOR SEQ ID NO:99:

( i ) SEQUENCE CHARACTERISTICS:
            ( A ) LENGTH: 56 base pairs
            ( B ) TYPE: nucleic acid
            ( C ) STRANDEDNESS: double
            ( D ) TOPOLOGY: linear ( i i ) MOLECULE TYPE: RNA (genomic)

( x i ) SEQUENCE DESCRIPTION: SEQ ID NO:99:

AAGCCGCGGC ACAUUCAUCU UUACGGUGGA UGUGGGUAGG GGAGCGUCCC CCAUUC            56

( 2 ) INFORMATION FOR SEQ ID NO:100:

( i ) SEQUENCE CHARACTERISTICS:
            ( A ) LENGTH: 58 base pairs
            ( B ) TYPE: nucleic acid
            ( C ) STRANDEDNESS: double
            ( D ) TOPOLOGY: linear ( i i ) MOLECULE TYPE: RNA (genomic)

( x i ) SEQUENCE DESCRIPTION: SEQ ID NO:100:

UUAAUUGAUG GGGUUAGCGC AAGCGAAGCU CUUGAUCGAA GCCCCGGUAA ACGGCGGC            58

( 2 ) INFORMATION FOR SEQ ID NO:101:

( i ) SEQUENCE CHARACTERISTICS:
            ( A ) LENGTH: 35 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:101:

GGGCTTAAAT TCTCCGCTTC ACCTTGCGGG TTAAC            35

( 2 ) INFORMATION FOR SEQ ID NO:102:

( i ) SEQUENCE CHARACTERISTICS:
            ( A ) LENGTH: 61 base pairs
            ( B ) TYPE: nucleic acid
            ( C ) STRANDEDNESS: double
            ( D ) TOPOLOGY: linear ( i i ) MOLECULE TYPE: RNA (genomic)

( x i ) SEQUENCE DESCRIPTION: SEQ ID NO:102:

UUAAGAGGAC CCGUUAACCC GCAAGGUGAA GCGGAGAAUU UAAGCCCAG UAAACGGCGG    60

U    61

( 2 ) INFORMATION FOR SEQ ID NO:103:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:103:

GGGCTTAAAT TCTCCGCTTC ACCCTTGCGG GTTAAC    36

( 2 ) INFORMATION FOR SEQ ID NO:104:

( i ) SEQUENCE CHARACTERISTICS:
        ( A ) LENGTH: 62 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:104:

GUUAAGAGGA CCCGUUAACC CGCAAGGGUG AAGCGGAGAA UUUAAGCCCC AGUAAACGGC    60

GG    62

( 2 ) INFORMATION FOR SEQ ID NO:105:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:105:

GGGCTTAAAT TCTCTGCTTC ACCCCGAAGG TTAAC    35

( 2 ) INFORMATION FOR SEQ ID NO:106:

( i ) SEQUENCE CHARACTERISTICS:
        ( A ) LENGTH: 61 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:106:

GUUAAGAGGA CCUGUUAACC UUCGGGGUGA AGCAGAGAAU UUAAGCCCCA GUAAACGGCG    60

G    61

( 2 ) INFORMATION FOR SEQ ID NO:107:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:107:

GGGCTTAAAC TTCCTGCTTC ACTTACGGGT TAAC 34

( 2 ) INFORMATION FOR SEQ ID NO:108:

( i ) SEQUENCE CHARACTERISTICS:
        ( A ) LENGTH: 60 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:108:

GUUAAGAGGA CCCGUUAACC CGUAAGUGAA GCAGGAAGUU UAAGCCCCAG UAAACGGCGG 60

( 2 ) INFORMATION FOR SEQ ID NO:109:

( i ) SEQUENCE CHARACTERISTICS:
        ( A ) LENGTH: 61 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:109:

GUAGGAUAGG UGGGAGGCUU UGAAGUGUGG ACGCCAGUCU GCAUGGAGCC GACCUUGAAA 60
U 61

( 2 ) INFORMATION FOR SEQ ID NO:110:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:110:

CTCCGCCCCA ACTGGCGTCG AGGTTTCACA GTCTC 35

( 2 ) INFORMATION FOR SEQ ID NO:111:

( i ) SEQUENCE CHARACTERISTICS:
        ( A ) LENGTH: 61 base pairs
        ( B ) TYPE: nucleic acid
        ( C ) STRANDEDNESS: double
        ( D ) TOPOLOGY: linear ( i i ) MOLECULE TYPE: RNA (genomic)

( x i ) SEQUENCE DESCRIPTION: SEQ ID NO:111:

GUAGGAUAGG UGGGAGACUG UGAAACCUCG ACGCCAGUUG GGGCGGAGUC GUUGUUGAAA 60
C 61

( 2 ) INFORMATION FOR SEQ ID NO:112:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear (  i  i  ) MOLECULE TYPE: DNA (genomic)

( x i ) SEQUENCE DESCRIPTION: SEQ ID NO:112:

CTCCACCCCA ACTGGCGTTG AGGTTTCACA GTCTC                                      35

( 2 ) INFORMATION FOR SEQ ID NO:113:

( i ) SEQUENCE CHARACTERISTICS:
                ( A ) LENGTH: 61 base pairs
                ( B ) TYPE: nucleic acid
                ( C ) STRANDEDNESS: double
                ( D ) TOPOLOGY: linear ( i i ) MOLECULE TYPE: RNA (genomic)

( x i ) SEQUENCE DESCRIPTION: SEQ ID NO:113:

GUAGGAUAGG UGGGAGACUG UGAAACCUCA ACGCCAGUUG GGGUGGAGUC GUUGUUGAAA            60

U                                                                           61

( 2 ) INFORMATION FOR SEQ ID NO:114:

( i ) SEQUENCE CHARACTERISTICS:
                ( A ) LENGTH: 35 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:114:

CTCCACAACC ACTGGCGTGG CTGCTTCACA GTCTC                                      35

( 2 ) INFORMATION FOR SEQ ID NO:115:

( i ) SEQUENCE CHARACTERISTICS:
                ( A ) LENGTH: 61 base pairs
                ( B ) TYPE: nucleic acid
                ( C ) STRANDEDNESS: double
                ( D ) TOPOLOGY: linear ( i i ) MOLECULE TYPE: RNA (genomic)

( x i ) SEQUENCE DESCRIPTION: SEQ ID NO:115:

GUAGGAUAGG UGGGAGACUG UGAAGCAGCC ACGCCAGUGG UUGUGGAGUC GUUGUUGAAA            60

U                                                                           61

( 2 ) INFORMATION FOR SEQ ID NO:116:

( i ) SEQUENCE CHARACTERISTICS:
                ( A ) LENGTH: 36 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:116:

CTCCACACAA ACTGGGCGTC TGTGCTTCAA AGTCTC                                     36

( 2 ) INFORMATION FOR SEQ ID NO:117:

( i ) SEQUENCE CHARACTERISTICS:
                ( A ) LENGTH: 62 base pairs
                ( B ) TYPE: nucleic acid
                ( C ) STRANDEDNESS: double
                ( D ) TOPOLOGY: linear ( i i ) MOLECULE TYPE: RNA (genomic)

(x i) SEQUENCE DESCRIPTION: SEQ ID NO:117:

GUAGGAUMGG YSGGAGACUU UGAAGCACAG ACGCCCAGUU UGUGUGGAGU CGUUGUUGAA     60

AU     62

(2) INFORMATION FOR SEQ ID NO:118:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:118:

AAGGAGGTGA TCCAGCC     17

(2) INFORMATION FOR SEQ ID NO:119:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:119:

AGAGTTTGAT CCTGGCTC     18

(2) INFORMATION FOR SEQ ID NO:120:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:120:

TGYACACACC GCCCGT     16

(2) INFORMATION FOR SEQ ID NO:121:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:121:

ATTGGCCTTT CACCCC     16

(2) INFORMATION FOR SEQ ID NO:122:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:122:

GAACTGAAAC ATCTWAGT                           18

(2) INFORMATION FOR SEQ ID NO:123:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:123:

TTAGCMTTTC ACCCC                              15

(2) INFORMATION FOR SEQ ID NO:124:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:124:

CTTAGATGCY TTCAGC                             16

(2) INFORMATION FOR SEQ ID NO:125:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:125:

TTGGCMTTTC ACCCC                              15

(2) INFORMATION FOR SEQ ID NO:126:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:126:

AGGGRAACAR CCCAGA                             16

(2) INFORMATION FOR SEQ ID NO:127:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:127:

CCGAATTCGT CGACAACCAG GCTTAGCTTC CGGGTTCGG    39

OLIGONUCLEOTIDES COMPLEMENTARY TO MYCOBACTERIAL NUCLEIC ACIDS

BACKGROUND OF THE INVENTION

Organisms of the genus Mycobacteria are responsible for infection of a variety of animals, including man. An important difference between Mycobacteria and other bacteria is that the former have a thick, lipid-rich envelope. This envelope gives the cells their distinctive characteristics, which include: hydrophobicity, resistance to chemical injury by acids, alkalis and many of the disinfectants used to kill other bacteria, resistance to attack by macrophages in which Mycobacteria are then able to multiply to cause disease, ability to survive long periods of starvation or aridity without dehydration and allergic and immunogenic properties.

The envelope thus provides a means to identify and classify the numerous species of Mycobacteria. Traditionally, there have been two primary diagnostic methods applicable to the detection of Mycobacteria. These are: (i) the direct observation of the etiological agent (e.g., by microscopic techniques) and (ii) its culture.

Direct observation is generally reliable for some Mycobacterial species, but requires expensive equipment and highly trained personnel. Culturing of Mycobacteria, although reliable, is time consuming and inconvenient. Depending on the species, specimens must be incubated from 2–8 weeks before visible colonies appear. A need exists for an improved method for the detection of Mycobacteria.

SUMMARY OF THE INVENTION

The subject invention relates to oligonucleotides which are complementary to members of the genus Mycobacteria. Such oligonucleotides are useful, for example, in hybridization based assays (e.g., detection assays) or amplification-based methodologies (e.g., polymerase chain reaction). These oligonucleotides are grouped, based on their hybridization characteristics under defined conditions, into one of four distinct categories which are described in detail below. The invention also relates to the identification of bacteria belonging to subgeneric groups of the genus Mycobacteria by hybridization assay.

Use of the oligonucleotides of this invention in an assay offers important advantages over currently employed microbiological methods for the detection of Mycobacteria in test samples (e.g., water or biological fluids). Important among these advantages is the fact that rRNAs constitute a relatively large percentage of total cellular mass as compared to that of most other potential cellular target molecules, such as genes (DNA) or mRNA transcripts.

Furthermore, the rRNAS (and the genes encoding them, referred to as rDNA) appear not to be subject to lateral transfer between contemporary organisms. Thus, the rRNA primary structure provides an organism-specific molecular target, rather than a gene-specific target, as would likely be the case, for example, of a plasmid-borne gene or product thereof which may be subject to lateral transmission between contemporary organisms.

Other advantages of the use of the subject oligonucleotides include:

a) increased sensitivity (i.e., the ability to detect fewer Mycobacteria in a given sample);

b) potentially significant reduction in assay cost due to the use of inexpensive reagents and reduced labor;

c) accurate identification of even biochemically unusual strains of Mycobacteria; and d) faster results because it is not necessary to isolate the target bacterium from the sample prior to testing.

DETAILED DESCRIPTION

The present invention relates to oligonucleotides, or homologues thereof, which are substantially complementary to ribosomal RNA (rRNA) and ribosomal DNA (rDNA) from members of the genus Mycobacteria and members of subgeneric classes. It also relates to a method of detecting Mycobacteria in a sample thought to contain the organism. The oligonucleotides of the present invention can be ribose containing oligonucleotides (RNA) or deoxyribose containing oligonucleotides (DNA). In RNA, the nitrogenous base uracil is substituted for thymine, which is a DNA component. A homologue of an oligonucleotide is an oligonucleotide which has a nucleotide monomer sequence substantially similar to that of the oligonucleotide and, as a result, hybridizes to the same Mycobacterial nucleic acid sequence recognized (hybridized to) by the oligonucleotide under similar hybridization conditions. The sequences of two homologous oligonucleotides need not be the same and, for example, can differ with respect to nucleotide monomer number and the presence of modified nucleotides or nucleotide analogues.

Oligonucleotides of the present invention are substantially complementary to the rRNA (and to the DNA which encodes the rRNA) of the Mycobacterial genus. In particular, the oligonucleotides of this invention are substantially complementary to the 16S or 23S rRNAs, to which they hybridize under the appropriate conditions. In preferred embodiments, the oligonucleotides of this invention are deoxyribonucleotides. Substantially complementary oligonucleotides are oligonucleotides which are sufficiently complementary to hybridize in a stable manner to a rRNA (and rDNA) of Mycobacteria under defined conditions. As used herein, the term members of the genus Mycobacteria refers to bacteria classified as such in Bergey's Manual of Systematic Bacteriology (Volume 2 (1986), pp. 1435–1457, Sneath et al. editors, Williams and Wilkins, Baltimore, Md.). The genus includes a group of intracellular bacterial parasites ranging from the obligate intracellular pathogen *Mycobacterium leprae* and the facultative intracellular parasites *Mycobacterium tuberculosis, Mycobacterium bovis* and *Mycobacterium avium* to such environmental species as *Mycobacterium smegmatis* which seldom cause disease. Between these two extremes lies a large number of opportunistic pathogens including *Mycobacterium intracellulare* and *Mycobacterium scrofulaceum*.

The oligonucleotides of the invention can be used, for example, to detect members of the Mycobacterial genus in a sample by hybridization. The sample is treated to render nucleic acids present available for hybridization. In one embodiment, one or more oligonucleotides of this invention are then contacted with the treated sample under conditions appropriate for hybridization of substantially complementary nucleic acid sequences. If a Mycobacterial nucleic acid detectable by the oligonucleotide(s) is present, hybridization occurs. Hybridization is detected by any appropriate method. Such methods are well known to those skilled in the art.

In a second embodiment, Mycobacterial oligonucleotides are first amplified through use of the oligonucleotides of this invention in an amplification based technique, such as the polymerase chain reaction (PCR). In this technique, oligonucleotides complementary to antiparallel strands of rDNA are used to prime DNA synthesis by a DNA directed DNA polymerase, to amplify Mycobacterial sequences present in the sample. The amplified sequences are detected by conventional methods.

As described in detail below, the oligonucleotides of this invention are classified into 4 categories based on the hybridization results observed when the oligonucleotides were contacted with a panel of Mycobacteria, and a panel of bacteria which are not Mycobacteria. The members of the latter group were selected by identifying bacteria which are closely related to Mycobacteria and which might be found in a mixture of bacteria containing Mycobacteria.

Oligonucleotide Definitions

The four categories of oligonucleotides are: 1) substantially inclusive oligonucleotides; 2) partially inclusive oligonucleotides; 3) substantially inclusive non-exclusive oligonucleotides and 4) partially inclusive non-exclusive oligonucleotides. The four categories, as used herein, are defined in the following paragraphs. The categorization is based on the hybridization conditions described in Example 2. One skilled in the art will recognize that if the hybridization conditions described in Example 2 are varied within defined limits, some of the oligonucleotides described herein may fall within one of the three categories which differs from the category in which it falls under the conditions described.

Substantially inclusive oligonucleotides are defined as oligonucleotides which hybridize, under the assay conditions used, to rRNA (and rDNA) from substantially all (i.e., about 90% or more) of the Mycobacterial species listed in Table 3, but which do not hybridize to the rRNA of bacterial species listed in Table 4.

Partially inclusive oligonucleotides are defined as oligonucleotides which hybridize, under the assay conditions used, to rRNA (and rDNA) from a subset of the Mycobacterial species listed in Table 3, but which do not hybridize to the species listed in Table 4.

Substantially inclusive, non-exclusive oligonucleotides are oligonucleotides which hybridize, under the assay conditions used, to rRNA from substantially all of the Mycobacterial species listed in Table 3, and also to rRNA of at least about 10% of the other bacteria listed in Table 4. Partially inclusive, non-exclusive oligonucleotides are oligonucleotides which hybridize, under the assay conditions used, to rRNA from a subset of the Mycobacterial species listed in Table 3, and also to rRNA of at least about 10% of the other bacteria listed in Table 4. These two categories are referred to as non-exclusive because they hybridize not only to Mycobacteria, but also to about 10% of the other bacteria listed in Table 4. Thus, exclusivity refers to the ability of a particular oligonucleotide to discriminate between Mycobacterial nucleic acids and the nucleic acids of non-Mycobacteria (e.g. those listed in Table 4).

As discussed in detail below, the subject invention also relates to the identification of subgeneric classes of Mycobacteria. Thus, oligonucleotides which are partially inclusive for the Mycobacterial genus may, for example, be substantially inclusive for the subgeneric class. The subgeneric classes include, for example, the *Mycobacterium tuberculosis* complex and the slow growing class of Mycobacteria.

In some cases an oligonucleotide may show weak, or barely detectable, hybridization to a limited number of species in Table 4. For purposes of categorization, oligonucleotides which at a maximum hybridize weakly to less than 5% of the bacteria listed in Table 4 are considered to be oligonucleotides which do not hybridize to the species listed in the table. Oligonucleotides which at a minimum hybridize strongly to less than 5% of the bacteria listed in Table 4 are considered to be oligonucleotides which do hybridize to the species listed in the table. Strong hybridization, as used herein refers to +++ or ++++ as represented in Tables 3 or 4. Weak hybridization refers to + or ++ as represented in Tables 3 or 4. More specifically, as discussed in Example 2, ++++ designated a hybridization signal equivalent to that of control Mycobacterial DNA for which a perfect match between probe and target sequences was determined by sequence analysis, and + designates a signal which is barely detectable even after long exposure to x-ray film. The designator ND in Table 3 is not considered as a positive or negative indicator for purposes of categorization.

To provide a frame of reference which defines the relative location of the oligonucleotides of this invention, the corresponding nucleotide sequence numbers for the *E. coli* region, as determined by a database sequence comparison, are provided in Table 1. The *E. coli* nucleotides rRNA sequences have been determined and each nucleotide has been assigned an integer value for reference purposes. Table 1 shows the oligonucleotides of the invention aligned with the corresponding *E. coli* sequences. Dashes in Table 1 indicate that *E. coli* does not share sequences which are substantially complementary within the corresponding region shown. The oligonucleotides of this invention are complementary to either the 16S rRNA or the 23S rRNA of Mycobacteria.

Hybridization and Amplification-Based Assays

The oligonucleotides of this invention are useful in any of the known hybridization assays which rely on the formation and detection of hybrids between two or more complementary nucleic acid sequences, such as between a rRNA target nucleic acid (the presence of which in a sample is to be determined) and one or more sufficiently complementary nucleic acid sequences. Such hybridization assays include, for example, solution hybridization assays in which the complementary sequences are free in solution, or assays in which one of the complementary nucleic acid sequences is fixed to a solid support.

The latter group of assays includes dot blot analysis which involves immobilizing a nucleic acid or a population of nucleic acids on a solid support such as nitrocellulose, nylon, or other derivatized membranes, many of which are available commercially. Either DNA or RNA can be immobilized on such a solid support and subsequently can be probed or tested for hybridization under any of a variety of conditions with the oligonucleotides of the present invention.

Another type of assay in which a nucleic acid is fixed to a solid support is the dual probe, sandwich-type hybridization assay format (for example the homopolymer capture, dual probe liquid hybridization format described in U.S. Pat. No. 5,147,778 and U.S. Ser. No. 07/169,646, abandoned, the techniques of which are incorporated herein by reference). Such assays involve the use of a capture oligonucleotide and a detection oligonucleotide for the identification of a target nucleic acid sequence of interest. The capture oligonucleotide, which is substantially complementary to a target nucleic acid sequence, is generally derivatized by adding a member of a specific binding pair to facilitate subsequent isolation. Many useful examples of specific binding pairs are known in the art. A particularly convenient specific binding pair for use in connection with this assay is deoxyadenosine (dA)/deoxythymidine (dT). For example, a capture oligonucleotide can be derivitized by adding a polymeric sequence of dA residues at its 3' terminus. The capture oligonucleotide is then incubated with a solution to be tested for the target nucleic acid, under conditions appropriate for hybridization of sufficiently complementary nucleic acid sequences. If target nucleic acid sequences are present in the sample, hybridization occurs and a capture oligonucleotide-target nucleic acid complex is formed. The capture oligonucleotide-target nucleic acid complexes are isolated from the mixture by means of the derivatized capture oligonucleotide. For example, if the capture oligonucleotide has been derivatized by the addition of a polymeric sequence of dA residues, the mixture containing the capture oligonucleotide-target nucleic acid complex is brought into contact with a solid support which has been derivatized to include a dT polymeric sequence which will hybridize with the dA polymeric sequence. Many types of solid supports which can be derivatized as described are well known to those skilled in the art.

In a preferred embodiment, the solid support is a plastic plate having wells. The mixture containing the capture oligonucleotide-target nucleic acid complexes is placed in the derivatized well of the plastic plate for a period of time sufficient for the dA and dT polymeric sequences to hybridize. The mixture is then removed from the well and the wells are washed to remove any non-specifically bound components. The capture oligonucleotide-target nucleic acid completes will be retained in the wells of the plate while other components of the mixture will not be retained. A detection oligonucleotide is then introduced into the wells of the plate under conditions appropriate for hybridization. The detection oligonucleotide is complementary to the target nucleic acid in a region distinct from the region of complementarity between the capture oligonucleotide and the target nucleic acid. Hybridization is then detected by an appropriate means, many of which are well known in the art.

In preferred embodiments, the detection oligonucleotide is labeled with a detectable reporter group (such as a radioisotope) or a member of a specific binding pair (e.g., biotin/avidin). Alternatively, a replicatable RNA sequence can be attached to the detection oligonucleotide which can be autocatalytically replicated to generate a detectable signal (see, e.g., U.S. Pat. No. 4,786,600).

Oligonucleotide Use

Substantially inclusive oligonucleotides, which are defined above, are useful, for example, for the identification of members of the genus Mycobacteria in any hybridization assay which relies on the formation and detection of a hybrid between two or more substantially complementary nucleic acid sequences: e.g. a rRNA target nucleic acid (the presence of which in a sample is to be determined) and one or more detectable nucleic acid sequences. Such oligonucleotides hybridize to rRNA (and rDNA) from substantially all of the Mycobacterial species tested. In addition, they do not hybridize to nucleic acids from other types of bacteria (non-Mycobacteria) which might be present in a sample. Thus, in addition to being substantially inclusive, these probes are exclusive, as defined above.

Partially inclusive oligonucleotides, which are defined above, are also broadly useful for the detection of members of the genus Mycobacteria. These oligonucleotides detect substantially all Mycobacteria, but not all and, thus, to be useful for the identification of Mycobacteria, such oligonucleotides generally are used as a mixture with other partially inclusive oligonucleotides. Like the previous category of probes, they can also be used in a mixture with substantially inclusive oligonucleotides in order, for example, to amplify the signal from a subset of Mycobacteria which may hybridize only weakly to the substantially inclusive oligonucleotides. Such oligonucleotides are also useful as primers for PCR amplification of Mycobacterial nucleic acids to which they are substantially complementary.

Substantially inclusive non-exclusive oligonucleotides, which are defined above, are useful for example as detection oligonucleotides in a capture/detection dual oligonucleotides assay system. A preferred embodiment of this assay system is described above. It is not a necessary property of the non-exclusive oligonucleotides that they do not bind to non-Mycobacterial nucleic acid which may be present in the sample because nucleic acids from non-Mycobacterial species are removed from the mixture by virtue of the properties of the capture oligonucleotide. Such oligonucleotides are also useful as primers for PCR amplification of Mycobacterial nucleic acids to which they are substantially complementary.

Partially inclusive non-exclusive oligonucleotides are useful as members of sets of detection oligonucleotides in a capture/detection dual probe assay. As with the substantially inclusive non-exclusive oligonucleotides described above, exclusivity is not an important characteristic for a detection probe in a dual probe assay. The reason that these oligonucleotides must generally be used as members of probe sets is that individually, they do not detect the full spectrum of Mycobacterial species. Thus, it is possible that if a partially inclusive detection probe were used independently (rather than in a set of two or more such detection oligonucleotides) in a dual probe assay, a false negative determination could be made due to the fact that partially inclusive detection oligonucleotides, by definition, do not recognize all members of the Mycobacterial genus. Such oligonucleotides are also useful as primers for PCR amplification of Mycobacterial nucleic acids to which they are substantially complementary.

Subgeneric Specificity

Partially inclusive oligonucleotides can be substantially inclusive for a subgeneric group (i.e., they are substantially complementary to about 90% or more of the bacteria in the subgenus). For example, the Mycobacterial subgenus known as the *Mycobacterium tuberculosis* complex includes the species *M. tuberculosis*, *M. bovis* (bcg), *M. africanum*, and *M. microti*. As shown in Example 2 (and in Table 3b), oligonucleotides 2366 and 2371 are substantially inclusive for this subgenus. In addition, they are fully exclusive in that they do not hybridize to the bacteria listed in Table 4.

Another recognized Mycobacterial subgenus is the slow-growing subgenus. This subgenus is defined, for example, by Wayne and Kubica (in *Bergey's Manual of Systemic Bacteriology*, Volume 2 (1986), pp. 1436–1457, Sneath et al. editors, Williams and Wilkins, Baltimore, Md.). This subgenus includes the following Mycobacterial species: *Mycobacterium tuberculosis, Mycobacterium microti, Mycobacterium kansasii, Mycobacterium marinum, Mycobacterium* gastri, *Mycobacterium nonchromogenicum, Mycobacterium terrae, Mycobacterium triviale, Mycobacterium malmoense, Mycobacterium shimoidei, Mycobacterium gordonae, Mycobacterium asiaticum, Mycobacterium szulgai, Mycobacterium simiae, Mycobacterium scrofulaceum, Mycobacterium avium, Mycobacterium intracellulare, Mycobacterium xenopi, Mycobacterium ulcerans, Mycobacterium haemophilum, Mycobacterium farcinogenes, Mycobacterium lepraemurium, Mycobacterium paratuberculosis* and *Mycobacterium leprae*. As shown in Example 2, oligonucleotides 2369 and 2362 are substantially inclusive for this subgeneric group (i.e. they are substantially complementary to about 90% or more of the bacteria in the subgenus).

Oligonucleotide Construction and Hybridization Conditions

The oligonucleotides of this invention are prepared by conventional methods. The conditions under which the oligonucleotides are hybridized to the Mycobacterial rRNA (the hybridization criteria) are variable. Those skilled in the art recognize that hybridization criteria are governed by such reaction parameters as the concentration and type of ionic species present in the hybridization solution, the types and concentrations of denaturing agents present and/or the temperature of hybridization. Generally, as hybridization conditions become more stringent, longer oligonucleotides are preferred if stable hybrids are to be formed. As a corollary, the stringency of the conditions under which hybridization occurs (e.g., based on the type of assay to be performed) will dictate certain characteristics of the preferred oligonucleotides to be employed. Such relationships are well understood and can be readily manipulated by those skilled in the art.

In Example 2 below, hybridization was carried out at 60° C. for 3 or more hours in 1.08M NaCl, 0.06M NaH$_2$PO$_4$ (pH 7.7), 6 mM-EDTA, 0.01% SDS, 10 X Denhardt's and 100 ug/ml denatured salmon sperm DNA, followed by subsequent washes in 0.3M NaCl, 0.04M TrisHCl (pH 7.8) and 2 mM EDTA. Under these conditions, the oligonucleotides used are as described. If the conditions were altered, however, characteristics of the probes (e.g., length, extent of complementarity) will also be altered.

EXAMPLES

Example 1

Oligonucleotide Design

The first step taken in the development of the oligonucleotides of the present invention involved identification of regions of 16S and 23S rRNA which potentially could serve as target sites for Mycobacterium specific nucleic acid oligonucleotides. As a practical matter, it is difficult to predict, a priori, which non-Mycobacterial organisms might be present in any test sample.

Because of the large number of such potential non-Mycobacterial bacteria, demonstrating exclusivity for any given oligonucleotide sequence is not only unpredictable, but also extremely difficult and laborious. A more rigorous criterion was adopted to obviate the need to know what non-Mycobacterial bacteria might be present in all test samples that ultimately will be screened using the oligonucleotides. This entailed knowledge of the phylogenetic relationships among different Mycobacterial species and between Mycobacteria and other groups of bacteria.

Specifically, an operating but previously unproven hypothesis was adopted that the exclusivity criterion could be satisfied by determining that if a particular target region in Mycobacterium rRNA could be identified which was sufficiently different from evolutionary relatives of Mycobacteria, then an oligonucleotide complementary to such a sequence could be used to distinguish between Mycobacterium and the relatives by hybridization assay. Based on phylogenetic observations, it then was extrapolated that rRNA sequences of more distantly related organisms, even though their actual identity may not necessarily be known, should be predictably different in a particular region of sequence than the aforementioned close evolutionary relative of Mycobacteria. However, it could not be predicted, a priori, whether such regions exist, or if they do, where within the rRNA such regions will be located.

As the first step in identifying regions of Mycobacterial rRNA which could potentially serve as useful target sites for complementary oligonucleotides, complete nucleotide sequences of the 16S and nearly complete sequence of 23S rRNAs from a few Mycobacterial species were determined. Coding regions of 23S rRNA genes of Mycobacterium were amplified by polymerase chain reaction (see U.S. Pat. No. 4,683,202) from about 0.5 to 2.0 micrograms of genomic DNA of Mycobacterium using primers 940 (forward primer) and 987 (reverse primer) as a set. Primer 2205 hybridizes to the rRNA-like strand of the 5S ribosomal RNA gene of Mycobacterium genus only. Oligonucleotides 940 and 987 are designed for use in the assays employing amplification of nearly the entire 23S rRNA gene (rDNA) of nearly all bacteria including Mycobacterium. The amplified 23S rRNA genes were cloned and sequenced by standard laboratory protocols. The Mycobacterium rRNA nucleotide sequences were compared to each other and to other available rRNA nucleotide sequences, in particular to *Rhodococcus equi* (16S). Comparison of the sequences of several Mycobacterial species and their close relatives Rhodococcus proved especially valuable. Several regions of sequence were identified which appeared to be different between species of Mycobacteria and between Mycobacteria and non-Mycobacterial bacteria. The locations of these regions within the 16S and 23S rRNA sequences are shown in Tables 1 and 2, respectively.

Oligonucleotides, 28–52 nucleotides in length, were designed which would hybridize preferentially to *Mycobacterium tuberculosis* complex, *Mycobacterium avium* complex, *Mycobacterium kansasii, Mycobacterium fortuitum* or all Mycobacteria. These were designed in light of the following goals:

1) to maximally utilize the nucleotide sequence differences useful for distinguishing one Mycobacterial species from another or groups of Mycobacteria from each other or Mycobacteria from other bacteria (indicated as upper case letters in the region of Core Variation in Tables 1 and 2); and 2) to minimize the effect of self-complementarity both locally within the target rRNA and between probe molecules. Table 3 exemplifies the inclusivity behavior of the preferred oligonucleotides toward a representative sampling of Mycobacteria and a few non-Mycobacteria in a dot-blot hybridization assay. Table 4 exemplifies the exclusivity behavior of the preferred oligonucleotides toward a representative sampling of non-Mycobacterial bacteria in a dot-blot hybridization assay.

The foregoing oligonucleotide selection strategy yielded a number of oligonucleotide probes useful for identifying Mycobacteria in samples. Oligonucleotide probes 2213, 2214, 2215, 2233, 2234, 2235, 2236, 2240, 2247, 2248, 2155, 2156, and 2257 are designed from 16S rRNA sequences. Oligonucleotides 2362, 2364, 2365, 2366, 2368, 2369, 2371, 2372, 2373, 2374, 2375, 2376, 2377, 2378, 2379, 2380, 2382, 2383, 2384, 2385, 2388, 2389, 2390, 2392, 2393, 2425, 2426 and 2428 are designed from 23S rRNA sequences. The sequences of the preferred oligonucleotides are set forth below:

16S rRNA oligonucleotides

SEQ ID NO: 17:
5'-ATTTCACGAACAACGCGACAAACCAC-CTACGAG-3'
SEQ ID NO: 20:
5'-CAGGAATTCCAGTCTCCCCTGCAGTACTCTAGT-3'
SEQ ID NO: 10:
5'CTTCTCCACCTACCGTCAATC-CGAGAGAACCCGGACCTTCGTCG-3'
SEQ ID NO: 27:
5'GGCCACAAGGGAACGCCTATCTCTA-GACGCGTCCTGTGCATAT-3'
SEQ ID NO: 9:
5'-CAATCCGAGAGAACCCGGACCTTCGTC-GATGGTGAAAG-3'
SEQ ID NO: 2:
5'-AGTTTCCCAGGCTTATCCCGAAGTG-CAGGGCAG-3'
SEQ ID NO: 34:
5'-CGAGTCCCCACCATTACGTGCTGGCAAC-3'
SEQ ID-NO: 19:
5'-ATCGCCCGCACGCTCACAGTTAAGCCGT-GAGATTTC-3'
SEQ ID NO: 11:
5'-CTTCTCCACCTACCGTCAATCCGAGACAAC-3'
SEQ ID NO: 3:
5'-TAGACCCAGTTTCCCAGGCTTATCCCGGA-3'
SEQ ID NO: 35:
5'-CGAGTCCCCGGCATTACCCGCTGGCAAC-3'
SEQ ID NO: 26:
5'-CTGCACACAGGCCACAAGGGAACGC-CTATCTCT-3'
SEQ ID NO: 18:
5'CTCACAGTTAAGCCGTGAGATTTCAC-GAACAACGCGAC-3'

23S rRNA Oligonucleotides

SEQ ID NO: 56:
5'-CTGACTGCCTCTCAGCCGGGTAGCGCT-GAGACATATCCTCCC-3'
SEQ ID NO: 48:
5'-GGTTACCCATGCGTGCGGTTTAGCCTGT-TCCGCGTTC-3'
SEQ ID NO: 84:
5'-CTCTACCTCCAACAAGAAACATGT-GACGCTGCACC-3'
SEQ ID NO: 64:
5'-CCATCACCACCCTCCTCCGGAGAG-GAAAAGGAGGCTCTG-3'
SEQ ID NO: 92:
5'-CTACCCACACCCACCACAAGGTGGATGT-GCCGCGG-3'
SEQ ID NO: 101:
5'-GGGCTTAAATTCTCCGCTTCACCT-TGCGGGTTAAC-3'
SEQ ID NO: 72:
5'-GAACACGCCACTATTCACACGCGCGTAT-GCGTGTGGGTCGCCCTATTCAG-3'
SEQ ID NO: 110:
5'-CTCCGCCCCAACTGGCGTCGAGGTTTCA-CAGTCTC-3'
SEQ ID NO: 53:
5'-GGTATCACATGCATACGGTTTAGCCATC-CCTTCTTTC-3'
SEQ ID NO: 114:
5'-CTCCACAACCACTGGCGTGGCTGCTTCA-CAGTCTC-3'
SEQ ID NO: 89:
5'-CGTCTCACTGCCACACTCTTGGACT-TGTCGGCATT-3'
SEQ ID NO: 69:
5'-GGCACGCCATCACCCCACGACAAAGTC-GAAGGCTCTG-3'
SEQ ID NO: 105:
5'-GGGCTTAAATTCTCTGCTTCAC-CCCGAAGGTTAAC-3'
SEQ ID NO: 96:
5'-GCTCCCCTACCCAACGATAAATCGTTGC-CGCGG-3'
SEQ ID NO: 77:
5'-CCAGAACACACCACTACACCACACAC-TACTGTGCGGATACCCCTATTCAG-3'
SEQ ID NO: 61:
5'-CTGACTACCCTCCAGCCAGGTAGAACTG-GAAAAACAGGTCCC-3'
SEQ ID NO: 51:
5'-GGTTACCCATGCGTGCGGTTTAGCCAT-GTTCCGGTTC-3'
SEQ ID NO: 94:
5'-GCTCCCCTACCCAACCTTGCGGTTGTCGCGG-3'
SEQ ID NO: 67:
5'-GGCACGCCATCACCCCACGAAAGGGCTCTG-3'
SEQ ID NO: 59:
5'-CTGACTGCCCCTCAGCCGGGTAGAGCT-GAGACGKATCGTACCC-3'
SEQ ID NO: 103:
5'-GGGCTTAAATTCTCCGCTTCACCCT-TGCGGGTTAAC-3'
SEQ ID NO: 79:
5'-CCAGAACACGCAACTACACCCCRAAGG-GATGCGCCCTATTCAG3'
SEQ ID NO: 112:
5'-CTCCACCCCAACTGGCGTTGAGGTTTCA-CAGTCTC-3'
SEQ ID NO: 116:
5'-CTCCACACAAACTGGGCGTCTGTGCT-TCAAAGTCTC-3'
SEQ ID NO: 107:
5'-GGGCTTAAACTTCCTGCTTCACT-TACGGGTTAAC-3'
SEQ ID NO: 98:
5'-GCTCCCCTACCCACATCCACCGTAAA-GATGAATGTGCCGCGG-3'

Spacer Region Oligonucleotides (5' to 23S rRNA gene)

SEQ ID NO: 41: 5'-CAACAAAAACCAAAGAATAT-TGCACAAAGAACACGCC-3'

SEQ ID NO: 43: 5'-CAAAAACCAAAGAATAAAAT-TGCACAAAAGAACACGC-3'

SEQ ID NO: 45: 5'-CAAAAACCAAAAATGAGTT-TAAAAGAAATTGCACATC-3'

The oligonucleotides and their target sequences in the 16S and 23S rRNAs of *Mycobacterium tuberculosis* virulent strain, *Mycobacterium avium*, *Mycobacterium kansasii* and *Mycobacterium fortuitum* are shown in Tables 1 and 2. The corresponding nucleotide positions of the *E. coli* 16S and 23S rRNAs are also shown. Since the *E. coli* sequences were among the first full 16S and 23S sequences obtained, the assigned position numbers are a convenient standard for explicitly identifying the homologous regions in the Mycobacterial rRNAs under consideration.

In addition, 9 oligonucleotide primers (1637, 1638, 1260, 940, 622, 986., 993, 987 and 2205) were designed for the PCR amplification of parts of Mycobacterium 16S and 23S rRNA genes in order to facilitate the analysis of these genes in these slow growing organisms. The sequences of these primers are given below.

16S Probe Primers

Primer 1637: 5'-AAGGAGGTGATCCAGCC-3' (SEQ ID NO: 118)

Primer 1638: 5'-AGAGTTTGATCCTGGCTC-3' (SEQ ID NO: 119)

Primer 1260: 5'-TGYACACACCGCCCGT-3' (SEQ ID NO: 120)

23S Probe Primers

Primer 622: 5'-ATTGGCCTTTCACCCC-3' (SEQ ID NO: 121)

Primer 940: 5'-GAACTGAAACATCTWAGT-3' (SEQ ID NO: 122)

Primer 986: 5'-TTAGCMTTTCACCCC-3' (SEQ ID NO: 123)

Primer 987: 5'-CTTAGATGCYTTCAGC-3' (SEQ ID NO: 124)

Primer 993: 5'-TTGGCMTTTCACCCC-3' (SEQ ID NO: 125)

Primer 1021: 5'-AGGGRAACARCCCAGA-3' (SEQ ID NO: 126)

5S rRNA Probe Primer

Primer 2203: 5'-ccgaattcgtcgacaacCAGGCTTAGCTTCCGGGTTCGG- 3' (SEQ ID NO: 127)

Lower case letters used-in the above listing designate sequence designed to add useful restriction endonuclease recognition cloning sites to the amplified products. Letters other than A, T, G or C designate the following:
N=A, T, G or C
M=A or C
R=A or G
W=A or T
S=C or G
Y=C or T
K=G or T
B=C, G or T
D=A, G or T
H=A, C or T
V=A, C or G More than one oligonucleotide probe has been designed to a number of the target regions shown in Table 2 corresponding variously to complements of the sequences of *Mycobacterium tuberculosis*, or *Mycobacterium avium* or *Mycobacterium kansasii* or *Mycobacterium fortuitum* or all four. The particular sequence upon which each oligonucleotide is based (i.e., is complementary to) is provided in Tables 1 and 2 by inspection of the aligned oligonucleotide and target sequences. Thus, for example, it can be seen in Table 2 that probe 2371 is complementary to the *Mycobacterium kansasii* sequence. Base pairing rules dictate that A pairs with T and G pairs with C, although various non-canonical base pairs to a first approximation [i.e. G:U, G:T or A:G] can be introduced into the probe for specific purposes. However, it is expected (and desirable) that some cross-hybridization between species by one or both oligonucleotide probes will take place. Likewise, oligonucleotide probes 2235 and 2248 are based on *Mycobacterium tuberculosis*, *Mycobacterium avium*, *Mycobacterium kansasii* and *Mycobacterium fortuitum* 16S rRNA sequences.

The specific hybridization behavior of the oligonucleotide probes described above are dependent to a significant extent on the assay format in which they are employed. Conversely, the assay format will dictate certain of the optimal design features of particular oligonucleotides. The scope of this invention is not to be construed as restricted to the specific sequence of nucleotides in the list of oligonucleotides above. For example, the length of these particular oligonUcleotides was optimized for use in the dot blot assay (and certain other anticipated assays) described herein. It is well known to one skilled in the art that optimal oligonucleotide length will be a function of the stringency of the hybridization conditions chosen and hence the lengths of the instant oligonucleotides may be altered in accordance therewith. Also, in considering sets comprised of more than one oligonucleotide, it is desirable that all oligonucleotides behave in a compatible manner in any particular format in which they are both employed. Thus, the exact length of a particular oligonucleotide will to a certain extent reflect its specific intended use. The sequence data in Tables 1 and 2 suggest that the oligonucleotides of the present invention should exhibit a variety of useful hybridization properties with respect to the specific detection of *Mycobacterium tuberculosis*, *Mycobacterium avium*, *Mycobacterium kansaaii* and *Mycobacterium fortuitum* or all Mycobacteria to the exclusion of other bacteria. However, relatively few Mycobacterial sequences were inspected. It is possible that sequence variation might exist in other Mycobacterial strains not inspected by sequence analysis. Such variation might reduce or eliminate hybridization by the prospective oligonucleotides to some or many untested Mycobacteria.

Equally as important as the inclusivity behavior of the oligonucleotides, is their exclusivity behavior. The number and types of non-Mycobacterial strains which might be encountered in a sample are extremely large. Therefore, the behavior of the oligonucleotides toward representative Mycobacteria and non-Mycobacterial species was determined by hybridization analysis using a dot blot procedure. While hybridization data for each of the individual oligonucleotides of the present invention are provided, it should be noted that useful combinations (sets) of oligonucleotides which exhibit hybridization behaviors that are the sum of the individual oligonucleotides also is explicitly predicted by the data.

Example 2

Dot Blot Analysis of Oligonucleotide Hybridization Behavior

Dot blot analysis, in accordance with well known procedures, involves immobilizing a nucleic acid or a population of nucleic acids on a solid support, such as nitrocellulose, nylon, or other derivatized membranes. Either DNA or RNA can be easily immobilized on such a support and subsequently can be probed or tested for hybridization under any of a variety of conditions (i.e., stringencies) with oligonucleotides of interest. Under stringent conditions, oligonucleotides whose nucleotide sequences have greater complementarity to the target sequence will exhibit a higher level of hybridization than oligonucleotides having a lesser degree of complementarity.

For the experiment shown in Tables 3 and 4, rRNA was extracted by CsTFA method and DNA was extracted from Mycobacteria by standard methods. 16S and 23S rRNA genes of Mycobacterium from about 0.5 to 1.0 microgram of total DNA were amplified using 16S rRNA-specific primers 1638 (forward primer) and 1637 (reverse primer), or 23S primers 940 (forward primer) and 987 (reverse primer) by polymerase chain reaction. One tenth of a microgram of purified RNA (Lane et al., *Proc. Natl. Acad. Sci. USA* 82:6955–6959 (1985)), or PCR amplified ribosomal DNA from each of the indicated organisms was spotted on Nytran or nitrocellulose filters. The oligonucleotides were end labeled with radioactive phosphorous 32, using standard procedures.

For the oligonucleotides described herein, prehybridization was done at 60 degrees C for 3 or more hours (in a solution containing 1.08M NaCl, 0.06M NaH$_2$PO$_4$ (pH 7.7), 6 mM EDTA, 0.01% SDS, 10 X Denhardt's and 100 micrograms/milliliter denatured salmon sperm DNA). Hybridization to rDNA targets was done at 60 degrees C for 14–16 hours (in a hybridization solution containing 1.08M NaCl, 0.06M NaH$_2$PO4 (pH 7.7), 6 mM EDTA and 0.01% SDS), followed by three 15 minute post-hybridization washes at 60 degrees C (in 0.3M NaCl, 0.04M Tris-HCl (pH 7.8), 2 mM EDTA) to remove unbound oligonucleotide probes.

Following hybridization and washing as described above, the hybridization filters were exposed to X-ray film and the intensity of the signal was scored visually with respect to control lanes having a known quantity of target material (DNA). A scale of hybridization intensity ranging from ++++ (hybridization signal equivalent to that of control Mycobacterial DNA for which a perfect match between oligonucleotide probe and target sequences was explicitly determined by sequence analysis) to + (barely detectable even after long exposure of X-ray-film) and —(no detectable hybridization) has been used to conveniently compare hybridization signals between different organisms and the oligonucleotides.. This reporting format is preferred to raw numerical representation of the extent of hybridization as it permits ready visual scanning of the summary data.

As is evident in Table 3, oligonucleotide probe 2235 hybridizes to the amplified 16S ribosomal RNA genes and RNA of all the Mycobacterium isolates except *M. ulcerans* and *M. vaccae*. The rest of the oligonucleotide probes hybridize to different Mycobacterial species in varying potentially useful patterns to either the amplified 16S or 23S rDNA.

The above example also demonstrates that primer set 1637 and 1638 can be used to amplify Mycobacterial 16S rRNA genes and primer set 940 and 987 can be used to amplify 23S rRNA genes from base 189 to base 2759, and primer set 940 and 2203 can be used to amplify 23S rRNA gene from base 189 into the 5S rRNA gene from genomic DNA and that the amplified material can be further tested with specific oligonucleotides targeted to the 16S and 23S rRNA.

Equivalents

Those skilled in the art will know, or be able to ascertain, using no more than routine experimentation, many equivalents to the specific embodiments of the invention described herein. These and all other equivalents are intended to be encompassed by the following claims.

TABLE 1

16S rRNA-TARGETED PROBES AND TARGET SEQUENCES

| E. coli #s | | |
|---|---|---|
| | 132       143       164    171 | |
| 1- E. coli | GUCUGGG-AAA CUGCCUGAUGGAGGGGAUAACUACUGGAAACGGUAGCUAAUACC | E. coli |
| 2- P2233 | 3'-GACGGGACGUGAAGCCCUAUUCGGACCCUUUGA-5' | P2233 |
| 3- P2240 | 3'-AGGCCCUAUUCGGACACCCUUUGACCCAGAU-5' | P2240 |
| 4- M. tbRv37 | ACGUGGGUGAUCU$_g$CCCUGCACUUCGGGAUAAGCCUGGAAACUGGGUCUAAUACC | M. tbRv37 |
| 5- M. avium | ACGUGGGCAAUCUGcCCUGCACUUCGGGAUAAGCCUGGAAACUGGGUCUAAUACC | M. avium |
| 6- M. kansa | ACGUGGGCAAUCUGCCCUGCACUUCGGGAUAAGCCUGGAAACUGGGUCUAAUACC | M. kansa |
| 7- M. fortu | ACGUGGGUAAUCUGCCCUGCACUUUGGGAUAAGCCUGGAAACUGGGUCUAAUACC | M. fortu |

| E. coli #s | | |
|---|---|---|
| | 436       446       459       481       497  501 | |
| 8- E. coli | CGGUUGUAAAGUACUUUCAGCGGGGAGGAAGG-GAGUAAAGUUAAUACCUUUGCUCAUUGACGUUACCCGCAGAAGAAGCACCGGCUAAC | E. coli |
| 9- P2215 | 3'-GAAAGUGGUAGCUGCUUCCAGGCCAA- | P2215 |
| 10- P2213 | 3'-GCUGCUUCCAGGCCCAA- | p2213 |
| 11- p2236 | 3'-CAA- | P2236 |
| 12- M. tbR37 | CGGGU$_n$GUAAACCUCUUUCACCAUCGACGAAGGUCCGGGU------- | M. tbR37 |
| | GAGAGCCUAACUGCCAUCCACCUCUUC-5' | |
| 13- M. avium | CGGGU$_n$GUAAACCUCUUUCACCAUCGACGAAGGUCCGGGU------- | M. avium |
| | GAGAGCCUAACUGCCAUCCACCUCUUC-5' | |
| 14- M. kansa | CGGGUUGUAAACCUCUACCACCAAGACGAAGGUCCGGGU------- | M. kansa |
| | CUCUCGGAUUGACGUAGGUGGAGAAGCACCGGCCAAC | |
| 15- M. fortu | CGGGU$_n$GUAAACCGUUUUCAAUAGGGACGAAGCG------- | M. fortu |
| | UUCUCGGAUUGACGUAGGUGGAGAAGCACCGGCCAAC | |
| | | |
| | CUCUCGGAUUGACGUAGGUGGAGAAGCACCGGCCAAC | |
| | CAAGUGACGUUACCUAUAGAAGAAGGACCGGCCAAC | |

| E. coli #s | | |
|---|---|---|
| | 578       592       606  610       629       641  645       649 | |
| 16- E. coli | GGGCGUAAAGCGCACGCAGGCGGUUUGUUAAGUCAGAUGUGAAAUCCCCGGGCUCAACCUGGGAACUGCAUCUGAUACUGGCAAGCUUGAGUCUCGUAGAG | E. coli |
| 17- P2155 | 3'-GAGCAUCCACCAAACAGCGCAACAAGCACUUUA-5' | P2155 |
| 18- P2257 | 3'-CAGCGCAACAAGCACUUUAGAGUGCGAAUUGACACUC-5' | P2257 |
| 19- P2235 | 3'-CUUUAGAGUGCGAAUUGACACUUGACACUGCACGCCCGCUA-5' | P2235 |
| 20- P2156 | 3'-TGATCTCATGACGTCC | P2156 |
| 21- M. tbR37 | GGGCGUAAAGAGCUCGUAGGU$_n$GUUUGUCGCGU$_n$GUUUGUCGCGU$_n$GUUCGUGAAAUCUCACGGCUUAACCGGUGAGCGUGCAGACGAUGACUGCGGG | M. tbR37 |
| 22- M. avium | GGGCGUAAAGAGCUCGUAGGU$_n$GUUUGUCGCGU$_n$nUUCGUGAAAUCUCACGGCUUAAGUGGUGGAUCGAUAGUACUGCGG | M. avium |
| 23- M. kansa | GGGCGUAAAGAGCUCGUAGGUGGUUUGUCGCGUUGUU CGUGAAAUCUCACGGCUUAACUGUGAAAUCUCACGGCGAUAGUACUGCAGG | M. kansa |
| 24- M. fortu | GGGCGUAAAGAGCUCGUAGGU$_n$GUUUGUCGCGU$_n$nUUCGUGAAAUCUCACAGCUU$_n$UUACUGGGGGGAUACGGGCGAUAGAGUACUGCGG | M. fortu |

| E. coli #s | | |
|---|---|---|
| | 680 | |
| E. coli | GGGGGUAGAAUUCCAGGUGUAGCGGU | E. coli |
| P2156 | CCTCTGACCTTAAGGAC-5' | p2156 |
| M. tbR37 | GGAGACUGGAAUUCCUGGUGUAGCGG | M. tbR37 |
| M. avium | GGAGACUGGAAUUCCUGGUGUAGCGG | M. avium |
| M. kansa | GGAGACUGGAAUUCCUGGUGUAGCGG | M. kansa |
| M. fortu | GGAGACUGGAAUUCCUGGUGUAGCGG | M. fortu |

TABLE 1-continued 16S rRNA-TARGETED PROBES AND TARGET SEQUENCES

|   | E. coli #s | 993 | 1010 | 1024 | 1036 | 1045 | 1052 | |
|---|---|---|---|---|---|---|---|---|
| 25- | E. coli | UACCUGGUCUUGACAUCC---ACGGAAGUUUCAGAGAUGAGAAUGUGCCUU-CGGGAACC-GUGAGACAGGUGCUGCAUGGCUGU | | | | | | E. coli |
| 26- | P2248 | | | 3'-TCTCTATCCG---CAAGGGAA-CACCGG-ACACACGTC-5' | | | | P2248 |
| 27- | P2214 | 3'-TATACGTGTCCTGCGCAGATCTCTATCCG---CAAGGGAA-CACCGG-5' | | | | | | P2214 |
| 28- | PROBE | | | 3'-AAGGGAA-CACCGG-ACACACGTCCACCACG-5' | | | | PROBE |
| 29- | M. tbR37 | UACCUGGGUUUGACAUGCACAGGACGCGUCUAGAGAUAGGC---GUUCCCUU-GUGGCC-UGUGUGCAGGUGGUGCAUGGCUGUC | | | | | | M. tbR37 |
| 30- | M. avium | UACCUGGGUUUGACAUGCACAGGACACGGACGCGUCUAGAGAGGC---GUUCCCUU-GUAGCCAUGUGCAGGUGGUGCAUGGCUGUC | | | | | | M. avium |
| 31- | M. kansa | UACCUGGGUUUGACAUGCACAGGACGCGUCUAGAGAUAGGC---GUUCCCUU-GUGGCC-UGUGUGCAGGUGGUGCAUGGCUGUC | | | | | | M. kansa |
| 32- | M. fortu | UACCUGGGUUUGACAUGCACAGGACGCGUCAGUAGAUAUUG---GUUCCCUU-GUnGCC-UGUGUGCAGGUGGUGCAUGGCUGUC | | | | | | M. fortu |

|   | E. coli #s | | 1121 | | 1147 | | | |
|---|---|---|---|---|---|---|---|---|
| 33- | E. coli | AACGAGCGCAACCCUUAUCCUUUGUUGCCAGCGGUC---CGGCCGGGAACUCAAAGGAGACUCAGUGAU | | | | | | E. coli |
| 34- | P2234 | | 3'-CAACGGTCGTGCA--TTACCACCCCTGAGC-5' | | | | | P2234 |
| 35- | P2247 | | 3'-CAACGGTCGCCCA--TTACGGCCCCTGAGC-5' | | | | | P2247 |
| 36- | M. tbR37 | CGAGCGCAACCCUUGUCUCUAUGUUGCCAGCACGU---AAUGGUGGGGACUGCGUGAGAGACUGCCGGGGUUAA | | | | | | M. tbR37 |
| 37- | M. avium | CGAGCGCAACCCUUGUCUCUAUGUUGCCAGCACGU---nAUGCCGGGGACUCGUGAGAGACUGCGGGGUCAA | | | | | | M. avium |
| 38- | M. kansa | CGAGCGCAACCCUUGUCUCUAUGUUGCCAGCGGGU---AAUGCCGGGGACUCGUGAGAGACUGCCGGGGUCAA | | | | | | M. kansa |
| 39- | M. fortu | CGAGCGCAACCCUUGUCUCUAUGUUGCCAGCACGU---nUAUGGUGGGGACUCGUGAGAGACUGCCGGGGUCAA | | | | | | M. fortu |

TABLE 2

23S rRNA-TARGETED PROBES AND TARGET SEQUENCES

| # | | E. coli#s | Sequence | E. coli#s | |
|---|---|---|---|---|---|
| 40- | E. coli | | 4<br>GGUAAGGCGACU–AAGCGU–ACACGGUGGAUGCCCUGGCAGUCAGAGGCGAU<br>38 | E. coli | |
| 41- | E. coli | P2363 | 3'–CCGCACAAGAACACGUUAUAAGAACCAAAACAAC–5' | P2363 | E. coli |
| 42- | M. tb | | CUGCCCGGUGGCUGUGUGCUUGUGCAAUAUAUGUUGUGUGUUGUUGAAGUG | P2367 | M. tb |
| 43- | M. tb(av) | P2367 | 3'–CGCACAAGAAACACGUUAAAUAAGAAACCAAAAC–5' | | M. tb(av) |
| 44- | M. kan | P2382 | GCGUUGCUACGGGUAGCGGUGUUCUUUUGUGCAAUUUAUUCUUUGGUUUGUGUUGUUGAAGUG | P2382 | M. kan |
| 45- | P2373 | | 3'–CUACACGUUAAAGAAAAUUUGAGUAAAAACCAAAAAC–5' | P2373 | |
| 46- | M. for | | UGGUUUUGUGUGAUGUGCAAUUCUUUUAAACUCAUUUUGGUUUUUGUG–UUGUAAGUG | | M. for |
| 47- | E. coli | | 254<br>AGCGGCGA–GCGAAC–GGGGAGCAGCCCAGACCUGAAUC–<br>281 | E. coli | |
| 48- | E. coli | P2364 | 3'–CUUGCGCCUUGUCCGAUUUGG–CGUGCGUACCCAUUGG–5' | P2364 | E. coli |
| 49- | M. tb | | AGUGGGCGA–GCGAAC–SG–AACAGGCUAAACC–GCACGCAUGGUAACCGGUAGGGUUGC | | M. tb |
| 50- | M. tb(av) | | AGUGGGCGA–GCGAAC–GGAACGGCUAAACC–GCACGCAUGgGUAACCGGUAGGGUUGU | | M. tb(av) |
| 51- | P2388 | | 3'–CUUG–GCCUUGUACGAUUUGGCGUGCGUACCCAUUGG–5' | P2388 | |
| 52- | M. kan | | AGUGGGCGA–GCGAAC–CGGAACAUGGCUAAACCGCACGCAUGGUAACCGGUAGGGUUGU | | M. kan |
| 53- | P2373 | | 3'–CUUUCUUCCUACCGAUUUGG–CAUACGUACACUAUGG–5' | P2373 | |
| 54- | M. for | | AGUGGGCGA–GCGAAAGAAGGAUGGCUAAACC–GUAUGCAUGGGAUACCGGUAGGGUUGU | | M. for |
| 55- | E. coli | | 281<br>AGU–––––GUGUGUGUUA<br>284 | E. coli | |
| 56- | E. coli | P2362 | 3'–CCCCUC–CUAUACAGAGUCGCGAUGGCCGACUCUCCGUCAGUC–5' | P2362 | E. coli |
| 57- | M. tb | | UGUGUGCGGGUGUGGGAG–GAUAUGUCUCAGGCUACCCGGCUGAGAGGCAGUCAGAAAGUGUCGUGGUUA | | M. tb |
| 58- | M. tb(av) | | GUGUGUGCGGGUGUGGGAG–––AUAUGUCUCAGGCUACCCGGCUACCCGGCAGUCAGAGGCAGUCAGAAAGUGUCGUGGUUA | | M. tb(av) |
| 59- | P2388 | | 3'–CCCAUGCTKGCAGAUGCGAGAUGGGGGCUCUCCGGGCUCGAGGGCAGUCAGUC–5' | P2388 | |
| 60- | M. kan | | GUGUGCGGGUGUGGGAUCGAUMCGUCUCAGUCUACCCGGCUGAGGGGCAGUCAGAAAGUGUCGUGGUUA | | M. kan |
| 61- | P2373 | | 3'–CCCUG–GACAAAAAGGTCAAGAUUCCUAGUUCCAGUUCCACCGGACGGACCUCCCAUCAGUC–5' | P2373 | |
| 62- | M. for | | GUGUGCGGGUGUGGGAC–CUGUUUUCCAGUUCCAGUUCCAGGGGCAGUCAGAAAA–UGUCGUGGUUA | | M. for |
| 63- | E. coli | | 535<br>UACAAGCAGUGGGAGCAC–GCUU–––––––AGGCGUGUGGACUGCGUACCUUUGUAUAUGG<br>559 | E. coli | |
| 64- | E. coli | P2366 | 3'–GUCUCGGAGGAAAAGGAGAGGCCUCCUC–––CCACCACUACC–5' | P2366 | E. coli |
| 65- | M. tb | | UACAAUCCGUCAGAGCCUCCUUUUCCUCCGGAGAG––GGUGGUGAUGGCGUGCGUGCCUUUGAAGAAUGA | | M. tb |
| 66- | M. tb(av) | | UACAAUCCGUCAGAGCCUCCUUUUCCUCCGGAGAG––GGUGGUGAUGGCGUGCGUGCCUUUGAAGAAUGA | | M. tb(av) |
| 67- | P2384 | | 3'–GUCUCGGGAAAGC–––––––––ACCCCACUACCGCACGG–5' | P2384 | |
| 68- | M. kan | | UACAAUCCGUCAGAGCCCUUUCG–––––––UGGGGGUGAAUGGCGUGCCCUUUUGAAGAAUGA | | M. kan |
| 69- | P2376 | | 3'–GUCUCGGAAGCUGAAACAGC–––ACCCCACUACCGCACGG–5' | P2376 | |
| 70- | M. for | | UACAAUCCGUCAGAGCCUCUUGACUUGUCG–––––––UGGGGUGAUGGCGUGCGUGAGUAGUCGGUUA | | M. for |
| 71- | E. coli | | 640<br>GGGAAACCGAGUCUUAACUGGCG–––––––UUAAGUUGCAGGGUAUGACCCGAAACCCGGU<br>666 | E. coli | |
| 72- | E. coli | P2371 | 3'–GACUUAUCCCGUGUGCUAUGCGCACACUUAUCACCGCACAAG–5' | P2371 | E. coli |
| 73- | M. tb | | GCGAAAGCGAGUCUGAAUAGGGCGACCUCCACACGCGCAUACGGCAUCUGGACCUCGGAGU | | M. tb |
| 74- | M. tb(av) | | GCGAAAGCGAGUCUGAAUAGGGCGACCUCCACACGCGCAUACGGCAUCUGGACCCGAAGCGGAGU | Mtb(av) | |
| 75- | PK23 | | 3'––––––ATCACCCACAAGACC–5' | PK23 | |

TABLE 2-continued 23S rRNA-TARGETED PROBES AND TARGET SEQUENCES

| # | Organism/Probe | Sequence |
|---|---|---|
| 76- | M. kan | GCGAAAGCGAGUCUGAAUAGGGCGUAUCGCGCGAGCGUGUG------UAGUGGCGUGUUCUGACCCGAAGCGGAGU M. kan |
| 77- | P2379 | 3'-GACTTATCCCCATAGGCGTGTCATCACACCACA---TCACCACAAGACC-5' P2379 |
| 78- | M. for | GCGAAAGCGAGUCUGAAUAGGGGAUCCGCACAGUAGUGUGUGU----AGUGGUGUGUCUGACCCGAAGCGGAGU M. for |
| 79- | P2392 | 3'-GACTTATCCCG------CGTAGGGAARCCCCA-CATCAACGCACAAGACC-5' P2392 |
| 80- | M. avium | GCGAAAGCGAGUCUGAAUAGGGC---------GCAUCCCUnGGGGU-GUAGUUGCNUGUUCUGACCCGAAGCGGAGU M. avium |
| | | 830 864 |
| | E. coli#s | E. coli#s |
| 81- | E. coli | GAAAGCUAUUU-AGG-UAGCGCCUCGUGAAUUCAUCUCCGGGGUAGUGC-ACUGUUUCGGCA E. coli |
| 82- | M. tb | GAAAUGCAUUU-AGG-UGCAGCGUUGCGUGGGUUCACCGCGGAGGUAGAGCUACUGGAUGCCGA M. tb |
| 83- | M. kan | GAAAUGCAUUU-AGG-UGCAGCGUGCGUGUCACCAGGUAGAGCUACUGGAUGCCGA M. kan |
| 84- | P2365 | 3'-CC-ACGTCGCAGTGTACAAAGAACAACCTCCATCTC-5' P2365 |
| 85- | M. for | GAAAUGCAUUU-AGG-UGCAGCGUCACAUGUUUCUGUGGAGGUAGAGCUACUGGAUGCCGA M. for |
| | | 921 944 |
| | E. coli#s | E. coli#s |
| 86- | E. coli | CAAACUGCGAAUACCGGAGAAUGUUA---UCACGGGAGACACACGGCGGGUGCU E. coli |
| 87- | M. tb | CAAACUCCGAAUGCCGUGGUGUAAAG---CGUGGCAGUGAGACGGCGGGGAU M. tb |
| 88- | M. kan | CAAACUCCGAAUGCCGUGGUGUAUAG----CGUGGCAGUGAGACGGCGGGGKAU M. kan |
| 89- | P2375 | 3'-TTACGGCTGTTCAGGTTCTCACACCGTCACTCTGC-5' P2375 |
| 90- | M. for | CAAACUCCGAAUGCCGACAAGUCCAAGAGUGUGGCAGUGAGACGGCGGGGAU M. for |
| | | 1158 1190 1196 |
| | E. coli#s | E. coli#s |
| 91- | E. coli | AAGCUGCGCAGCGA---CGCUUAUGCGGUUGUUGGGUAGGGAGC-GUUCUGUAA-GCC E. coli |
| 92- | P2368 | 3'-GGCGCCGTGTAG-GTGGAACACCACCACACCCATC-5' P2368 |
| 93- | M. tb | AAGCCGCGGCACAUC-CACCUUGUGGUGGGGUGUGGGGAGC-GUCC--CUCAUUC M. tb |
| 94- | P2383 | 3'-GGCGCTGTTGG-------CGTTCCAACCCATCCCTCG-5' P2383 |
| 95- | M. kan | AAGCCGCGACAACC------GCAAGGUUGGUAGGGAGC-GUCC--CUCAUUC M. kan |
| 96- | P2378 | 3'-GGCGCCGT--------TGCTAAATAGCAACCCATCCCTCG-5' P2378 |
| 97- | M. for | AAGCCGCGGCA-----ACGAUUUAUCGUUGGUGGGGAGC--GUCC--UGCAUUC M. for |
| 98- | P2428 | 3'-GGCGCCGTGTAAGTAGAAATGCCACCTACACCCATCCCCTCG-5' P2428 |
| 99- | M. avium | AAGCCGCGGCACAUUCACUUUACGGUGAGUGGGUAGGGAGC-GUCC--CCCAUUC M. avium |
| | | 1863 1894 |
| | E. coli#s | E. coli#s |
| 100- | E. coli | UUAAUUGAUGGGGUUA-GC--GCAA---GC-GAAGCUCUUGAUCGAAGCCCCGGUAAACGGCGGC E. coli |
| 101- | P2369 | 3'-CAAT-TG-GGCGTT--CCA-CTTCGCCTCTTAAATTCGGG-5' P2369 |
| 102- | M. tb | UUAAGAGGACCCGGUUA-AC-CCGCAA-AC-CCGCAA-GGU-GAAGCGGAGAAUUUAAGCCCCAGUAAACGGCGGU M. tb |
| 103- | P2390 | 3'-CAAT-TG-GGCGTTCCA-CTTCGCCTTCGCCCTCTTAAATTCGGG-5' P2390 |
| 104- | M. kan | GUUAAGAGGACCCGGUUA-AC-CCGCAAGGGU-GAAGCGGAGAAUUUAAGCCCCAGUAAACGGCGG M. kan |
| 105- | P2377 | 3'-CAAT-TG-GAAGC-CCCA-CTTCGTCTCTTAAATTCGGG-5' P2377 |
| 106- | M. for | GUUAAGAGGACCUGGUUA-AC-CUUCG-GGGU-GAAGCAGAGAAUUUAAGCCCCAGUAAACGGCGG M. for |
| 107- | P2426 | 3'-CAAT-TG-GGCATT--CA-CTTCGTCCTTCAAATTCGGG-5' P2426 |
| 108- | M. avium | GUUAAGAGGACCCGGUUA-AC-CCGUAA--GU-GAAGCAGGAAGUUUAAGCCCCAGUAAACGGCGG M. avium |
| | | 2125 2159 |
| | E. coli#s | E. coli#s |
| 109- | E. coli | GUAGGAUAGGUGGGAGGCUUUGAAGUGUGGACGCCAGU-CUGCAUGGAGCCGACCUUGAAAU E. coli |
| 110- | P2372 | 3'-CTCTGACACTTTGGAGCTGCGGTCA-ACCCCGCCTC--5' P2372 |
| 111- | M. tb | GUAGGAUAGGUGGGAGACUGUGAAACCUCGACGUGAAACCUGGCGGCGAGUCGUUGUUGAAAC M. tb |

TABLE 2-continued 23S rRNA-TARGETED PROBES AND TARGET SEQUENCES

| 112- | P2393 | 3'-CTCTGACACTTGGAGTTGCGGTCA-ACCCCACCTC-5' | P2393 |
| 113- | M. kan | GUAGGAUAGGUGGGAGACUGUGAAACCUCAACGCCAGU-UGGGGUGGAGUCGUUGUUGAAAU | M. kan |
| 114- | P2374 | 3'-CTCTGACACTTCGTGCGGTCA-CCAACACCTC-5' | P2374 |
| 115- | M. for | GUAGGAUAGGUGGGAGACUGUGAAGCAGCCACGCCAGU-GGUUGUGGAGUCGUUGUUGAAAU | M. for |
| 116- | P2425 | 3'-CTCTGAAACTTCGTGTCTGCGGTCAAACACACCTC-5' | P2425 |
| 117- | *M. avium* | GUAGGAUMGGYSGGAGACUUUGAAGCACAGACGCCCAGUUUGUGUGGAGUCGUUGUUGAAAU | *M. avium* |

TABLE 3a

DOT BLOT HYBRIDIZATION of 16S rRNA-TARGETED PROBES

| | | PROBE HYBRIDIZATION | | | | |
|---|---|---|---|---|---|---|
| Genus strain | strain | 2233 | 2240 | 2215 | 2213 | 2236 |
| Mycobacterium tuberculosis Rv37 | ATCC25618 | ++++ | ++ | ++++ | ++++ | ++++ |
| Mycobacterium tuberculosis H37Ra | 2487 | ++++ | ++ | ++++ | ++++ | ++++ |
| Mycobacterium tuberculosis complex | 3526 | ++++ | +++ | ++++ | ++++ | ++++ |
| Mycobacterium tuberculosis complex | 3528 | ++++ | ++ | ++++ | ++++ | ++++ |
| Mycobacterium tuberculosis complex | 3531 | ++++ | ++ | ++++ | ++++ | ++++ |
| Mycobacterium tuberculosis complex | 3533 | ++++ | + | ++++ | ++++ | ++++ |
| Mycobacterium tuberculosis complex | 3535 | ++++ | ++ | ++++ | ++++ | ++++ |
| Mycobacterium tuberculosis complex | 3536 | ++++ | ++ | ++++ | ++++ | ++++ |
| Mycobacterium tuberculosis complex | 3538 | ++++ | ++ | ++++ | ++++ | ++++ |
| Mycobacterium tuberculosis complex | 3539 | ++++ | +++ | ++++ | ++++ | ++++ |
| Mycobacterium tuberculosis complex | 3544 | ++++ | + | ++++ | ++++ | ++++ |
| Mycobacterium tuberculosis complex | 3545 | ++++ | + | ++++ | ++++ | ++++ |
| Mycobacterium tuberculosis complex | 3547 | ++++ | + | ++++ | ++++ | ++++ |
| Mycobacterium tuberculosis complex | 3548 | ++++ | + | ++++ | ++++ | ++++ |
| Mycobacterium tuberculosis complex | 3549 | ++++ | ++ | ++++ | ++++ | ++++ |
| Mycobacterium tuberculosis complex | 3552 | ++++ | ++ | ++++ | ++++ | ++++ |
| Mycobacterium tuberculosis complex | 3553 | ++++ | ++ | ++++ | ++++ | ++++ |
| Mycobacterium tuberculosis complex | 3554 | ++++ | ++ | ++++ | ++++ | ++++ |
| Mycobacterium africanum | 3468 | ++++ | ++++ | ++++ | ++++ | ++++ |
| Mycobacterium asiatiicum | 3057 | ++++ | − | ++++ | ++++ | ++++ |
| Mycobacterium avium | 3246 | ++++ | − | ++++ | ++++ | ++++ |
| Mycobacterium avium | 3532 | ++++ | − | ++++ | ++++ | ++++ |
| Mycobacterium avium | 3542 | ++++ | − | ++++ | ++++ | ++++ |
| Mycobacterium avium | 3555 | ++++ | − | ++++ | ++++ | ++++ |
| Mycobacterium avium | 3559 | ++++ | − | ++++ | ++++ | ++++ |
| Mycobacterium avium | 3561 | ++++ | − | ++++ | ++++ | ++++ |
| Mycobacterium avium | 3562 | ++++ | − | ++++ | ++++ | ++++ |
| Mycobacterium avium type 4 | | ++++ | − | ++++ | ++++ | ++++ |
| Mycobacterium avium 1 | | ND | ND | ++++ | ++++ | +++ |
| Mycobacterium avium 2 | | ND | ND | ++++ | ++++ | +++ |
| Mycobacterium avium 3 | | ND | ND | ++ | ++++ | ++ |
| Mycobacterium avium 4 | | ND | ND | ++ | ++++ | ++ |
| Mycobacterium avium 5 | | ND | ND | ++ | ++++ | ++ |
| Mycobacterium avium 6 | | ND | ND | ++ | ++++ | +++ |
| Mycobacterium avium 8 | | ND | ND | +++ | ++++ | +++ |
| Mycobacterium avium 9 | | ND | ND | +++ | +++ | +++ |
| Mycobacterium avium 10 | | ND | ND | ++ | ++ | ++ |
| Mycobacterium avium 12 | | ND | ND | ++ | ++ | ++ |
| Mycobacterium avium 13 | | ND | ND | ++++ | ++ | ++ |
| Mycobacterium avium 15 | | ND | ND | +++ | ++ | ++ |
| Mycobacterium avium | 3562 | ++++ | − | ++++ | ++++ | +++ |
| Mycobacterium bovis | 3510 | ++++ | ++++ | ++++ | − | ++++ |
| Mycobacterium bovis BCG | | ++++ | + | ++++ | ++++ | ++++ |
| Mycobacterium gordonae | 3260 | ++++ | ++ | ++++ | ++++ | ++++ |
| Mycobacterium intracellularae | 3422 | ++++ | − | ++++ | ++++ | ++++ |
| Mycobacterium intracellularae | 3425 | ++++ | − | ++++ | ++++ | ++++ |
| Mycobacterium intracellularae | 3436 | ++++ | − | ++++ | ++++ | ++++ |
| Mycobacterium kansasii | 3706 | ++++ | + | ++++ | ++++ | ++++ |
| Mycobacterium marinum | 3508 | ++++ | +++ | ++++ | ++++ | ++++ |
| Mycobacterium scrofulaceum | 0305 | ++++ | + | + | ++++ | ++++ |
| Mycobacterium species | 3705 | ND | ND | − | − | − |
| Mycobacterium species | 3743 | ND | ND | − | − | − |
| Mycobacterium szulgai | 3701 | ND | ND | ++++ | ++++ | ++ |
| Mycobacterium terrae | 3247 | ++++ | + | − | − | − |
| Mycobacterium triviale | 3426 | ++++ | − | − | − | − |
| Mycobacterium ulcerans | 3744 | ND | ND | − | − | − |
| Mycobacterium valentiae | 3660 | ND | ND | − | − | − |
| Mycobacterium agri | 3503 | ++++ | − | − | − | − |
| Mycobacterium aichiense | 3501 | ++++ | − | − | − | − |
| Mycobacterium aurum | 3505 | ++++ | − | − | − | − |
| Mycobacterium austroafricanum | 3502 | ++++ | − | − | − | − |
| Mycobacterium chelonei | 3537 | ++++ | − | ++ | − | − |
| Mycobacterium chelonei | 3248 | ++++ | − | − | − | − |
| Mycobacterium chitae | 3499 | ++++ | − | − | − | − |
| Mycobacterium chubuense | 3497 | ++++ | − | − | − | − |
| Mycobacterium diernhoferi | 3508 | ++++ | − | − | − | − |
| Mycobacterium duvalii | 3500 | ++++ | − | − | − | − |
| Mycobacterium fallax | 3658 | ++++ | − | − | − | − |
| Mycobacterium flavescens | 3506 | ++++ | − | − | − | − |
| Mycobacterium fortuitum | 3413 | ++++ | − | − | − | − |
| Mycobacterium fortuitum | | ++++ | − | − | − | − |
| Mycobacterium gadium | 3420 | ++++ | − | − | − | − |
| Mycobacterium gilvum | 3419 | ++++ | − | − | − | − |

TABLE 3a-continued

| | | | | | | |
|---|---|---|---|---|---|---|
| Mycobacterium komossense | 3661 | ++++ | − | − | − | − |
| Mycobacterium neoaurum | 3642 | ++++ | − | − | − | − |
| Mycobacterium obuense | 3416 | ++++ | − | − | − | − |
| Mycobacterium parafortuitum | 3639 | ++++ | − | − | − | − |
| Mycobacterium phlei | 3414 | ++++ | − | − | − | − |
| Mycobacterium porcinum | 3641 | ++++ | − | − | − | − |
| Mycobacterium pulveris | 3644 | ++++ | − | − | − | − |
| Mycobacterium rhodesiae | 3412 | ++++ | − | − | − | − |
| Mycobacterium senegalense | 3640 | ++++ | − | − | − | − |
| Mycobacterium smegmatis | 0306 | ++++ | − | − | − | − |
| Mycobacterium sphagni | 3659 | ++++ | − | − | − | − |
| Mycobacterium thermoresistable | 3645 | ++++ | − | − | − | − |
| Mycobacterium takainse | 3638 | ++++ | − | − | − | − |
| Mycobacterium vaccae | 3637 | ++++ | − | − | − | − |
| Mycobacterium acapulensis | 3415 | ++++ | − | − | − | − |
| Mycobacterium gallinarum | 3498 | ++++ | − | − | − | − |
| Mycobacterium engbaekii | 3509 | − | ++++ | ++++ | ++++ | − |
| Mycobacterium lactis | 3703 | ++++ | − | − | − | − |
| Mycobacterium moriokaense | 3656 | ++++ | − | − | − | − |
| Mycobacterium petroleophilum | 3655 | ++++ | − | − | − | − |
| Mycobacterium porferae | 3657 | ++++ | − | − | − | − |
| (pending) | 3534 | ++++ | − | − | − | − |
| (pending) | 3558 | ++++ | + | − | − | − |
| Rhodococcus | 3563 | ++++ | − | − | − | − |

DOT BLOT HYBRIDIZATION of 16S rRNA-TARGETED PROBES
TO PCR AMPLIFIED 16S rDNA GENES

| | | PROBE HYBRIDIZATION | | | | |
|---|---|---|---|---|---|---|
| Genus strain | strain | 2233 | 2240 | 2215 | 2213 | 2236 |
| Mycobacterium acapulensis | 3415 | ++++ | − | +++ | +++ | +++ |
| Mycobacterium avium 7 | | ND | ND | ++++ | ++++ | ++++ |
| Mycobacterium avium 11 | | ND | ND | ++++ | ++++ | ++++ |
| Mycobacterium avium 14 | | ND | ND | ++++ | ++++ | ++++ |
| Mycobacterium farcinogenes | 3704 | ND | ND | − | − | + |
| Mycobacterium gastri | 3702 | ND | ND | +++ | + | ++ |
| Mycobacterium paratuberculosis | | ++++ | ND | ++++ | +++ | +++ |
| Mycobacterium haemophilum | | ++++ | ND | ++ | +++ | +++ |
| Mycobacterium intracelluraire | | ++++ | ND | +++ | ++ | ++ |
| Mycobacterium lepraemurium | | ++++ | ND | + | − | + |
| Mycobacterium malmoense | 3579 | ND | ND | ++++ | ++ | ++ |
| Mycobacterium microti | | ++++ | ND | ++ | +++ | +++ |
| Mycobacterium novum | 3775 | ND | ND | − | + | ++ |
| Mycobacterium simiae | 3776 | ND | ND | − | − | + |
| Mycobacterium tuberculosis complex | | ++++ | ND | ++++ | ++++ | ++ |
| Mycobacterium xenopi (26) | | ++++ | ND | ++ | ++ | + |
| pending (17) | | ++++ | ND | ++++ | ++++ | ++ |
| pending (19) | | ++++ | ND | ++ | ++ | + |

DOT BLOT HYBRIDIZATION of 16S rRNA-TARGETED PROBES

| | | PROBE HYBRIDIZATION | | | | |
|---|---|---|---|---|---|---|
| Genus species | strain | 2155 | 2156 | 2235 | 2257 | 2248 |
| Mycobacterium tuberculosis | Rv37 | ++++ | ++++ | ++++ | ++++ | ++++ |
| Mycobacterium tuberculosis | 2487 | ++++ | ++++ | ++++ | ++++ | ++++ |
| Mycobacterium tuberculosis complex | 3526 | +++ | ++++ | ++++ | ++++ | ++++ |
| Mycobacterium tuberculosis complex | 3528 | +++ | ++++ | ++++ | ++++ | ++++ |
| Mycobacterium tuberculosis complex | 3531 | +++ | ++++ | ++++ | ++++ | ++++ |
| Mycobacterium tuberculosis complex | 3533 | +++ | ++++ | ++++ | ++++ | ++++ |
| Mycobacterium tuberculosis complex | 3535 | +++ | ++++ | ++++ | ++++ | ++++ |
| Mycobacterium tuberculosis complex | 3536 | ++++ | ++++ | ++++ | ++++ | ++++ |
| Mycobacterium tuberculosis complex | 35368 | +++ | ++++ | ++++ | ++++ | ++++ |
| Mycobacterium tuberculosis complex | 3539 | ++++ | ++++ | ++++ | ++++ | ++++ |
| Mycobacterium tuberculosis complex | 3544 | ++++ | ++++ | ++++ | ++++ | ++++ |
| Mycobacterium tuberculosis complex | 3545 | ++++ | ++++ | ++++ | ++++ | ++++ |
| Mycobacterium tuberculosis complex | 3547 | ++++ | ++++ | ++++ | ++++ | ++++ |
| Mycobacterium tuberculosis complex | 3548 | ++++ | ++++ | ++++ | ++++ | ++++ |
| Mycobacterium tuberculosis complex | 3549 | ++++ | ++++ | ++++ | ++++ | ++++ |
| Mycobacterium tuberculosis complex | 3552 | ++++ | ++++ | ++++ | ++++ | ++++ |
| Mycobacterium tuberculosis complex | 3553 | ++++ | ++++ | ++++ | ++++ | ++++ |
| Mycobacterium tuberculosis complex | 3554 | ++++ | ++++ | ++++ | ++++ | ++++ |
| Mycobacterium africanum | 3468 | ++++ | ++++ | ++++ | ++++ | ++++ |
| Mycobacterium asiaticum | 3057 | ++++ | ++++ | +++ | ++++ | ++++ |
| Mycobacterium avium | 3246 | ++++ | ++++ | +++ | ++++ | ++++ |
| Mycobacterium avium | 3532 | ++++ | ++++ | +++ | ++++ | +++ |

TABLE 3a-continued

| | | | | | | |
|---|---|---|---|---|---|---|
| Mycobacterium avium | 3542 | ++++ | ++++ | ++++ | ++++ | ++++ |
| Mycobacterium avium | 3555 | ++++ | ++++ | ++++ | ++++ | ++++ |
| Mycobacterium avium | 3559 | ++++ | ++++ | ++++ | ++++ | ++++ |
| Mycobacterium avium | 3561 | +++ | ++++ | ++++ | ++++ | ++++ |
| Mycobacterium avium | 3562 | ++++ | ++++ | ++++ | ++++ | ++++ |
| Mycobacterium avium type 4 | | +++ | ++++ | ++++ | ++++ | ++++ |
| Mycobacterium avium 1 | | ND | ND | ++++ | +++ | +++ |
| Mycobacterium avium 2 | | ND | ND | ++++ | +++ | +++ |
| Mycobacterium avium 3 | | ND | ND | ++++ | ++++ | +++ |
| Mycobacterium avium 4 | | ND | ND | +++ | ++++ | +++ |
| Mycobacterium avium 5 | | ND | ND | ++++ | ++++ | +++ |
| Mycobacterium avium 6 | | ND | ND | ++++ | +++ | +++ |
| Mycobacterium avium 8 | | ND | ND | ++++ | +++ | +++ |
| Mycobacterium avium 9 | | ND | ND | ++++ | +++ | +++ |
| Mycobacterium avium 10 | | ND | ND | ++++ | +++ | ++ |
| Mycobacterium avium 12 | | ND | ND | ++++ | +++ | ++ |
| Mycobacterium avium 13 | | ND | ND | ++++ | +++ | ++ |
| Mycobacterium avium 15 | | ND | ND | ++++ | +++ | ++ |
| Mycobacterium avium | 3562 | ++++ | ++++ | ++++ | ++++ | ++++ |
| Mycobacterium bovis | 3510 | +++ | ++++ | ++++ | ++++ | ++++ |
| Mycobacterium bovis BCG | | +++ | ++++ | ++++ | ++++ | ++++ |
| Mycobacterium gordonae | 3260 | ++++ | ++++ | ++++ | ++++ | ++++ |
| Mycobacterium intracellularae | 3422 | ++++ | ++++ | ++++ | ++++ | ++++ |
| Mycobacterium intracellularae | 3425 | ++++ | ++++ | ++++ | ++++ | ++++ |
| Mycobacterium intracellularae | 3436 | ++++ | +++ | ++++ | ++++ | ++++ |
| Mycobacterium kansasii | 3706 | ++++ | ++++ | ++++ | ++++ | ++++ |
| Mycobacterium marinum | 3508 | ++++ | ++++ | ++++ | ++++ | ++++ |
| Mycobacterium scrofulaceum | 0305 | ++++ | ++++ | ++++ | ++++ | ++++ |
| Mycobacterium species | 3705 | ND | ND | ++++ | − | + |
| Mycobacterium species | 3743 | ND | ND | ++++ | + | + |
| Mycobacterium szulgai | 3701 | ND | ND | ++++ | +++ | ++ |
| Mycobacterium terrae | 3247 | + | ++++ | ++++ | − | ++++ |
| Mycobacterium triviale | 3426 | ++ | ++++ | ++++ | − | − |
| Mycobacterium ulcerans | 3744 | ND | ND | − | − | − |
| Mycobacterium valentiae | 3660 | ND | ND | ++++ | + | + |
| Mycobacterium agri | 3503 | ++ | ++++ | ++++ | − | ++++ |
| Mycobacterium aichiense | 3501 | ++++ | ++++ | ++++ | − | ++++ |
| Mycobacterium aurum | 3505 | ++++ | ++++ | ++++ | − | ++++ |
| Mycobacterium austroafricanum | 3502 | ++++ | ++++ | ++++ | − | ++++ |
| Mycobacterium chelonei | 3537 | ++ | ++++ | ++++ | + | ++++ |
| Mycobacterium chelonei | 3248 | ++ | ++++ | ++++ | ++ | ++++ |
| Mycobacterium chitae | 3499 | ++++ | ++++ | ++++ | − | ++++ |
| Mycobacterium chubuense | 3497 | ++++ | ++++ | ++++ | ++ | ++++ |
| Mycobacterium diernhoferi | 3508 | ++++ | +++ | ++++ | ++ | ++++ |
| Mycobacterium duvalii | 3500 | ++++ | ++++ | ++++ | ++ | ++++ |
| Mycobacterium fallax | 3658 | +++ | ++++ | ++++ | − | ++++ |
| Mycobacterium flavescens | 3506 | ++++ | ++++ | ++++ | − | ++++ |
| Mycobacterium fortuitum | 3413 | ++++ | ++++ | ++++ | ++ | ++++ |
| Mycobacterium fortuitum | | ++++ | ++++ | ++++ | ++ | ++++ |
| Mycobacterium gadium | 3420 | ++++ | ++++ | ++++ | ++++ | ++++ |
| Mycobacterium gilvum | 3419 | ++ | ++++ | ++++ | ++ | ++++ |
| Mycobacterium komossense | 3661 | ++++ | ++++ | ++++ | − | ++++ |
| Mycobacterium neoaurum | 3642 | ++++ | +++ | ++++ | ++ | ++++ |
| Mycobacterium obuense | 3416 | ++++ | +++ | ++++ | − | ++++ |
| Mycobacterium parafortuitum | 3639 | ++++ | ++++ | ++++ | ++ | ++++ |
| Mycobacterium phlei | 3414 | ++++ | ++++ | ++++ | ++ | ++++ |
| Mycobacterium porcinum | 3641 | ++++ | ++++ | ++++ | ++ | ++++ |
| Mycobacterium pulveris | 3644 | ++++ | ++++ | ++++ | ++ | ++++ |
| Mycobacterium rhodesiae | 3412 | ++++ | ++++ | ++++ | − | ++++ |
| Mycobacterium senegalense | 3640 | ++++ | ++++ | ++++ | ++ | ++++ |
| Mycobacterium smegmatis | 306 | ++++ | ++++ | ++++ | ++ | ++++ |
| Mycobacterium sphagni | 3659 | +++ | ++++ | ++++ | + | ++++ |
| Mycobacterium thermoresistable | 3645 | +++ | ++++ | ++++ | − | ++++ |
| Mycobacterium takainse | 3638 | ++++ | ++++ | ++++ | ++ | ++++ |
| Mycobacterium vaccae | 3637 | ++++ | ++++ | − | ++++ | +++ |
| Mycobacterium acapulensis | 3415 | ++++ | ++++ | ++++ | − | ++++ |
| Mycobacterium gallinarum | 3498 | +++ | ++++ | ++++ | − | ++++ |
| Mycobacterium engbaekii | 3509 | +++ | ++++ | ++++ | − | ++++ |
| Mycobacterium lactis | 3703 | +++ | ++++ | ++++ | − | ++++ |
| Mycobacterium moriokaense | 3656 | +++ | ++++ | ++++ | ++ | ++++ |
| Mycobacterium petroleophilum | 3655 | +++ | ++++ | ++++ | + | ++++ |
| Mycobacterium porferae | 3657 | ++++ | ++++ | ++++ | + | ++++ |
| (pending) | 3534 | ++++ | ++++ | ++++ | ++ | ++++ |
| (pending) | 3558 | +++ | ++++ | ++++ | + | ++++ |
| Rhodococcus | 3563 | − | − | + | + | − |

TABLE 3a-continued

DOT BLOT HYBRIDIZATION of 16S rRNA-TARGETED PROBES of PCR AMPLIFIED 16S rDNA GENES

| Genus species | strain | 2155 | 2156 | 2235 | 2257 | 2248 |
|---|---|---|---|---|---|---|
| Mycobacterium acapulensis | 3415 | ++++ | ++++ | ++++ | – | ++++ |
| Mycobacterium avium | | ++++ | ++++ | ++++ | ++++ | ++++ |
| Mycobacterium avium 7 | | ND | ND | ++++ | ++++ | ++ |
| Mycobacterium avium 11 | | ND | ND | ++++ | ++++ | ++ |
| Mycobacterium avium 14 | | ND | ND | ++++ | ++++ | ++ |
| Mycobacterium farcinogenes | 3704 | ND | ND | ++++ | – | – |
| Mycobacterium gastri | 3702 | ND | ND | ++++ | ++ | + |
| Mycobacterium paratuberculosis | | ++++ | ++++ | ++++ | – | +++ |
| Mycobacterium haemophilum | | ++++ | ++++ | ++ | – | ++ |
| Mycobacterium intracellularae | | ++++ | ++++ | ++++ | ++++ | ++++ |
| Mycobacterium lepraemurium | | ++ | ++ | ++ | – | ++ |
| Mycobacterium malmoense | 3579 | ND | ND | ++++ | +++ | ++ |
| Mycobacterium microti | | ++++ | ++++ | ++++ | – | ++++ |
| Mycobacterium novum | 3775 | ND | ND | ++++ | ++ | ++ |
| Mycobacterium simiae | 3776 | ND | ND | ++++ | – | + |
| Mycobacterium tuberculosis complex | | ++++ | ++++ | ++++ | ++++ | ++++ |
| Mycobacterium xenopi (26) | | ++++ | ++++ | ++++ | ++++ | ++++ |
| pending (17) | | ++++ | ++++ | ++++ | ++++ | ++++ |
| pending (19) | | ++++ | ++++ | ++++ | ++++ | ++++ |

DOT BLOT HYBRIDIZATION of 16S rRNA-TARGETED PROBES

| | | PROBE HYBRIDIZATION | | |
|---|---|---|---|---|
| Genus species | strain | 2214 | 2234 | 2247 |
| Mycobacterium tuberculosis Rv37 | ATCC25618 | ++++ | ++++ | – |
| Mycobacterium tuberculosis Ra37 | 2487 | ++++ | ++++ | – |
| Mycobacterium tuberculosis complex | 3526 | ++++ | ++++ | – |
| Mycobacterium tuberculosis complex | 3528 | ++++ | ++++ | – |
| Mycobacterium tuberculosis complex | 3531 | ++++ | ++++ | – |
| Mycobacterium tuberculosis complex | 3533 | ++++ | ++++ | – |
| Mycobacterium tuberculosis complex | 3535 | ++++ | ++++ | – |
| Mycobacterium tuberculosis complex | 3536 | ++++ | ++++ | – |
| Mycobacterium tuberculosis complex | 3538 | ++++ | ++++ | – |
| Mycobacterium tuberculosis complex | 3539 | ++++ | ++++ | – |
| Mycobacterium tuberculosis complex | 3544 | ++++ | ++++ | – |
| Mycobacterium tuberculosis complex | 3545 | ++++ | ++++ | – |
| Mycobacterium tuberculosis complex | 3547 | ++++ | ++++ | – |
| Mycobacterium tuberculosis complex | 3548 | ++++ | ++++ | – |
| Mycobacterium tuberculosis complex | 3549 | ++++ | ++++ | – |
| Mycobacterium tuberculosis complex | 3552 | ++++ | ++++ | – |
| Mycobacterium tuberculosis complex | 3553 | ++++ | ++++ | – |
| Mycobacterium tuberculosis complex | 3554 | ++++ | ++++ | – |
| Mycobacterium africanum | 3468 | ++++ | ++++ | – |
| Mycobacterium asiaticum | 3057 | +++ | – | ++++ |
| Mycobacterium avium | 3246 | ++++ | – | ++++ |
| Mycobacterium avium | 3532 | ++++ | – | ++++ |
| Mycobacterium avium | 3542 | ++++ | – | ++++ |
| Mycobacterium avium | 3555 | ++++ | – | ++++ |
| Mycobacterium avium | 3559 | ++++ | – | ++++ |
| Mycobacterium avium | 3561 | ++++ | – | ++++ |
| Mycobacterium avium | 3562 | ++++ | – | ++++ |
| Mycobacterium avium type 4 | | ++++ | – | +++ |
| Mycobacterium avium 1 | | ND | ND | ND |
| Mycobacterium avium 2 | | ND | ND | ND |
| Mycobacterium avium 3 | | ND | ND | ND |
| Mycobacterium avium 4 | | ND | ND | ND |
| Mycobacterium avium 5 | | ND | ND | ND |
| Mycobacterium avium 6 | | ND | ND | ND |
| Mycobacterium avium 8 | | ND | ND | ND |
| Mycobacterium avium 9 | | ND | ND | ND |
| Mycobacterium avium 10 | | ND | ND | ND |
| Mycobacterium avium 12 | | ND | ND | ND |
| Mycobacterium avium 13 | | ND | ND | ND |
| Mycobacterium avium 15 | | ND | ND | ND |
| Mycobacterium avium | 3562 | ++++ | – | ++++ |
| Mycobacterium bovis | 3510 | ++++ | ++++ | – |
| Mycobacterium bovis BCG | | ++++ | ++++ | – |
| Mycobacterium gordonae | 3260 | – | ++++ | – |
| Mycobacterium intracellularae | 3422 | ++++ | – | ++++ |
| Mycobacterium intracellularae | 3425 | ++++ | – | ++++ |
| Mycobacterium intracellularae | 3436 | ++++ | – | ++++ |
| Mycobacterium kansasii | 3706 | ++++ | – | ++++ |

TABLE 3a-continued

| | | | | |
|---|---|---|---|---|
| Mycobacterium marinum | 3508 | ++++ | − | ++++ |
| Mycobacterium scrofulaceum | 305 | ++++ | − | ++++ |
| Mycobacterium species | 3705 | ND | ND | ND |
| Mycobacterium species | 3743 | ND | ND | ND |
| Mycobacterium szulgai | 3701 | ND | ND | ND |
| Mycobacterium terrae | 3247 | +++ | ++++ | − |
| Mycobacterium triviale | 3426 | +++ | ++++ | +++ |
| Mycobacterium ulcerans | 3744 | ND | ND | ND |
| Mycobacterium valentiae | 3660 | ND | ND | ND |
| Mycobacterium agri | 3503 | +++ | ++++ | − |
| Mycobacterium aichiense | 3501 | +++ | ++++ | − |
| Mycobacterium aurum | 3505 | ++++ | ++++ | − |
| Mycobacterium austroafricanum | 3502 | ++++ | +++ | − |
| Mycobacterium chelonei | 3537 | − | +++ | ++ |
| Mycobacterium chelonei | 3248 | − | ++++ | − |
| Mycobacterium chitae | 3499 | − | +++ | − |
| Mycobacterium chubuense | 3497 | ++++ | − | − |
| Mycobacterium diernhoferi | 3508 | ++++ | − | ++++ |
| Mycobacterium duvalii | 3500 | +++ | ++++ | − |
| Mycobacterium fallax | 3658 | ++ | ++++ | − |
| Mycobacterium flavescens | 3506 | +++ | ++++ | − |
| Mycobacterium fortuitum | 3413 | ++ | ++++ | − |
| Mycobacterium fortuitum | | + | ++++ | − |
| Mycobacterium gadium | 3420 | ++ | ++++ | +++ |
| Mycobacterium gilvum | 3419 | +++ | ++++ | − |
| Mycobacterium komossense | 3661 | ++++ | ++++ | − |
| Mycobacterium neoaurum | 3642 | ++++ | − | ++++ |
| Mycobacterium obuense | 3416 | ++++ | ++++ | − |
| Mycobacterium parafortuitum | 3639 | +++ | ++++ | − |
| Mycobacterium phlei | 3414 | ++ | ++++ | − |
| Mycobacterium porcinum | 3641 | ++++ | ++++ | − |
| Mycobacterium pulveris | 3644 | ++ | ++++ | − |
| Mycobacterium rhodesiae | 3412 | +++ | ++++ | − |
| Mycobacterium senegalense | 3640 | ++++ | ++++ | − |
| Mycobacterium smegmatis | 306 | +++ | ++++ | − |
| Mycobacterium sphagni | 3659 | ++ | ++++ | − |
| Mycobacterium thermoresistable | 3645 | ++ | − | ++++ |
| Mycobacterium takaiense | 3638 | ++ | ++++ | − |
| Mycobacterium vaccae | 3637 | ++++ | +++ | − |
| Mycobacterium acapulensis | 3415 | ++ | ++++ | − |
| Mycobacterium gallinarum | 3498 | ++++ | +++ | +++ |
| Mycobacterium engbaekii | 3509 | ++++ | − | − |
| Mycobacterium lactis | 3703 | +++ | ++++ | − |
| Mycobacterium moriokaense | 3656 | ++ | − | ++++ |
| Mycobacterium petroleophilum | 3655 | ++++ | ++ | ++++ |
| Mycobacterium porferae | 3657 | + | ++++ | − |
| (pending) | 3534 | + | ++++ | − |
| (pending) | 3558 | − | − | − |

DOT BLOT HYBRIDIZATION of 16S rRNA-TARGETED PROBES TO PCR AMPLIFIED 16S rDNA GENES

| | | PROBE HYBRIDIZATION | | |
|---|---|---|---|---|
| Genus species | strain | 2214 | 2234 | 2247 |
| Mycobacterium acapulensis | 3415 | ++ | ++++ | − |
| Mycobacterium avium | | ++++ | +++ | ++ |
| Mycobacterium avium 7 | | ND | ND | ND |
| Mycobacterium avium 11 | | ND | ND | ND |
| Mycobacterium avium 14 | | ND | ND | ND |
| Mycobacterium farcinogenes | 3704 | ND | ND | ND |
| Mycobacterium gastri | 3702 | ND | ND | ND |
| Mycobacterium paratuberculosis | | ++++ | + | + |
| Mycobacterium haemophilum | | ++++ | − | − |
| Mycobacterium intracellularae | | ++++ | +++ | + |
| Mycobacterium lepraemurium | | ++++ | − | − |
| Mycobacterium malmoense | 3579 | ND | ND | ND |
| Mycobacterium microti | | ++++ | +++ | − |
| Mycobacterium novum | 3775 | ND | ND | ND |
| Mycobacterium simiae | 3776 | ND | ND | ND |
| Mycobacterium tuberculosis complex | | ++++ | +++ | ++ |
| Mycobacterium xenopi (26) | | ++++ | +++ | − |
| pending (17) | | ++++ | +++ | ++ |
| pending (19) | | ++++ | +++ | + |

*Inclusivity data was determined after four hours exposure and exclusivity was determined after overnight exposures.
**Each organism is represented by either 100 ng of CsTFA purified RNA or 200 ng of PCR amplified DNA.
***++++ = positive level of hybridization, + = barely detectable and − = zero.

TABLE 3b

DOT BLOT HYBRIDIZATION OF 23S rRNA-TARGETED
MYCOBACTERIUM TUBERCULOSIS COMPLEX PROBES

| Genus species | strain | PROBE HYBRIDIZATION | | | | | | |
|---|---|---|---|---|---|---|---|---|
| | | 2364 | 2362 | 2366 | 2371 | 2368 | 2369 | 2372 |
| *Mycobacterium tuberculosis* Rv37 | ATCC25618 | ++++ | +++ | ++ | ++ | ++++ | ++++ | ++++ |
| *Mycobacterium tuberculosis* Rh37 | 2487 | ++++ | ++ | ++++ | ++ | ++++ | ++++ | ++++ |
| *Mycobacterium tuberculosis* complex | 3526 | +++ | ++++ | ++++ | +++ | +++ | ++++ | ++++ |
| *Mycobacterium tuberculosis* complex | 3528 | +++ | ++++ | ++++ | +++ | +++ | ++++ | ++++ |
| *Mycobacterium tuberculosis* complex | 3531 | +++ | +++ | ++++ | +++ | +++ | +++ | ++++ |
| *Mycobacterium tuberculosis* complex | 3533 | +++ | ++ | ++++ | +++ | +++ | +++ | ++++ |
| *Mycobacterium tuberculosis* complex | 3535 | +++ | +++ | ++++ | +++ | ++++ | ++++ | ++++ |
| *Mycobacterium tuberculosis* complex | 3536 | +++ | +++ | +++ | +++ | +++ | ++++ | ++++ |
| *Mycobacterium tuberculosis* complex | 3538 | +++ | +++ | ++++ | +++ | ++ | ++++ | ++++ |
| *Mycobacterium tuberculosis* complex | 3539 | ++ | +++ | ++++ | +++ | +++ | ++++ | ++++ |
| *Mycobacterium tuberculosis* complex | 3540 | +++ | +++ | ++++ | +++ | +++ | ++++ | ++++ |
| *Mycobacterium tuberculosis* complex | 3544 | +++ | ++ | ++++ | +++ | ++++ | ++++ | ++++ |
| *Mycobacterium tuberculosis* complex | 3545 | +++ | + | ++++ | +++ | ++++ | ++++ | ++++ |
| *Mycobacterium tuberculosis* complex | 3547 | +++ | + | ++++ | +++ | ++++ | +++ | ++++ |
| *Mycobacterium tuberculosis* complex | 3548 | +++ | + | ++++ | +++ | ++++ | +++ | ++++ |
| *Mycobacterium tuberculosis* complex | 3549 | +++ | + | ++++ | +++ | ++++ | ++ | ++++ |
| *Mycobacterium tuberculosis* complex | 3552 | +++ | +++ | ++++ | +++ | ++++ | ++++ | ++++ |
| *Mycobacterium tuberculosis* complex | 3553 | +++ | +++ | ++ | +++ | ++++ | ++++ | ++++ |
| *Mycobacterium tuberculosis* complex | 3554 | +++ | +++ | ++ | +++ | ++++ | ++++ | ++++ |
| *Mycobacterium africanum* | 3468 | ++++ | ++ | ++++ | +++ | +++ | ++++ | ++++ |
| *Mycobacterium asianticum* | 3507 | ++++ | − | − | − | − | ++ | ++++ |
| *Mycobacterium avium* | 3246 | ++++ | ++ | − | − | + | ++++ | ++++ |
| *Mycobacterium avium* | 3532 | +++ | + | − | − | ++ | ++++ | ++++ |
| *Mycobacterium avium* | 3542 | +++ | + | − | − | + | ++++ | ++++ |
| *Mycobacterium avium* | 3555 | +++ | + | − | − | + | ++++ | ++++ |
| *Mycobacterium avium* | 3559 | +++ | + | − | − | + | ++ | ++++ |
| *Mycobacterium avium* | 3561 | +++ | + | − | − | + | +++ | ++++ |
| *Mycobacterium avium* | 3562 | +++ | + | − | − | + | +++ | ++++ |
| *Mycobacterium avium* type 4 | | ++ | + | − | − | + | ++++ | ++++ |
| *Mycobacterium avium* 1 | | ND | ++ | − | − | − | ND | ND |
| *Mycobacterium avium* 2 | | ND | ++ | − | − | − | ND | ND |
| *Mycobacterium avium* 3 | | ND | ++ | − | − | − | ND | ND |
| *Mycobacterium avium* 4 | | ND | ++ | − | − | − | ND | ND |
| *Mycobacterium avium* 5 | | ND | ++ | − | − | − | ND | ND |
| *Mycobacterium avium* 6 | | ND | ++ | − | − | − | ND | ND |
| *Mycobacterium avium* 8 | | ND | ++ | − | − | − | ND | ND |
| *Mycobacterium avium* 9 | | ND | ++ | − | − | − | ND | ND |
| *Mycobacterium avium* 10 | | ND | + | − | − | − | ND | ND |
| *Mycobacterium avium* 12 | | ND | ++ | − | − | − | ND | ND |
| *Mycobacterium avium* 13 | | ND | + | − | − | − | ND | ND |
| *Mycobacterium avium* 15 | | ND | ++ | − | − | − | ND | ND |
| *Mycobacterium bovis* | 3510 | ++++ | +++ | ++++ | +++ | +++ | +++ | ++++ |
| *Mycobacterium BCG* | | ++ | ++ | ++++ | ++ | ++ | ++++ | ++++ |
| *Mycobacterium gordonae* | 3260 | ++++ | − | − | − | − | +++ | ++++ |
| *Mycobacterium intracellurarae* | 3422 | +++ | ++ | − | − | ++ | ++++ | ++++ |
| *Mycobacterium intracellurarae* | 3425 | +++ | +++ | − | − | ++ | +++ | ++++ |
| *Mycobacterium intracellurarae* | 3436 | ++++ | ++ | − | − | + | +++ | ++++ |
| *Mycobacterium kansasii* | 3706 | ++ | + | + | − | + | ++++ | ++++ |
| *Mycobacterium kansasii* | | ++ | ++ | − | − | ++ | ++++ | ++++ |
| *Mycobacterium marinum* | 3508 | ++++ | +++ | − | − | +++ | +++ | ++++ |
| *Mycobacterium scrofulaceum* | 305 | ++++ | + | − | − | + | ++++ | ++++ |
| Mycobacterium species | 3705 | ND | +++ | − | − | − | ND | ND |
| Mycobacterium species | 3743 | ND | +++ | − | − | − | ND | ND |
| *Mycobacterium szulgai* | 3701 | ND | +++ | − | − | − | ND | ND |
| *Mycobacterium terrae* | 3247 | − | − | − | − | − | − | ++++ |
| *Mycobacterium trivale* | 3426 | − | − | − | − | − | − | ++++ |
| *Mycobacterium ulcerans* | 3744 | ND | − | − | − | − | ND | ND |
| *Mycobacterium valentiae* | 3660 | ND | − | − | − | − | ND | ND |
| *Mycobacterium agri* | 3503 | +++ | − | − | − | − | − | ++++ |
| *Mycobacterium aichiense* | 3501 | +++ | − | − | − | − | − | ++++ |
| *Mycobacterium aurum* | 3505 | +++ | + | − | − | − | − | ++++ |
| *Mycobacterium austroafricanum* | 3502 | +++ | − | − | − | − | − | ++++ |
| *Mycobacterium chelonei* | 3248 | +++ | − | − | − | − | − | ++++ |
| *Mycobacterium chelonei* | 3237 | +++ | − | − | − | − | − | ++++ |
| *Mycobacterium chitae* | 3499 | ++++ | − | − | − | − | − | ++++ |
| *Mycobacterium chubense* | 3497 | ++++ | − | − | − | − | − | ++++ |
| *Mycobacterium duvalli* | 3500 | ++++ | − | − | − | − | − | ++++ |
| *Mycobacterium diernhoferi* | 3504 | − | − | − | − | − | − | +++ |
| *Mycobacterium fallax* | 3658 | − | − | − | − | − | − | +++ |
| *Mycobacterium flavescens* | 3506 | +++ | − | − | − | − | − | +++ |
| *Mycobacterium fortuitum* | 3413 | − | − | − | − | − | − | +++ |
| *Mycobacterium fortuitum* | | − | − | − | − | − | − | +++ |

TABLE 3b-continued

DOT BLOT HYBRIDIZATION OF 23S rRNA-TARGETED
MYCOBACTERIUM TUBERCULOSIS COMPLEX PROBES

| Genus species | strain | PROBE HYBRIDIZATION | | | | | | |
|---|---|---|---|---|---|---|---|---|
| | | 2364 | 2362 | 2366 | 2371 | 2368 | 2369 | 2372 |
| *Mycobacterium gadium* | 3420 | ++ | – | – | – | – | – | ++++ |
| *Mycobacterium gilvum* | 3419 | – | – | – | – | – | – | ++++ |
| *Mycobacterium komossense* | 3661 | – | – | – | – | – | – | ++++ |
| *Mycobacterium neoaurum* | 3642 | +++ | – | – | – | – | – | ++++ |
| *Mycobacterium obuense* | 3416 | ++++ | – | – | – | – | – | ++++ |
| *Mycobacterium parafortuitum* | 3639 | ++ | – | – | – | – | – | ++++ |
| *Mycobacterium phlei* | 3414 | +++ | – | – | – | – | – | ++++ |
| *Mycobacterium porcinum* | 3641 | – | – | – | – | – | – | ++++ |
| *Mycobacterium pulvaris* | 3644 | ++ | – | – | – | – | – | ++++ |
| *Mycobacterium rhodensiae* | 3412 | ++++ | – | – | – | – | – | ++++ |
| *Mycobacterium rhodensiae* | 3412 | ++++ | – | – | – | – | – | ++++ |
| *Mycobacterium senegalense* | 3640 | – | – | – | – | – | – | ++++ |
| *Mycobacterium smegmatis* | 306 | +++ | – | – | – | – | – | ++++ |
| *Mycobacterium sphagni* | 3659 | +++ | – | – | – | – | – | ++++ |
| *Mycobacterium thermoresistible* | 3645 | ++ | – | – | – | – | ++ | ++++ |
| *Mycobacterium takainse* | 3638 | ++++ | – | – | – | – | – | ++++ |
| *Mycobacterium vaccae* | 3637 | ++++ | – | – | – | – | – | ++++ |
| *Mycobacterium acapulensis* | 3415 | +++ | – | – | – | – | – | ++++ |
| *Mycobacterium engbaekii* | 3509 | – | – | – | – | – | – | ++++ |
| *Mycobacterium gallinarum* | 3498 | ++++ | – | – | – | – | – | ++++ |
| *Mycobacterium lactis* | 3703 | – | – | – | – | – | – | ++++ |
| *Mycobacterium moriokaense* | 3656 | ++ | – | – | – | – | – | ++++ |
| *Mycobacterium petroleophilum* | 3655 | +++ | + | – | – | – | – | ++++ |
| *Mycobacterium porferae* | 3657 | ++ | – | – | – | – | – | ++++ |
| (pending) | 3534 | – | – | – | – | – | – | ++++ |
| (pending) | 3558 | – | – | – | – | – | – | ++++ |
| Rhodococcus | 3563 | – | – | – | – | – | – | ++++ |

TABLE 3c

DOT BLOT HYBRIDIZATION OF 23S TARGETED
MYCOBACTERIUM AVIUM COMPLEX PROBES

| Genus species | strain | PROBE HYBRIDIZATION | | |
|---|---|---|---|---|
| | | 2392 | 2425 | 2428 |
| *Mycobacterium tuberculosis* Rv37 | ATCC25618 | – | – | ++++ |
| *Mycobacterium tuberculosis* Rh37 | 2487 | – | – | ++++ |
| *Mycobacterium tuberculosis* complex | 3526 | – | – | +++ |
| *Mycobacterium tuberculosis* complex | 3528 | – | – | +++ |
| *Mycobacterium tuberculosis* complex | 3531 | – | – | +++ |
| *Mycobacterium tuberculosis* complex | 3533 | – | – | +++ |
| *Mycobacterium tuberculosis* complex | 3535 | – | – | +++ |
| *Mycobacterium tuberculosis* complex | 3536 | – | – | ++ |
| *Mycobacterium tuberculosis* complex | 3538 | – | – | +++ |
| *Mycobacterium tuberculosis* complex | 3539 | – | – | +++ |
| *Mycobacterium tuberculosis* complex | 3540 | – | – | +++ |
| *Mycobacterium tuberculosis* complex | 3544 | – | – | +++ |
| *Mycobacterium tuberculosis* complex | 3545 | – | – | +++ |
| *Mycobacterium tuberculosis* complex | 3547 | – | – | +++ |
| *Mycobacterium tuberculosis* complex | 3548 | – | – | +++ |
| *Mycobacterium tuberculosis* complex | 3549 | – | – | +++ |
| *Mycobacterium tuberculosis* complex | 3552 | – | – | +++ |
| *Mycobacterium tuberculosis* complex | 3553 | – | – | +++ |
| *Mycobacterium tuberculosis* complex | 3554 | – | – | +++ |
| *Mycobacterium africanum* | 3468 | – | – | ++++ |
| *Mycobacterium asianticum* | 3507 | + | – | ++++ |
| *Mycobacterium avium* | 3246 | ++ | ++++ | ++++ |
| *Mycobacterium avium* | 3532 | ++++ | ++++ | ++++ |
| *Mycobacterium avium* | 3542 | +++ | ++++ | ++++ |
| *Mycobacterium avium* | 3555 | ++++ | ++++ | ++++ |
| *Mycobacterium avium* | 3559 | ++++ | ++++ | ++++ |
| *Mycobacterium avium* | 3561 | ++++ | ++++ | ++++ |
| *Mycobacterium avium* | 3562 | ++++ | ++++ | ++++ |
| *Mycobacterium avium* type 4 | | + | ++++ | ++++ |
| *Mycobacterium avium* 1 | | ++ | +++ | +++ |
| *Mycobacterium avium* 2 | | ++ | ++ | +++ |
| *Mycobacterium avium* 3 | | ++ | ++ | +++ |
| *Mycobacterium avium* 4 | | +++ | ++ | ++++ |

TABLE 3c-continued

DOT BLOT HYBRIDIZATION OF 23S TARGETED MYCOBACTERIUM AVIUM COMPLEX PROBES

| Genus species | strain | PROBE HYBRIDIZATION | | |
|---|---|---|---|---|
| | | 2392 | 2425 | 2428 |
| Mycobacterium avium 5 | | +++ | ++ | ++++ |
| Mycobacterium avium 6 | | ++ | ++ | ++++ |
| Mycobacterium avium 8 | | +++ | ++ | ++++ |
| Mycobacterium avium 9 | | +++ | +++ | ++++ |
| Mycobacterium avium 10 | | ++ | +++ | ++++ |
| Mycobacterium avium 12 | | +++ | +++ | ++++ |
| Mycobacterium avium 13 | | ++ | ++++ | ++++ |
| Mycobacterium avium 15 | | +++ | +++ | ++++ |
| Mycobacterium bovis | 3510 | − | − | ++++ |
| Mycobacterium BCG | | − | − | ++ |
| Mycobacterium gordonae | 3260 | + | − | ++++ |
| Mycobacterium intracellurarae | 3422 | +++ | − | ++++ |
| Mycobacterium intracellurarae | 3425 | ++ | − | +++ |
| Mycobacterium intracellurarae | 3436 | ++ | ++++ | ++++ |
| Mycobacterium kansasii | 3706 | − | − | − |
| Mycobacterium kansasii | | − | − | − |
| Mycobacterium marinum | 3508 | + | − | − |
| Mycobacterium scrofulaceum | 305 | ++ | − | + |
| Mycobacterium species | 3705 | − | − | + |
| Mycobacterium species | 3743 | − | − | + |
| Mycobacterium szulgai | 3701 | + | − | − |
| Mycobacterium terrae | 3247 | − | − | + |
| Mycobacterium triviale | 3426 | + | − | + |
| Mycobacterium ulcerans | 3744 | − | − | − |
| Mycobacterium valentiae | 3660 | − | − | + |
| Mycobacterium agri | 3503 | − | − | + |
| Mycobacterium aichiense | 3501 | − | − | + |
| Mycobacterium aurum | 3505 | − | − | + |
| Mycobacterium austroafricanum | 3502 | − | − | + |
| Mycobacterium chelonei | 3248 | − | − | + |
| Mycobacterium chelonei | 3237 | − | − | + |
| Mycobacterium chitae | 3499 | +++ | − | + |
| Mycobacterium chubense | 3497 | − | − | + |
| Mycobacterium duvalli | 3500 | − | − | + |
| Mycobacterium diernhoferi | 3504 | − | − | + |
| Mycobacterium fallax | 3658 | − | − | + |
| Mycobacterium flavescens | 3506 | − | − | + |
| Mycobacterium fortuitum | 3413 | − | − | + |
| Mycobacterium fortuitum | | − | − | + |
| Mycobacterium gadium | 3420 | − | − | + |
| Mycobacterium gilvum | 3419 | − | − | + |
| Mycobacterium komossense | 3661 | ++ | − | + |
| Mycobacterium neoaurum | 3642 | − | − | + |
| Mycobacterium obuense | 3416 | − | − | + |
| Mycobacterium parafortuitum | 3639 | − | − | + |
| Mycobacterium phlei | 3414 | − | − | + |
| Mycobacterium porcinum | 3641 | − | − | + |
| Mycobacterium pulvaris | 3644 | − | − | + |
| Mycobacterium rhodensiae | 3412 | − | − | + |
| Mycobacterium senegalense | 3640 | − | − | + |
| Mycobacterium smegmatis | 306 | − | − | + |
| Mycobacterium sphagni | 3659 | − | − | ++ |
| Mycobacterium thermoresistible | 3645 | − | − | + |
| Mycobacterium takainse | 3638 | + | − | ++ |
| Mycobacterium vaccae | 3637 | − | − | − |
| Mycobacterium acapulensis | 3415 | − | − | + |
| Mycobacterium engbaekii | 3509 | − | − | ++ |
| Mycobacterium gallinarum | 3498 | − | − | + |
| Mycobacterium lactis | 3703 | − | − | + |
| Mycobacterium moriokaense | 3656 | − | − | + |
| Mycobacterium petroleophilum | 3655 | − | − | + |
| Mycobacterium porferae | 3657 | − | − | + |
| (pending) | 3534 | − | − | + |
| (pending) | 3558 | − | − | + |
| Rhodococcus | 3563 | − | − | ++ |

*Inclusivity data was determined after four hours exposure and exclusivity was determined after overnight exposures.
**Each organism is represented by either 100 ng of CsTFA purified RNA or 200 ng of PCR amplified DNA.
***++++ = positive level of hybridization, + = barely detectable and − = zero.

TABLE 3d

DOT BLOT HYBRIDIZATION OF 23S rRNA-TARGETED
MYCOBACTERIUM KANSASII PROBES

| Genus species | strain | PROBE HYBRIDIZATION | | | | | | |
|---|---|---|---|---|---|---|---|---|
| | | 2382 | 2388 | 2384 | 2389 | 2383 | 2390 | 2393 |
| *Mycobacterium tuberculosis* Rv37 | ATCC25618 | +++ | – | +++ | – | – | ++++ | ++++ |
| *Mycobacterium tuberculosis* Ra37 | 2487 | +++ | – | +++ | – | – | ++ | ++ |
| *Mycobacterium tuberculosis* complex | 3526 | + | – | ++ | – | – | ++++ | ++++ |
| *Mycobacterium tuberculosis* complex | 3528 | + | – | ++ | – | – | ++++ | ++++ |
| *Mycobacterium tuberculosis* complex | 3531 | +++ | – | ++ | – | – | ++++ | +++ |
| *Mycobacterium tuberculosis* complex | 3533 | +++ | – | +++ | – | – | ++++ | ++++ |
| *Mycobacterium tuberculosis* complex | 3535 | + | – | ++ | – | – | +++ | ++++ |
| *Mycobacterium tuberculosis* complex | 3536 | ++ | – | +++ | – | – | ++++ | ++++ |
| *Mycobacterium tuberculosis* complex | 3538 | ++ | – | +++ | – | – | ++++ | ++++ |
| *Mycobacterium tuberculosis* complex | 3539 | ++ | – | ++ | – | – | +++ | ++++ |
| *Mycobacterium tuberculosis* complex | 3540 | ++ | – | +++ | – | – | ++++ | ++++ |
| *Mycobacterium tuberculosis* complex | 3544 | ++ | – | +++ | – | – | ++++ | ++++ |
| *Mycobacterium tuberculosis* complex | 3545 | ++ | – | + | – | – | ++++ | ++++ |
| *Mycobacterium tuberculosis* complex | 3547 | + | – | + | – | – | ++++ | ++++ |
| *Mycobacterium tuberculosis* complex | 3548 | + | – | + | – | – | ++++ | ++++ |
| *Mycobacterium tuberculosis* complex | 3549 | + | – | + | – | – | ++++ | ++++ |
| *Mycobacterium tuberculosis* complex | 3552 | ++++ | – | +++ | – | – | ++++ | ++++ |
| *Mycobacterium tuberculosis* complex | 3553 | ++++ | – | +++ | – | – | ++++ | ++++ |
| *Mycobacterium tuberculosis* complex | 3554 | ++++ | + | +++ | – | – | ++++ | ++++ |
| *Mycobacterium africanum* | 3468 | ++++ | – | +++ | – | – | ++++ | + |
| *Mycobacterium asianticum* | 3507 | – | ++++ | +++ | – | – | ++++ | – |
| *Mycobacterium avium* | 3246 | ++ | ++++ | +++ | – | – | +++ | – |
| *Mycobacterium avium* | 3532 | + | + | ++ | – | – | ++++ | – |
| *Mycobacterium avium* | 3542 | ++ | +++ | +++ | – | – | ++++ | – |
| *Mycobacterium avium* | 3555 | +++ | +++ | +++ | – | – | ++ | – |
| *Mycobacterium avium* | 3559 | ++ | +++ | +++ | – | – | ++++ | – |
| *Mycobacterium avium* | 3561 | ++ | +++ | +++ | – | – | +++ | – |
| *Mycobacterium avium* | 3562 | ++ | + | +++ | – | – | +++ | – |
| *Mycobacterium avium* type 4 | | ++ | +++ | +++ | – | – | ++ | – |
| *Mycobacterium avium* 1 | | + | ND | ++++ | ND | ND | ND | – |
| *Mycobacterium avium* 2 | | + | ND | ++++ | ND | ND | ND | – |
| *Mycobacterium avium* 3 | | + | ND | ++++ | ND | ND | ND | – |
| *Mycobacterium avium* 4 | | + | ND | ++++ | ND | ND | ND | – |
| *Mycobacterium avium* 5 | | ++ | ND | ++++ | ND | ND | ND | – |
| *Mycobacterium avium* 6 | | + | ND | + | ND | ND | ND | – |
| *Mycobacterium avium* 8 | | ++ | ND | + | ND | ND | ND | – |
| *Mycobacterium avium* 9 | | + | ND | + | ND | ND | ND | – |
| *Mycobacterium avium* 10 | | ++ | ND | + | ND | ND | ND | – |
| *Mycobacterium avium* 12 | | ++ | ND | ++ | ND | ND | ND | – |
| *Mycobacterium avium* 13 | | ++ | ND | + | ND | ND | ND | – |
| *Mycobacterium avium* 15 | | ++ | ND | + | ND | ND | ND | – |
| *Mycobacterium bovis* | 3510 | +++ | – | +++ | – | – | ++++ | + |
| Mycobacterium BCG | | +++ | – | + | – | – | ++ | +++ |
| *Mycobacterium gordonae* | 3260 | – | ++++ | – | – | – | ++++ | + |
| *Mycobacterium intracellurarae* | 3422 | + | ++++ | +++ | – | – | ++ | – |
| *Mycobacterium intracellurarae* | 3425 | ++ | ++++ | +++ | – | – | ++ | – |
| *Mycobacterium intracellurarae* | 3436 | ++ | ++++ | +++ | – | – | ++++ | – |
| *Mycobacterium kansasii* | 3706 | ++++ | ++++ | ++++ | – | +++ | + | ++++ |
| *Mycobacterium kansasii* | | ++++ | +++ | ++++ | – | ++++ | +++ | ++++ |
| *Mycobacterium marinum* | 3508 | ++ | ++++ | +++ | – | + | ++++ | + |
| *Mycobacterium scrofulaceum* | 305 | +++ | ++++ | +++ | – | ++++ | +++ | +++ |
| Mycobacterium species | 3705 | – | ND | ++++ | ND | ND | ND | ++ |
| Mycobacterium species | 3743 | – | ND | – | ND | ND | ND | – |
| *Mycobacterium szulgai* | 3701 | – | ND | ++++ | ND | ND | ND | ++ |
| *Mycobacterium terrae* | 3247 | – | ++++ | – | – | +++ | – | ++ |
| *Mycobacterium triviale* | 3426 | – | ++++ | – | – | +++ | – | + |
| *Mycobacterium ulcerans* | 3744 | – | ND | – | ND | ND | ND | – |
| *Mycobacterium valentiae* | 3660 | – | ND | – | ND | ND | ND | – |
| *Mycobacterium agri* | 3503 | – | ++++ | – | ++ | + | ++ | + |
| *Mycobacterium aichiense* | 3501 | – | ++++ | – | ++++ | – | ++ | + |
| *Mycobacterium aurum* | 3505 | – | + | – | ++ | – | ++ | – |
| *Mycobacterium austroafricanum* | 3502 | – | ++++ | – | +++ | – | ++ | + |
| *Mycobacterium chelonei* | 3248 | – | ++++ | – | – | + | +++ | – |
| *Mycobacterium chelonei* | 3237 | – | +++ | – | – | – | + | – |
| *Mycobacterium chitae* | 3499 | – | ++++ | – | – | – | + | – |
| *Mycobacterium chubense* | 3497 | – | ++++ | – | +++ | – | ++++ | – |
| *Mycobacterium duvalli* | 3500 | – | + | – | ++ | – | – | – |
| *Mycobacterium diernhoferi* | 3504 | – | ++++ | – | ++++ | – | + | + |
| *Mycobacterium fallax* | 3658 | – | +++ | – | – | – | – | + |
| *Mycobacterium flavescens* | 3506 | – | ++ | – | – | + | ++ | – |
| *Mycobacterium fortuitum* | 3413 | – | ++++ | – | ++++ | +++ | – | – |
| *Mycobacterium fortuitum* | | – | +++ | – | ++++ | +++ | – | – |

TABLE 3d-continued

DOT BLOT HYBRIDIZATION OF 23S rRNA-TARGETED MYCOBACTERIUM KANSASII PROBES

| Genus species | strain | PROBE HYBRIDIZATION | | | | | | |
|---|---|---|---|---|---|---|---|---|
| | | 2382 | 2388 | 2384 | 2389 | 2383 | 2390 | 2393 |
| *Mycobacterium gadium* | 3420 | − | ++++ | − | ++ | +++ | + | − |
| *Mycobacterium gilvum* | 3419 | − | ++++ | − | ++++ | − | − | − |
| *Mycobacterium komossense* | 3661 | − | +++ | − | − | +++ | − | + |
| *Mycobacterium neoaurum* | 3642 | − | ++++ | − | ++++ | ++++ | ++ | − |
| *Mycobacterium obuense* | 3416 | − | ++++ | − | ++++ | − | ++++ | + |
| *Mycobacterium parafortuitum* | 3639 | − | ++++ | − | ++++ | − | + | − |
| *Mycobacterium phlei* | 3414 | − | ++++ | − | + | +++ | ++ | + |
| *Mycobacterium porcinum* | 3641 | − | ++++ | − | ++++ | ++++ | − | − |
| *Mycobacterium pulvaris* | 3644 | − | +++ | − | + | ++++ | − | − |
| *Mycobacterium rhodensiae* | 3412 | − | ++++ | − | + | − | ++++ | − |
| *Mycobacterium senegalense* | 3640 | − | ++++ | − | ++++ | − | − | − |
| *Mycobacterium smegmatis* | 306 | − | ++++ | − | ++++ | − | ++ | − |
| *Mycobacterium sphagni* | 3659 | − | +++ | − | + | − | ++ | − |
| *Mycobacterium thermoresistible* | 3645 | − | +++ | − | − | ++ | − | + |
| *Mycobacterium takainse* | 3638 | − | +++ | − | − | ++++ | − | − |
| *Mycobacterium vaccae* | 3637 | − | ++ | − | ++++ | − | − | − |
| *Mycobacterium acapulensis* | 3415 | − | ++++ | − | +++ | +++ | ++ | + |
| *Mycobacterium engbaekii* | 3509 | − | ++++ | − | − | ++ | − | − |
| *Mycobacterium gallinarum* | 3498 | − | ++++ | − | + | − | ++ | − |
| *Mycobacterium lactis* | 3703 | − | ++++ | − | − | +++ | − | + |
| *Mycobacterium moriokaense* | 3656 | − | +++ | − | + | + | ++ | − |
| *Mycobacterium petroleophilum* | 3655 | − | +++ | − | + | − | ++ | − |
| *Mycobacterium porferae* | 3657 | − | +++ | − | + | + | + | − |
| (pending) | 3534 | − | +++ | − | ++++ | +++ | − | − |
| (pending) | 3558 | − | + | − | +++ | ++++ | − | − |
| Rhodococcus | 3563 | − | + | − | − | + | − | − |

*Inclusivity data was determined after four hours exposure and exclusivity was determined after overnight exposures.
**Each organism is represented by either 100 ng of CsTFA purified RNA or 200 ng of PCR amplified DNA.
***++++ = positive level of hybridization, + = barely detectable and − = zero.

TABLE 3e

DOT BLOT HYBRIDIZATION to 23S rRNA-TARGETED *MYCOBACTERIUM FORTUITUM* PROBES

| Genus species | strain | PROBE HYBRIDIZATION | | | | | | | | | |
|---|---|---|---|---|---|---|---|---|---|---|---|
| | | 2373 | 2380 | 2376 | 2379 | 2365 | 2375 | 2378 | 2377 | 2374 | 1660 |
| *Mycobacterium tuberculosis* Rv37 | ATCC25618 | − | − | − | − | − | − | − | − | − | ++++ |
| *Mycobacterium tuberculosis* Ra37 | 2487 | − | − | − | − | − | − | − | − | − | ++++ |
| *Mycobacterium tuberculosis* complex | 3526 | − | − | − | − | − | − | − | − | − | +++ |
| *Mycobacterium tuberculosis* complex | 3528 | − | − | − | − | − | − | − | − | − | +++ |
| *Mycobacterium tuberculosis* complex | 3531 | − | − | − | − | − | − | − | − | − | +++ |
| *Mycobacterium tuberculosis* complex | 3533 | − | − | − | − | − | − | − | − | − | ++++ |
| *Mycobacterium tuberculosis* complex | 3535 | − | − | − | − | − | − | − | − | − | +++ |
| *Mycobacterium tuberculosis* complex | 3536 | − | − | − | − | − | − | − | − | − | +++ |
| *Mycobacterium tuberculosis* complex | 3538 | − | − | − | − | − | − | − | − | − | ++ |
| *Mycobacterium tuberculosis* complex | 3539 | − | − | − | − | − | − | − | − | − | +++ |
| *Mycobacterium tuberculosis* complex | 3544 | − | − | − | − | − | − | − | − | − | +++ |
| *Mycobacterium tuberculosis* complex | 3545 | − | − | − | − | − | − | − | − | − | ++++ |
| *Mycobacterium tuberculosis* complex | 3547 | − | − | − | − | − | − | − | − | − | ++++ |
| *Mycobacterium tuberculosis* complex | 3548 | − | − | − | − | − | − | − | − | − | ++++ |
| *Mycobacterium tuberculosis* complex | 3549 | − | − | − | − | − | − | − | − | − | ++++ |
| *Mycobacterium tuberculosis* complex | 3552 | − | − | − | − | − | − | − | − | − | +++ |
| *Mycobacterium tuberculosis* complex | 3553 | − | − | − | − | − | − | − | − | − | +++ |
| *Mycobacterium tuberculosis* complex | 3554 | − | − | − | − | − | − | − | − | − | +++ |
| *Mycobacterium africanum* | 3468 | ++ | − | − | − | − | − | − | − | − | +++ |
| *Mycobacterium asiaticum* | 3057 | ++ | − | − | − | +++ | − | − | − | − | ++++ |
| *Mycobacterium avium* | 3246 | − | − | − | − | − | − | − | − | − | ++++ |
| *Mycobacterium avium* | 3532 | − | − | − | − | − | − | − | − | − | +++ |
| *Mycobacterium avium* | 3542 | − | − | − | − | − | − | − | − | − | ++++ |
| *Mycobacterium avium* | 3555 | − | − | − | − | − | − | − | − | − | +++ |
| *Mycobacterium avium* | 3559 | − | − | − | − | − | − | − | − | − | +++ |
| *Mycobacterium avium* | 3561 | − | − | − | − | − | − | − | − | − | +++ |
| *Mycobacterium avium* | 3562 | − | − | − | − | − | − | − | − | − | +++ |
| *Mycobacterium avium* type 4 | | − | − | − | − | − | − | − | − | − | ++ |
| *Mycobacterium avium* 1 | | ND | − | − | − | ND | ND | − | − | − | ++++ |
| *Mycobacterium avium* 2 | | ND | − | − | − | ND | ND | − | − | − | ++++ |
| *Mycobacterium avium* 3 | | ND | − | − | − | ND | ND | − | − | − | ++++ |
| *Mycobacterium avium* 4 | | ND | − | − | − | ND | ND | − | − | − | ++++ |

TABLE 3e-continued

DOT BLOT HYBRIDIZATION to 23S rRNA-TARGETED *MYCOBACTERIUM FORTUITUM* PROBES

| Genus species | strain | PROBE HYBRIDIZATION | | | | | | | | | |
|---|---|---|---|---|---|---|---|---|---|---|---|
| | | 2373 | 2380 | 2376 | 2379 | 2365 | 2375 | 2378 | 2377 | 2374 | 1660 |
| *Mycobacterium avium* 5 | | ND | − | − | − | ND | ND | − | − | − | ++++ |
| *Mycobacterium avium* 6 | | ND | − | − | − | ND | ND | − | − | − | ++++ |
| *Mycobacterium avium* 8 | | ND | − | − | − | ND | ND | − | − | − | ++++ |
| *Mycobacterium avium* 9 | | ND | − | − | − | ND | ND | − | − | − | ++++ |
| *Mycobacterium avium* 10 | | ND | − | − | − | ND | ND | − | − | − | ++++ |
| *Mycobacterium avium* 12 | | ND | − | − | − | ND | ND | − | − | − | ++++ |
| *Mycobacterium avium* 13 | | ND | − | − | − | ND | ND | − | − | − | ++++ |
| *Mycobacterium avium* 15 | | ND | − | − | − | ND | ND | − | − | − | ++++ |
| *Mycobacterium bovis* | 3510 | − | − | − | − | − | − | − | − | − | ++++ |
| *Mycobacterium bovis* BCG | | − | − | − | − | − | − | − | − | − | + |
| *Mycobacterium gordonae* | 3260 | + | − | − | − | − | − | − | − | − | ++++ |
| *Mycobacterium intracellulare* | 3422 | − | − | − | − | − | − | − | − | − | +++ |
| *Mycobacterium intracellulare* | 3425 | − | − | − | − | − | − | − | − | − | +++ |
| *Mycobacterium intracellulare* | 3426 | − | − | − | − | − | − | − | − | − | ++++ |
| *Mycobacterium kansasii* | 3706 | − | − | − | − | − | − | − | − | − | ++++ |
| *Mycobacterium kansasii* | | − | − | − | − | − | − | − | − | − | ++++ |
| *Mycobacterium marinum* | 3508 | − | − | − | − | − | − | − | − | − | +++ |
| *Mycobacterium scrofulaceum* | 305 | − | − | − | − | − | − | − | − | − | ++++ |
| Mycobacterium species | 3705 | ND | − | − | − | ND | ND | − | − | − | ++++ |
| Mycobacterium species | 3743 | ND | − | − | − | ND | ND | − | − | − | ++++ |
| *Mycobacterium szulgai* | 3701 | ND | − | − | − | ND | ND | − | − | − | ++++ |
| *Mycobacterium terrae* | 3247 | +++ | − | − | − | − | − | + | − | − | ++++ |
| *Mycobacterium triviale* | 3426 | − | − | − | + | + | − | − | − | − | +++ |
| *Mycobacterium ulcerans* | 3744 | ND | − | − | − | ND | ND | − | − | − | +++ |
| *Mycobacterium valentiae* | 3660 | ND | − | + | ++++ | ND | ND | − | − | − | ++++ |
| *Mycobacterium agri* | 3503 | ++ | − | − | +++ | − | ++ | − | − | − | +++ |
| *Mycobacterium aichiense* | 3501 | ++ | − | − | ++++ | + | − | − | + | − | +++ |
| *Mycobacterium aurum* | 3505 | ++ | − | − | +++ | − | − | − | + | − | +++ |
| *Mycobacterium chelonei* | 3248 | +++ | − | − | − | +++ | − | − | − | ++++ | ++++ |
| *Mycobacterium chelonei* | 3537 | ++ | − | − | − | ++ | − | − | − | ++ | ++ |
| *Mycobacterium chitae* | 3499 | +++ | − | − | − | + | ++++ | − | − | ++ | ++++ |
| *Mycobacterium chubuense* | 3497 | +++ | − | − | ++++ | − | − | − | − | ++ | +++ |
| *Mycobacterium diernhoferi* | 3504 | ++ | − | ++++ | +++ | − | − | − | + | − | +++ |
| *Mycobacterium duvalii* | 3500 | +++ | − | +++ | ++++ | − | − | − | − | − | ++++ |
| *Mycobacterium fallax* | 3658 | ++ | − | + | − | ++ | + | − | − | − | ++++ |
| *Mycobacterium flavescens* | 3506 | ++ | − | +++ | + | ++ | ++++ | + | + | + | +++ |
| *Mycobacterium fortuitum* | 3413 | +++ | + | ++++ | + | ++++ | ++++ | + | ++ | ++++ | +++ |
| *Mycobacterium fortuitum* | | +++ | ++ | +++ | ++++ | + | ++++ | ++++ | ++++ | + | +++ |
| *Mycobacterium gadium* | 3420 | ++ | − | − | ++ | + | ++++ | +++ | − | − | ++++ |
| *Mycobacterium gilvum* | 3419 | ++ | − | − | ++++ | − | − | − | − | ++ | ++++ |
| *Mycobacterium komossense* | 3661 | + | − | − | − | − | + | − | − | − | +++ |
| *Mycobacterium neoaurum* | 3642 | +++ | − | +++ | ++++ | − | − | + | + | +++ | +++ |
| *Mycobacterium obuense* | 3416 | ++++ | − | − | ++++ | − | − | − | − | ++ | ++++ |
| *Mycobacterium parafortuitum* | 3639 | + | − | − | +++ | ++ | +++ | − | − | − | +++ |
| *Mycobacterium phlei* | 3414 | +++ | − | − | ++ | + | − | − | + | − | +++ |
| *Mycobacterium porcinum* | 3641 | +++ | + | ++++ | ++++ | ++++ | +++ | +++ | + | − | +++ |
| *Mycobacterium pulveris* | 3644 | ++ | − | − | + | ++ | +++ | + | − | ++++ | +++ |
| *Mycobacterium rhodesiae* | 3412 | ++++ | − | − | ++ | − | − | − | − | − | +++ |
| *Mycobacterium senegalense* | 3640 | +++ | + | − | +++ | ++ | +++ | − | − | − | +++ |
| *Mycobacterium smegmatis* | 306 | +++ | + | ++ | ++++ | + | +++ | − | − | − | ++++ |
| *Mycobacterium sphagni* | 3659 | +++ | − | − | + | − | + | − | − | − | +++ |
| *Mycobacterium thermoresistable* | 3645 | + | − | − | − | ++ | + | + | − | − | +++ |
| *Mycobacterium takaiense* | 3638 | +++ | − | − | − | − | − | − | − | ++++ | ++++ |
| *Mycobacterium vaccae* | 3637 | +++ | − | − | ++++ | − | − | − | − | ++++ | ++++ |
| *Mycobacterium acapulensis* | 3415 | ++++ | − | + | ++ | + | +++ | − | − | − | ++++ |
| *Mycobacterium gallinarum* | 3498 | +++ | − | − | − | − | − | − | − | − | ++++ |
| *Mycobacterium engbaekii* | 3509 | +++ | − | − | ++++ | − | − | − | − | ++++ | +++ |
| *Mycobacterium lactis* | 3703 | ++++ | − | − | − | − | − | − | − | − | +++ |
| *Mycobacterium moriokaense* | 3656 | +++ | − | +++ | +++ | +++ | + | − | − | − | +++ |
| *Mycobacterium petroleophilum* | 3655 | ++++ | − | +++ | ++ | − | − | + | − | − | +++ |
| *Mycobacterium porferae* | 3657 | +++ | − | − | + | − | + | − | − | +++ | +++ |
| (pending) | 3534 | ++++ | ++++ | +++ | ++ | ++++ | ++ | + | − | ++++ | ++++ |
| (pending) | 3558 | ++++ | ++++ | ++++ | ++++ | ++++ | ++++ | ++++ | − | ++ | ++++ |

*Inclusivity data was determined after four hours exposure and exclusivity was determined after overnight exposures.
**Each organism is represented by either 100 ng of CsTFA purified RNA or 200 ng of PCR amplified DNA.
*** ++++ = positive level of hybridization, + = barely detectable and − = zero.

TABLE 4a

DOT BLOT HYBRIDIZATION OF 16S rRNA-TARGETED MYCOBACTERIUM PROBES

| Genus Species | Strain GT # | PROBE BEHAVIOUR 2233 | 2240 | 2215 | 2213 | 2236 |
|---|---|---|---|---|---|---|
| *Citrobacter freundii* | 0687 | − | − | − | − | − |
| *Escherichia coli* | 1665 | − | − | − | − | − |
| *Haemophilus influenza* | 33391 | − | − | − | − | − |
| *Klebsiella pneumoniae* | 1500 | − | − | − | − | − |
| *Bordetella pertussis* | 3513 | − | − | − | − | − |
| *Agrobacterium tumefaciens* | 2021 | − | − | − | − | − |
| *Desulfovibrio desulfuricans* | ATCC7757 | − | − | − | − | − |
| *Campylobacter jejuni* | 0022 | − | − | − | − | − |
| *Bacillus subtilis* | 0804 | − | − | − | − | − |
| *Clostridium perfringens* | ATCC13124 | − | − | − | − | − |
| *Mycoplasma pneumonia* | FH | − | − | − | − | − |
| *Staphylococcus aureus* | 1711 | − | − | − | − | − |
| *Streptococcus faecalis* | 0406 | − | − | − | − | − |
| *Streptococcus pneumonia* | 0408 | − | − | − | − | − |
| *Streptococcus salivarius* | 0410 | − | − | − | − | − |
| *Actinomyces israelii* | 0005 | − | − | − | − | − |
| *Actinomyces odontolyticulus* | 2195 | − | − | − | − | − |
| *Arthrobacter globiformis* | 2117 | ++++ | − | − | − | − |
| 'Bifidobacterium dentium | 0012 | − | − | − | − | − |
| *Corynebacterium genitalium* | 0045 | ++++ | − | − | − | − |
| *Corynebacterium glutamicum* | 2120 | ++++ | − | − | − | − |
| *Corynebacterium pseudodiphtheriticum* | 2119 | − | − | − | − | − |
| *Corynebacterium pseudotuberculosis* | 2122 | − | − | − | − | − |
| *Corynebacterium pyrogenes* | 2121 | +++ | − | − | − | − |
| *Corynebacterium xerosis* | 0046 | ++++ | +++ | − | − | − |
| *Corynebacterium diphtheriae* | 3511 | ++++ | − | − | − | − |
| *Corynebacterium diphtheriae* | 3512 | ++++ | − | − | − | − |
| 'Jonesia denitrificans | 0666 | − | − | − | − | − |
| *Micrococcus conoglomeratus* | ATCC0401 | ++++ | − | − | − | − |
| *Micrococcus luteus* | ATCC0381 | ++++ | − | − | − | − |
| Mycobacterium species | 0298 | ++++ | − | − | − | − |
| *Nocardia asteroides* | 2192 | − | − | − | − | − |
| *Nocardia albus* | DSM43109 | − | − | − | − | − |
| *Nocardia dassonvillei* | DMS43235 | − | − | − | + | +++ |
| *Pimelobacter simplex* | DMS08929 | − | +++ | − | − | − |
| *Propionobacterium acnes* | 0363 | − | − | − | − | − |
| *Propionobacterium thoenii* | DMS20276 | ++ | − | − | − | − |
| *Rhodococcus equi* | 0665 | ++++ | − | − | − | − |
| *Rhodococcus rhodochrous* | | ++++ | − | − | − | − |
| *Rhodococcus bronchialis* | 3473 | ++++ | − | − | − | − |
| *Rhodococcus sputi* | 3474 | ++++ | − | − | − | − |
| *Rhodococcus obuensis* | 3475 | ++++ | − | − | − | − |
| *Rhodococcus aurantiacus* | 3476 | ++++ | − | − | − | − |
| *Rhodococcus erythopolis* | 3523 | ++++ | − | − | − | − |
| *Rhodococcus fascians* | 3524 | ++++ | − | − | − | − |
| *Rhodococcus rhodochrous* | 3589 | ++++ | − | − | − | − |
| *Rhodococcus ketoglutanicum* | 3588 | ++++ | − | − | − | − |
| *Streptomyces griseus* | 3590 | − | − | − | − | − |
| *Streptomyces mutans* | 0412 | − | − | − | − | − |
| *Streptomyces mitis* | 3490 | − | − | − | − | − |
| *Bifidobacterium dentium* | 0571 | − | − | − | − | − |
| *K rhinoscleromitis* | 1881 | − | − | − | − | − |
| *Fusobacterium necrophorum* | 0238 | − | − | − | − | − |
| *Spirochaeta aurantia* | | + | − | − | − | − |
| *Bacteroides fragilis* | ATCC29771 | − | − | − | − | − |
| *Chlorobium limicola* | | − | − | − | − | − |
| *Chloroflexus aurantiacus* | Y0400 | − | − | − | − | − |
| *Deinococcuc radiodurans* | 2608 | − | − | − | − | − |
| Normal stool | | − | − | − | − | − |
| Human T-cells | | − | − | − | − | − |
| *Candida albicans* | | − | − | − | − | − |
| *Crytococcus neoformans* | | − | − | − | − | − |
| Wheat germ | | − | − | − | − | − |

| Genus Species | Strain GT # | PROBE BEHAVIOUR 2155 | 2156 | 2235 | 2257 | 2248 |
|---|---|---|---|---|---|---|
| *Citrobacter freundii* | 0687 | − | − | − | − | − |
| *Escherichia coli* | 1665 | − | + | − | − | − |
| *Haemophilus influenza* | 33391 | − | + | − | − | − |
| *Klebsiella pneumoniae* | 1500 | − | + | − | − | − |
| *Bordetella pertussis* | 3513 | − | + | − | − | − |

TABLE 4a-continued

DOT BLOT HYBRIDIZATION OF 16S rRNA-TARGETED MYCOBACTERIUM PROBES

| Genus Species | Strain GT # | | | | | |
|---|---|---|---|---|---|---|
| Agrobacterium tumefaciens | 2021 | − | + | − | − | − |
| Desulfovibrio desulfuricans | ATCC7757 | − | + | − | − | − |
| Campylobacter jejuni | 0022 | − | − | − | − | − |
| Bacillus subtilis | 0804 | − | − | − | − | − |
| Clostridium perfringens | ATCC13124 | − | − | − | − | − |
| Mycoplasma pneumonia | FH | − | − | − | − | − |
| Staphylococcus aureus | 1711 | − | + | − | − | − |
| Streptococcus faecalis | 0406 | − | + | − | − | − |
| Streptococcus pneumonia | 0408 | − | − | − | − | − |
| Streptococcus salivarius | 0410 | − | − | − | − | − |
| Actinomyces israelii | 0005 | − | − | − | − | − |
| Actinomyces odontolyticulus | 2195 | − | ++ | − | − | − |
| Arthrobacter globifiormis | 2117 | − | ++++ | − | − | − |
| 'Bifidobacterium dentium | 0012 | − | ++++ | − | − | − |
| Corynebacterium genitalium | 0045 | + | ++++ | − | − | − |
| Corynebacterium glutamicum | 2120 | ++ | ++++ | − | − | − |
| Corynebacterium pseudodiphtheriticum | 2119 | − | + | − | − | − |
| Corynebacterium pseudotuberculosis | 2122 | − | ++ | − | − | − |
| Corynebacterium pyrogenes | 2121 | − | − | − | − | − |
| Corynebacterium xerosis | 0046 | + | ++++ | − | − | − |
| Corynebacterium diphtheriae | 3511 | ++ | ++++ | − | − | − |
| Corynebacterium diphtheriae | 3512 | ++ | ++++ | − | − | − |
| 'Jonesia denitrificans | 0666 | − | + | − | − | − |
| Micrococcus conoglomeratus | ATCC0401 | − | ++++ | − | − | − |
| Micrococcus luteus | ATCC0381 | − | ++++ | − | − | − |
| Mycobacterium species | 0298 | − | ++++ | − | − | − |
| Nocardia asteroides | 2192 | − | − | − | − | − |
| Nocardia albus | DSM43109 | − | ++ | − | − | − |
| Nocardia dassonvillei | DMS43235 | − | +++ | − | − | − |
| Pimelobacter simplex | DMS08929 | − | +++ | − | − | + |
| Propionobacterium acnes | 0363 | − | + | − | − | − |
| Propionobacterium thoenii | DMS20276 | − | + | − | − | − |
| Rhodococcus equi | 0665 | − | ++++ | − | − | − |
| Rhodococcus rhodochrous | | − | ++++ | − | − | + |
| Rhodococcus bronchialis | 3473 | − | ++++ | − | − | + |
| Rhodococcus sputi | 3474 | − | ++++ | − | − | + |
| Rhodococcus obuensis | 3475 | − | ++++ | − | − | + |
| Rhodococcus aurantiacus | 3476 | − | ++++ | − | − | − |
| Rhodococcus erythopolis | 3523 | − | ++++ | − | − | − |
| Rhodococcus fascians | 3524 | − | ++++ | − | − | − |
| Rhodococcus rhodochrous | 3589 | − | ++++ | − | − | − |
| Rhodococcus ketoglutanicum | 3588 | − | ++++ | − | − | − |
| Streptomyces griseus | 3590 | − | + | − | − | − |
| Streptomyces mutans | 0412 | − | + | − | − | − |
| Streptomyces mitis | 3490 | − | + | − | − | − |
| Bifidobacterium dentium | 0571 | − | +++ | − | − | − |
| K rhinoscleromitis | 1881 | − | + | − | − | − |
| Fusobacterium necrophorum | 0238 | − | − | − | − | − |
| Spirochaeta aurantia | | − | + | − | − | − |
| Bacteroides fragilis | ATCC29771 | − | − | − | − | − |
| Chlorobium limicola | | − | + | − | − | − |
| Chloroflexus aurantiacus | Y0400 | − | − | − | − | − |
| Deinococcuc radiodurans | 2608 | − | + | − | − | − |
| Normal stool | | − | + | − | − | − |
| Human T-cells | | − | + | − | − | − |
| Candida albicans | | − | − | − | − | − |
| Crytococcus neoformans | | − | − | − | − | − |
| Wheat germ | | − | − | − | − | − |

| | Strain | PROBE BEHAVIOUR | | |
|---|---|---|---|---|
| Genus Species | GT # | 2214 | 2234 | 2247 |
| Citrobacter freundii | 0687 | − | − | − |
| Escherichia coli | 1665 | − | − | − |
| Haemophilus influenza | 33391 | − | − | − |
| Klebsiella pneumoniae | 1500 | − | − | − |
| Bordetella pertussis | 3513 | − | + | − |
| Agrobacterium tumefaciens | 2021 | − | − | − |
| Desulfovibrio desulfuricans | ATCC7757 | − | − | − |
| Campylobacter jejuni | 0022 | − | − | − |
| Bacillus subtilis | 0804 | − | − | − |
| Clostridium perfringens | ATCC13124 | − | − | − |
| Mycoplasma pneumonia | FH | − | − | − |
| Staphylococcus aureus | 1711 | − | − | − |
| Streptococcus faecalis | 0406 | − | − | − |
| Streptococcus pneumonia | 0408 | − | − | − |

TABLE 4a-continued

DOT BLOT HYBRIDIZATION OF 16S rRNA-TARGETED MYCOBACTERIUM PROBES

| | | | | |
|---|---|---|---|---|
| *Streptococcus salivarius* | 0410 | − | − | − |
| *Actinomyces israelii* | 0005 | − | − | − |
| *Actinomyces odontolyticulus* | 2195 | − | ++++ | − |
| *Arthrobacter globiformis* | 2117 | − | ++++ | ++++ |
| 'Bifidobacterium dentium | 0012 | − | +++ | − |
| *Corynebacterium genitalium* | 0045 | − | ++++ | − |
| *Corynebacterium glutamicum* | 2120 | − | − | − |
| *Corynebacterium pseudodiphtheriticum* | 2119 | − | − | − |
| *Corynebacterium pseudotuberculosis* | 2122 | − | ++ | − |
| *Corynebacterium pyrogenes* | 2121 | − | +++ | − |
| *Corynebacterium xerosis* | 0046 | − | ++++ | − |
| *Corynebacterium diphtheriae* | 3511 | − | ++++ | − |
| *Corynebacterium diphtheriae* | 3512 | − | ++++ | − |
| 'Jonesia denitrificans | 0666 | − | ++++ | − |
| *Micrococcus conoglomeratus* | ATCC0401 | − | ++++ | − |
| *Micrococcus luteus* | ATCC0381 | − | ++++ | − |
| Mycobacterium species | 0298 | − | ++++ | − |
| *Nocardia asteroides* | 2192 | − | − | − |
| *Nocardia albus* | DSM43109 | − | − | − |
| *Nocardia dassonvillei* | DMS43235 | − | ++++ | − |
| *Pimelobacter simplex* | DMS08929 | − | − | ++++ |
| *Propionobacterium acnes* | 0363 | − | ++++ | − |
| *Propionobacterium thoenii* | DMS20276 | − | − | − |
| *Rhodococcus equi* | 0665 | − | ++++ | ++++ |
| *Rhodococcus rhodochrous* | | − | − | ++++ |
| *Rhodococcus bronchialis* | 3473 | ++++ | − | ++++ |
| *Rhodococcus sputi* | 3474 | − | − | ++++ |
| *Rhodococcus obuensis* | 3475 | − | − | ++++ |
| *Rhodococcus aurantiacus* | 3476 | − | +++ | − |
| *Rhodococcus erythopolis* | 3523 | − | +++ | − |
| *Rhodococcus fascians* | 3524 | − | ++++ | − |
| *Rhodococcus rhodochrous* | 3589 | − | ++++ | − |
| *Rhodococcus ketoglutanicum* | 3588 | − | ++++ | − |
| *Streptomyces griseus* | 3590 | − | ++ | − |
| *Streptomyces mutans* | 0412 | − | − | − |
| *Streptomyces mitis* | 3490 | − | − | − |
| *Bifidobacterium dentium* | 0571 | − | +++ | − |
| *K rhinoscleromitis* | 1881 | − | − | − |
| *Fusobacterium necrophorum* | 0238 | − | − | − |
| *Spirochaeta aurantia* | | − | − | − |
| *Bacteroides fragilis* | ATCC29771 | − | − | − |
| *Chlorobium limicola* | | − | − | − |
| *Chloroflexus aurantiacus* | Y0400 | − | − | − |
| *Deinococcus radiodurans* | 2608 | − | − | − |
| Normal stool | | − | − | − |
| Human T-cells | | − | − | − |
| *Candida albicans* | | − | − | − |
| *Crytococcus neoformans* | | − | − | − |
| Wheat germ | | − | − | − |

*Inclusivity data was determined after four hours exposure and exclusivity data was determined after overnight exposures.
**Each organism is represented by either 100 ng of CsTFA purified RNA.
*** ++++ = positive level of hybridization, + = barely detectable and − = zero.

TABLE 4b

DOT BLOT HYBRIDIZATION OF 23S rRNA-TARGETED MYCOBACTERIUM TUBERCULOSIS COMPLEX PROBES

| | | PROBE BEHAVIOUR | | | | | | |
|---|---|---|---|---|---|---|---|---|
| Genus Species | Strain GT # | 2364 | 2362 | 2366 | 2371 | 2368 | 2369 | 2372 |
| *Citrobacter freundii* | 0687 | − | − | − | − | − | − | − |
| *Escherichia coli* | 1665 | − | − | − | − | − | − | − |
| *Haemophilus influenza* | 33391 | − | − | − | − | − | − | − |
| *Klebsiella pneumonia* | 1500 | − | − | − | − | − | − | − |
| *Bordetella pertussis* | 3513 | − | − | − | − | − | − | − |
| *Desulfovibrio desulfuricans* | ATCC7757 | − | − | − | − | − | − | − |
| *Campylobacter jejuni* | 0022 | − | − | − | − | − | − | − |
| *Bacillus subtilis* | 0804 | − | − | − | − | − | − | − |
| *Clostridium perfringens* | ATCC13124 | − | − | − | − | − | − | − |
| *Mycoplasma pneumonia* | FH | − | − | − | − | − | − | − |
| *Staphylococcus aureus* | 1711 | − | − | − | − | − | − | − |
| *Streptococcus faecalis* | 0406 | − | − | − | − | − | − | − |

TABLE 4b-continued

DOT BLOT HYBRIDIZATION OF 23S
rRNA-TARGETED MYCOBACTERIUM TUBERCULOSIS COMPLEX PROBES

| Genus Species | Strain GT # | 2364 | 2362 | 2366 | 2371 | 2368 | 2369 | 2372 |
|---|---|---|---|---|---|---|---|---|
| *Streptococcus pneumonia* | 0408 | − | − | − | − | − | − | − |
| *Streptococcus salivarius* | 0410 | − | − | − | − | − | − | − |
| *Actinomyces israelii* | 0005 | − | − | − | − | − | − | − |
| *Actinomyces odontolyticulus* | 2195 | − | − | − | − | − | − | − |
| *Arthrobacter globifiormis* | 2117 | − | − | − | − | − | + | ++++ |
| *Bifidobacterium dentium* | 0012 | − | − | − | − | − | − | − |
| *Corynebacterium genitalium* | 0045 | + | − | − | − | − | − | ++++ |
| *Corynebacterium glutamicum* | 2120 | − | − | − | − | − | − | ++++ |
| *Corynebacterium pseudodiphtheriticum* | 2119 | − | − | − | − | − | − | − |
| *Corynebacterium pseudotuberculosis* | 2122 | − | − | − | − | − | − | − |
| *Corynebacterium pyogenes* | 2121 | − | − | − | − | − | − | ++++ |
| *Corynebacterium xerosis* | 0046 | + | − | − | − | − | + | ++++ |
| *Corynebacterium diphtheriae* | 3511 | + | − | − | − | − | − | ++++ |
| *Corynebacterium diphtheriae* | 3512 | + | − | − | − | − | − | ++++ |
| *Jonesia denitrificans* | 0666 | − | − | − | − | − | − | − |
| *Micrococcus conoglomeratus* | ATCC0401 | + | − | − | − | − | − | ++++ |
| *Micrococcus luteus* | ATCC0381 | − | − | − | − | − | − | ++++ |
| Mycobacterium species | 0298 | − | − | − | − | − | − | ++++ |
| *Nocardia asteroides* | 2192 | − | − | − | − | − | − | − |
| *Nocardia albus* | DSM43109 | − | − | − | − | − | − | − |
| *Nocardia dassonvillei* | DMS43235 | − | − | − | − | − | − | − |
| *Pimelobacter simplex* | DMS08929 | − | − | − | − | − | − | − |
| *Propionobacterium acnes* | 0363 | − | − | − | − | − | − | − |
| *Propionobacterium thoenii* | DMS20276 | − | − | − | − | − | − | − |
| *Rhodococcus equi* | 0665 | − | − | − | − | − | − | ++++ |
| *Rhodococcus rhodochrous* | | − | − | − | − | − | − | ++++ |
| *Rhodococcus bronchialis* | 3473 | − | − | − | − | − | − | ++++ |
| *Rhodococcus sputi* | 3474 | − | − | − | − | − | − | ++++ |
| *Rhodococcus obuensis* | 3475 | − | − | − | − | − | − | ++++ |
| *Rhodococcus aurantiacus* | 3476 | − | − | − | − | − | − | ++++ |
| *Rhodococcus erythopolis* | 3523 | − | − | − | − | − | − | ++++ |
| *Rhodococcus fascians* | 3524 | − | − | − | − | − | − | ++++ |
| *Rhodococcus rhodochrous* | 3589 | − | − | − | − | − | − | ++++ |
| *Rhodococcus ketoglutanicum* | 3588 | − | − | − | − | − | − | ++++ |
| *Streptomyces griseus* | 3590 | − | − | − | − | − | − | − |
| *Streptomyces mutans* | 0412 | − | − | − | − | − | − | − |
| *Streptomyces mitis* | 3490 | − | − | − | − | − | − | − |
| *Bifidobacterium dentium* | 0571 | − | − | − | − | − | − | − |
| *K rhinoscleromitis* | 1881 | − | − | − | − | − | − | − |
| *Fusobacterium necrophorum* | 0238 | − | − | − | − | − | − | − |
| *Spirochaeta aurantia* | | − | − | − | − | − | − | − |
| *Bacteroides fragilis* | ATCC29771 | − | − | − | − | − | − | − |
| *Chlorobium limicola* | | − | − | − | − | − | − | − |
| *Chloroflexus aurantiacus* | Y0400 | − | − | − | − | − | − | − |
| *Deinococcus radiodurans* | 2608 | − | − | − | − | − | − | − |
| Normal stool | | − | − | − | − | − | − | − |
| Human T-cells | | − | − | − | − | − | − | − |
| *Candida albicans* | | − | − | − | − | − | − | − |
| *Crytococcus neoformans* | | − | − | − | − | − | − | − |
| Wheat germ | | − | − | − | − | − | − | − |

*Inclusivity data was determined after four hour exposure and exclusivity data was determined after overnight exposure.
**Each organism is represented by either 100 ng of CsTFA purified RNA.
***++++ = positive level of hybridization; + = barely detectable and − = zero.

TABLE 4c

DOT BLOT HYBRIDIZATION OF 23S
rRNA-TARGETED MYCOBACTERIUM AVIUM COMPLEX PROBES

| Genus Species | Strain GT # | PROBE BEHAVIOUR | | |
|---|---|---|---|---|
| | | 2392 | 2425 | 2428 |
| *Citrobacter freundii* | 0687 | − | − | + |
| *Escherichia coli* | 1665 | − | − | ++ |
| *Haemophilus influenza* | 33391 | − | − | − |
| *Klebsiella pneumoniae* | 1500 | − | − | − |
| *Bordetella pertussis* | 3513 | − | − | − |
| *Agrobacterium tumefaciens* | 2021 | − | − | − |

TABLE 4c-continued

DOT BLOT HYBRIDIZATION OF 23S
rRNA-TARGETED MYCOBACTERIUM AVIUM COMPLEX PROBES

| Genus Species | Strain GT # | PROBE BEHAVIOUR | | |
|---|---|---|---|---|
| | | 2392 | 2425 | 2428 |
| *Desulfovibrio desulfuricans* | ATCC7757 | − | − | − |
| *Campylobacter jejuni* | 0022 | − | − | − |
| *Bacillus subtilis* | 0804 | − | − | − |
| *Clostridium perfringens* | ATCC13124 | − | − | − |
| *Mycoplasma pneumonia* | FH | − | − | − |
| *Staphylococcus aureus* | 1711 | − | − | − |
| *Streptococcus faecalis* | 0406 | − | − | − |
| *Streptococcus pneumonia* | 0408 | − | − | − |
| *Streptococcus salivarius* | 0410 | − | − | − |
| *Actinomyces israelii* | 0005 | − | − | − |
| *Actinomyces odontolyticulus* | 2195 | − | − | + |
| *Arthrobacter globiformis* | 2117 | − | − | ++++ |
| *Bifidobacterium dentium* | 0012 | − | − | − |
| *Corynebacterium genitalium* | 0045 | − | − | − |
| *Corynebacterium glutamicum* | 2120 | − | − | + |
| *Corynebacterium pseudodiphtheriticum* | 2119 | − | − | − |
| *Corynebacterium pseudotuberculosis* | 2122 | − | − | − |
| *Corynebacterium pyogenes* | 2121 | − | − | + |
| *Corynebacterium xerosis* | 0046 | − | − | + |
| *Corynebacterium diphtheriae* | 3511 | − | − | + |
| *Corynebacterium diphtheriae* | 3512 | − | − | + |
| *Jonesia denitrificans* | 0666 | − | − | +++ |
| *Micrococcus conoglomeratus* | ATCC0401 | − | − | + |
| *Micrococcus luteus* | ATCC0381 | − | − | + |
| *Mycobacterium species* | 0298 | − | − | + |
| *Nocardia asteroides* | 2192 | − | − | − |
| *Nocardia albus* | DSM43109 | − | − | + |
| *Nocardia dassonvillei* | DMS43235 | − | − | − |
| *Pimelobacter simplex* | DMS08929 | − | − | + |
| *Propionobacterium acnes* | 0363 | − | − | + |
| *Propionobacterium thoenii* | DMS20276 | − | − | + |
| *Rhodococcus equi* | 0665 | − | − | +++ |
| *Rhodococcus rhodochrous* | | − | − | + |
| *Rhodococcus bronchialis* | 3473 | − | − | + |
| *Rhodococcus sputi* | 3474 | − | − | ++ |
| *Rhodococcus obuensis* | 3475 | − | − | ++ |
| *Rhodococcus aurantiacus* | 3476 | − | − | +++ |
| *Rhodococcus erythopolis* | 3523 | − | − | ++ |
| *Rhodococcus fascians* | 3524 | − | − | ++ |
| *Rhodococcus rhodochrous* | 3589 | − | − | +++ |
| *Rhodococcus ketoglutanicum* | 3588 | − | − | ++ |
| *Streptomyces griseus* | 3590 | − | − | + |
| *Streptomyces mutans* | 0412 | − | − | − |
| *Streptomyces mitis* | 3490 | − | − | − |
| *Bifidobacterium dentium* | 0571 | − | − | − |
| *K rhinoscleromitis* | 1881 | − | − | + |
| *Fusobacterium necrophorum* | 0238 | − | − | − |
| *Spirochaeta aurantia* | | − | − | − |
| *Bacteroides fragilis* | ATCC29771 | − | − | − |
| *Chlorobium limicola* | | − | − | − |
| *Chloroflexus aurantiacus* | Y0400 | − | − | − |
| *Deinococcus radiodurans* | 2608 | − | − | − |
| Normal stool | | − | − | − |
| Human T-cells | | − | − | − |
| *Candida albicans* | | − | − | − |
| *Crytococcus neoformans* | | − | − | − |
| Wheat germ | | − | − | − |

*Inclusivity data was determined after four hour exposure and exclusivity data was determined after overnight exposure.
**Each organism is represented by either 100 ng of CsTFA purified RNA.
***++++ = positive level of hybridization; + = barely detectable and − = zero.

TABLE 4d

DOT BLOT HYBRIDIZATION OF 23S
rRNA-TARGETED MYCOBACTERIUM KANSASII PROBES

| Genus Species | Strain GT # | PROBE BEHAVIOUR | | | |
|---|---|---|---|---|---|
| | | 2382 | 2388 | 2384 | 2389 |
| *Citrobacter freundii* | 0687 | − | − | − | − |
| *Escherichia coli* | 1665 | − | − | − | − |
| *Haemophilus influenza* | 33391 | − | − | − | − |
| *Klebsiella pneumoniae* | 1500 | − | − | − | − |
| *Bordetella pertussis* | 3513 | − | − | − | − |
| *Agrobacterium tumefaciens* | 2021 | − | − | − | − |
| *Desulfovibrio desulfuricans* | ATCC7757 | − | − | − | − |
| *Campylobacter jejuni* | 0022 | − | − | − | − |
| *Bacillus subtilis* | 0804 | − | ++ | − | − |
| *Clostridium perfringens* | ATCC13124 | − | − | − | − |
| *Mycoplasma pneumonia* | FH | − | − | − | − |
| *Staphylococcus aureus* | 1711 | − | ++ | − | − |
| *Streptococcus faecalis* | 0406 | − | − | − | − |
| *Streptococcus pneumonia* | 0408 | − | − | − | − |
| *Streptococcus salivarius* | 0410 | − | − | − | − |
| *Actinomyces israelii* | 0005 | − | + | − | − |
| *Actinomyces odontolyticulus* | 2195 | − | ++ | − | + |
| *Arthrobacter globifiormis* | 2117 | − | − | − | − |
| *Bifidobacterium dentium* | 0012 | − | + | − | − |
| *Corynebacterium genitalium* | 0045 | − | ++ | − | − |
| *Corynebacterium glutamicum* | 2120 | − | + | − | + |
| *Corynebacterium pseudodiphtheriticum* | 2119 | − | ++ | − | − |
| *Corynebacterium pseudotuberculosis* | 2122 | − | + | − | − |
| *Corynebacterium pyogenes* | 2121 | − | +++ | − | − |
| *Corynebacterium xerosis* | 0046 | − | +++ | − | − |
| *Corynebacterium diphtheriae* | 3511 | − | − | − | − |
| *Corynebacterium diphtheriae* | 3512 | − | ++ | − | − |
| *Jonesia denitrificans* | 0666 | − | − | − | − |
| *Micrococcus conoglomeratus* | ATCC0401 | − | − | − | − |
| *Micrococcus luteus* | ATCC0381 | − | − | − | − |
| Mycobacterium species | 0298 | − | − | − | − |
| *Nocardia asteroides* | 2192 | − | − | − | − |
| *Nocardia albus* | DSM43109 | − | +++ | − | − |
| *Nocardia dassonvillei* | DMS43235 | − | − | − | − |
| Pimelobacter simplex | DMS08929 | − | +++ | − | − |
| *Propionobacterium acnes* | 0363 | − | ++ | − | − |
| *Propionobacterium thoenii* | DMS20276 | − | − | − | − |
| *Rhodococcus equi* | 0665 | − | +++ | − | − |
| *Rhodococcus rhodochrous* | | − | +++ | − | − |
| *Rhodococcus bronchialis* | 3473 | − | ++ | − | − |
| *Rhodococcus sputi* | 3474 | − | + | − | − |
| *Rhodococcus obuensis* | 3475 | − | + | − | − |
| *Rhodococcus aurantiacus* | 3476 | − | +++ | − | − |
| *Rhodococcus erythopolis* | 3523 | − | +++ | − | − |
| *Rhodococcus fascians* | 3524 | − | − | − | − |
| *Rhodococcus rhodochrous* | 3589 | − | ++++ | − | − |
| *Rhodococcus ketoglutanicum* | 3588 | − | − | − | − |
| *Streptomyces griseus* | 3590 | − | − | − | − |
| *Streptomyces mutans* | 0412 | − | − | − | − |
| *Streptomyces mitis* | 3490 | − | − | − | − |
| *Bifidobacterium dentium* | 0571 | − | − | − | − |
| *K rhinoscleromitis* | 1881 | − | − | − | − |
| *Fusobacterium necrophorum* | 0238 | − | − | − | − |
| *Spirochaeta aurantia* | | − | − | − | − |
| *Bacteroides fragilis* | ATCC29771 | − | − | − | − |
| *Chlorobium limicola* | | − | − | − | − |
| *Chloroflexus aurantiacus* | Y0400 | − | − | − | − |
| *Deinococcus radiodurans* | 2608 | − | − | − | − |
| Normal stool | | − | − | − | − |
| Human T-cells | | − | − | − | − |
| *Candida albicans* | | − | − | − | − |
| *Crytococcus neoformans* | | − | − | − | − |
| Wheat germ | | − | − | − | − |

| Genus Species | Strain GT # | PROBE BEHAVIOUR | | |
|---|---|---|---|---|
| | | 2383 | 2390 | 2393 |
| *Citrobacter freundii* | 0687 | + | − | − |
| *Escherichia coli* | 1665 | + | − | − |
| *Haemophilus influenza* | 33391 | ++ | − | − |
| *Klebsiella pneumoniae* | 1500 | +++ | − | − |

TABLE 4d-continued

DOT BLOT HYBRIDIZATION OF 23S rRNA-TARGETED MYCOBACTERIUM KANSASII PROBES

| | | | | |
|---|---|---|---|---|
| *Bordetella pertussis* | 3513 | – | – | – |
| *Agrobacterium tumefaciens* | 2021 | – | – | – |
| *Desulfovibrio desulfuricans* | ATCC7757 | – | – | – |
| *Campylobacter jejuni* | 0022 | – | – | – |
| *Bacillus subtilis* | 0804 | – | – | – |
| *Clostridium perfringens* | ATCC13124 | – | – | – |
| *Mycoplasma pneumonia* | FH | – | – | – |
| *Staphylococcus aureus* | 1711 | – | – | – |
| *Streptococcus faecalis* | 0406 | – | – | – |
| *Streptococcus pneumonia* | 0408 | – | – | – |
| *Streptococcus salivarius* | 0410 | – | – | – |
| *Actinomyces israelii* | 0005 | – | – | – |
| *Actinomyces odontolyticulus* | 2195 | +++ | – | – |
| *Arthrobacter globifiormis* | 2117 | – | – | – |
| *Bifidobacterium dentium* | 0012 | – | – | – |
| *Corynebacterium genitalium* | 0045 | – | – | – |
| *Corynebacterium glutamicum* | 2120 | ++++ | – | – |
| *Corynebacterium pseudodiphtheriticum* | 2119 | – | – | – |
| *Corynebacterium pseudotuberculosis* | 2122 | – | – | – |
| *Corynebacterium pyogenes* | 2121 | +++ | – | + |
| *Corynebacterium xerosis* | 0046 | +++ | – | +++ |
| *Corynebacterium diphtheriae* | 3511 | +++ | – | – |
| *Corynebacterium diphtheriae* | 3512 | +++ | – | – |
| *Jonesia denitrificans* | 0666 | – | – | – |
| *Micrococcus conoglomeratus* | ATCC0401 | – | – | – |
| *Micrococcus luteus* | ATCC0381 | – | – | – |
| Mycobacterium species | 0298 | – | – | – |
| *Nocardia asteroides* | 2192 | – | – | – |
| *Nocardia albus* | DSM43109 | – | – | – |
| *Nocardia dassonvillei* | DMS43235 | – | – | – |
| Pimelobacter simplex | DMS08929 | ++++ | – | +++ |
| *Propionobacterium acnes* | 0363 | ++++ | – | – |
| *Propionobacterium thoenii* | DMS20276 | – | – | – |
| *Rhodococcus equi* | 0665 | – | – | – |
| *Rhodococcus rhodochrous* | | – | – | – |
| *Rhodococcus bronchialis* | 3473 | – | – | – |
| *Rhodococcus sputi* | 3474 | – | – | – |
| *Rhodococcus obuensis* | 3475 | – | – | – |
| *Rhodococcus aurantiacus* | 3476 | – | – | – |
| *Rhodococcus erythopolis* | 3523 | – | – | – |
| *Rhodococcus fascians* | 3524 | – | – | – |
| *Rhodococcus rhodochrous* | 3589 | – | – | – |
| *Rhodococcus ketoglutanicum* | 3588 | – | – | – |
| *Streptomyces griseus* | 3590 | – | – | – |
| *Streptomyces mutans* | 0412 | – | – | – |
| *Streptomyces mitis* | 3490 | – | – | – |
| *Bifidobacterium dentium* | 0571 | – | – | – |
| *K rhinoscleromitis* | 1881 | +++ | – | – |
| *Fusobacterium necrophorum* | 0238 | – | – | – |
| *Spirochaeta aurantia* | | – | – | – |
| *Bacteroides fragilis* | ATCC29771 | – | – | – |
| *Chlorobium limicola* | | – | – | – |
| *Chloroflexus aurantiacus* | Y0400 | – | – | – |
| *Deinococcus radiodurans* | 2608 | – | – | – |
| Normal stool | | – | – | – |
| Human T-cells | | – | – | – |
| *Candida albicans* | | – | – | – |
| *Crytococcus neoformans* | | – | – | – |
| Wheat germ | | – | – | – |

*Inclusivity data was determined after four hour exposure and exclusivity data was determined after overnight exposure.
**Each organism is represented by either 100 ng of CsTFA purified RNA.
***+++ = positive level of hybridization; + = barely detectable and – = zero.

TABLE 4e

DOT BLOT HYBRIDIZATION OF 23S rRNA-TARGETED MYCOBACTERIUM FORTUITUM PROBES

| | | PROBE BEHAVIOUR | | | | |
|---|---|---|---|---|---|---|
| Genus Species | Strain GT # | 2373 | 2380 | 2376 | 2379 | 2365 |
| *Citrobacter freundii* | 0687 | – | – | – | – | – |

TABLE 4e-continued

DOT BLOT HYBRIDIZATION OF 23S
rRNA-TARGETED MYCOBACTERIUM FORTUITUM PROBES

| Escherichia coli | 1665 | – | – | – | – | – |
| --- | --- | --- | --- | --- | --- | --- |
| Haemophilus influenza | 33391 | – | – | – | – | – |
| Klebsiella pneumoniae | 1500 | – | – | – | – | – |
| Bordetella pertussis | 3513 | – | – | – | – | – |
| Agrobacterium tumefaciens | 2021 | – | – | – | – | – |
| Desulfovibrio desulfuricans | ATCC7757 | – | – | – | – | – |
| Campylobacter jejuni | 0022 | – | – | – | – | – |
| Bacillus subtilis | 0804 | – | – | – | – | – |
| Clostridium perfringens | ATCC13124 | – | – | – | – | – |
| Mycoplasma pneumonia | FH | – | – | – | – | – |
| Staphylococcus aureus | 1711 | – | – | – | – | – |
| Streptococcus faecalis | 0406 | – | – | – | – | – |
| Streptococcus pneumonia | 0408 | – | – | – | – | – |
| Streptococcus salivarius | 0410 | – | – | – | – | – |
| Actinomyces israelii | 0005 | – | – | – | – | – |
| Actinomyces odontolyticulus | 2195 | – | – | + | – | + |
| Arthrobacter globiformis | 2117 | – | – | – | – | – |
| Bifidobacterium dentium | 0012 | – | – | – | – | + |
| Corynebacterium genitalium | 0045 | – | – | – | – | + |
| Corynebacterium glutamicum | 2120 | – | – | – | – | + |
| Corynebacterium pseudodiphtheriticum | 2119 | – | – | – | – | – |
| Corynebacterium pseudotuberculosis | 2122 | – | – | – | – | – |
| Corynebacterium pyogenes | 2121 | – | – | – | – | – |
| Corynebacterium xerosis | 0046 | – | – | – | – | – |
| Corynebacterium diphtheriae | 3511 | ++++ | – | – | – | + |
| Corynebacterium diphtheriae | 3512 | ++++ | – | – | – | + |
| Jonesia denitrificans | 0666 | – | – | – | – | – |
| Micrococcus conoglomeratus | ATCC0401 | – | – | – | – | + |
| Micrococcus luteus | ATCC0381 | – | – | – | – | +++ |
| Mycobacterium species | 0298 | – | – | – | – | +++ |
| Nocardia asteroides | 2192 | – | – | – | – | – |
| Nocardia albus | DSM43109 | – | – | – | – | + |
| Nocardia dassonvillei | DMS43235 | – | – | – | – | + |
| Pimelobacter simplex | DMS08929 | – | – | – | – | + |
| Propionobacterium acnes | 0363 | – | – | – | – | ++ |
| Propionobacterium thoenii | DMS20276 | – | – | – | – | – |
| Rhodococcus equi | 0665 | – | – | – | – | +++ |
| Rhodococcus rhodochrous |  | – | – | – | – | – |
| Rhodococcus bronchialis | 3473 | – | – | – | – | ++ |
| Rhodococcus sputi | 3474 | – | – | – | – | – |
| Rhodococcus obuensis | 3475 | – | – | – | – | – |
| Rhodococcus aurantiacus | 3476 | – | – | – | – | +++ |
| Rhodococcus erythopolis | 3523 | – | – | – | – | + |
| Rhodococcus fascians | 3524 | – | – | – | – | ++ |
| Rhodococcus rhodochrous | 3589 | – | – | – | – | + |
| Rhodococcus ketoglutanicum | 3588 | – | – | – | – | + |
| Streptomyces griseus | 3590 | – | – | – | – | + |
| Streptomyces mutans | 0412 | – | – | – | – | – |
| Streptomyces mitis | 3490 | – | – | – | – | – |
| Bifidobacterium dentium | 0571 | – | – | – | – | – |
| K rhinoscleromitis | 1881 | – | – | – | – | – |
| Fusobacterium necrophorum | 0238 | – | – | – | – | – |
| Spirochaeta aurantia |  | – | – | – | – | – |
| Bacteroides fragilis | ATCC29771 | – | – | – | – | – |
| Chlorobium limicola |  | – | – | – | – | – |
| Chloroflexus aurantiacus | Y0400 | – | – | – | – | – |
| Deinococcus radiodurans | 2608 | – | – | – | – | – |
| Normal stool |  | – | – | – | – | – |
| Human T-cells |  | – | – | – | – | – |
| Candida albicans |  | – | – | – | – | – |
| Crytococcus neoformans |  | – | – | – | – | – |
| Wheat germ |  | – | – | – | – | – |

| | | PROBE BEHAVIOUR | | | |
| --- | --- | --- | --- | --- | --- |
| Genus Species | Strain | 2375 | 2378 | 2377 | 2374 |
| Citrobacter freundii | 0687 | – | + | – | – |
| Escherichia coli | 1665 | – | + | – | – |
| Haemophilus influenza | 33391 | – | – | – | – |
| Klebsiella pneumoniae | 1500 | – | + | – | – |
| Bordetella pertussis | 3513 | – | – | – | – |
| Agrobacterium tumefaciens | 2021 | – | – | – | – |
| Desulfovibrio desulfuricans | ATCC7757 | – | – | – | – |
| Campylobacter jejuni | 0022 | – | – | – | – |
| Bacillus subtilis | 0804 | – | – | – | – |

TABLE 4e-continued

DOT BLOT HYBRIDIZATION OF 23S
rRNA-TARGETED MYCOBACTERIUM FORTUITUM PROBES

| | | | | | |
|---|---|---|---|---|---|
| *Clostridium perfringens* | ATCC13124 | − | − | − | − |
| *Mycoplasma pneumonia* | FH | − | − | − | − |
| *Staphylococcus aureus* | 1711 | − | − | − | − |
| *Streptococcus faecalis* | 0406 | − | − | − | − |
| *Streptococcus pneumonia* | 0408 | − | − | − | − |
| *Streptococcus salivarius* | 0410 | − | − | − | − |
| *Actinomyces israelii* | 0005 | − | − | − | − |
| *Actinomyces odontolyticulus* | 2195 | − | − | − | + |
| *Arthrobacter globiformis* | 2117 | − | − | − | − |
| *Bifidobacterium dentium* | 0012 | − | − | − | − |
| *Corynebacterium genitalium* | 0045 | − | − | − | +++ |
| *Corynebacterium glutamicum* | 2120 | − | + | − | − |
| *Corynebacterium pseudodiphtheriticum* | 2119 | − | − | − | − |
| *Corynebacterium pseudotuberculosis* | 2122 | − | − | − | − |
| *Corynebacterium pyogenes* | 2121 | − | + | − | ++ |
| *Corynebacterium xerosis* | 0046 | − | + | − | − |
| *Corynebacterium diphtheriae* | 3511 | − | + | − | + |
| *Corynebacterium diphtheriae* | 3512 | − | + | − | + |
| *Jonesia denitrificans* | 0666 | − | − | − | − |
| *Micrococcus conoglomeratus* | ATCC0401 | − | − | − | − |
| *Micrococcus luteus* | ATCC0381 | + | − | − | ++ |
| *Mycobacterium species* | 0298 | ++ | − | − | ++ |
| *Nocardia asteroides* | 2192 | − | − | − | − |
| *Nocardia albus* | DSM43109 | − | − | − | ++ |
| *Nocardia dassonvillei* | DMS43235 | − | − | − | − |
| *Pimelobacter simplex* | DMS08929 | − | + | − | − |
| *Propionobacterium acnes* | 0363 | − | + | − | − |
| *Propionobacterium thoenii* | DMS20276 | − | − | − | +++ |
| *Rhodococcus equi* | 0665 | − | − | − | +++ |
| *Rhodococcus rhodochrous* | | − | − | − | + |
| *Rhodococcus bronchialis* | 3473 | + | − | − | + |
| *Rhodococcus sputi* | 3474 | − | − | − | + |
| *Rhodococcus obuensis* | 3475 | − | − | − | − |
| *Rhodococcus aurantiacus* | 3476 | ++ | − | − | ++ |
| *Rhodococcus erythopolis* | 3523 | − | − | − | − |
| *Rhodococcus fascians* | 3524 | + | − | − | − |
| *Rhodococcus rhodochrous* | 3589 | − | − | − | ++ |
| *Rhodococcus ketoglutanicum* | 3588 | − | − | − | − |
| *Streptomyces griseus* | 3590 | − | − | − | − |
| *Streptomyces mutans* | 0412 | − | − | − | − |
| *Streptomyces mitis* | 3490 | − | − | − | − |
| *Bifidobacterium dentium* | 0571 | − | − | − | − |
| *K rhinoscleromitis* | 1881 | − | − | + | − |
| *Fusobacterium necrophorum* | 0238 | − | − | − | − |
| *Spirochaeta aurantia* | | − | − | − | − |
| *Bacteroides fragilis* | ATCC29771 | − | − | − | − |
| *Chlorobium limicola* | | − | − | − | − |
| *Chloroflexus aurantiacus* | Y0400 | − | − | − | − |
| *Deinococcus radiodurans* | 2608 | − | − | − | − |
| Normal stool | | − | − | − | − |
| Human T-cells | | − | − | − | − |
| *Candida albicans* | | − | − | − | − |
| *Crytococcus neoformans* | | − | − | − | − |
| Wheat germ | | − | − | − | − |

*Inclusivity data was determined after four hour exposure and exclusivity data was determined after overnight exposure.
**Each organism is represented by either 100 ng of CsTFA purified RNA.
***++++ = positive level of hybridization; + = barely detectable and − = zero.

We claim:

1. A partially inclusive nucleic acid selected from the group consisting of:
a) SEQ ID NO: 48;
b) SEQ ID NO: 51;
c) SEQ ID NO: 53;
d) SEQ ID NO: 67;
e) SEQ ID NO: 69;
f) SEQ ID NO: 72;
g) SEQ ID NO: 79;
h) SEQ ID NO: 77;
i) SEQ ID NO: 92;
j) SEQ ID NO: 116;
k) SEQ ID NO: 101;
l) SEQ ID NO: 103;
m) SEQ ID NO: 105;
n) SEQ ID NO: 112;
o) SEQ ID NO: 89;
p) SEQ ID NO: 56;
q) SEQ ID NO: 61;
r) oligonucleotides of a) through q) wherein U is substituted for T; and
s) full complements of a) through r).

2. A substantially inclusive oligonucleotide, selected from the group consisting of:
a) SEQ ID NO: 72;
b) oligonucleotides of a) wherein U is substituted for T; and
c) full complements of a) through c).

3. An oligonucleotide set having two or more oligonucleotides selected from the group consisting of:
a) SEQ ID NO: 48;
b) SEQ ID NO: 51;
c) SEQ ID NO: 53;
d) SEQ ID NO: 67;
e) SEQ ID NO: 69;
f) SEQ ID NO: 72;
g) SEQ ID NO: 79;
h) SEQ ID NO: 77;
i) SEQ ID NO: 92;
j) SEQ ID NO: 116;
k) SEQ ID NO: 101;
l) SEQ ID NO: 103;
m) SEQ ID NO: 105;
n) SEQ ID NO: 112;
o) SEQ ID NO: 89;
p) SEQ ID NO: 56;
q) SEQ ID NO: 61;
r) oligonucleotides of a) through q) wherein U is substituted for T; and
s) complements of a) through r).

4. A capture/detection oligonucleotide set, the capture oligonucleotide selected from the group of oligonucleotides consisting of:
a) SEQ ID NO: 48;
b) SEQ ID NO: 51;
c) SEQ ID NO: 53;
d) SEQ ID NO: 67;
e) SEQ ID NO: 69;
f) SEQ ID NO: 72;
g) SEQ ID NO: 79;
h) SEQ ID NO: 77;
i) SEQ ID NO: 92;
j) SEQ ID NO: 116;
k) SEQ ID NO: 101;
l) SEQ ID NO: 103;
m) SEQ ID NO: 105;
n) SEQ ID NO: 112;
o) SEQ ID NO: 89;
p) SEQ ID NO: 56;
q) SEQ ID NO: 61;
r) oligonucleotides of a) through q) wherein U is substituted for T; and
s) complements of a) through r);
and the detection oligonucleotide selected from the group consisting of:
a) Sequence ID Number 110;
b) Sequence ID Number 98;
c) Sequence ID Number 94;
d) Sequence ID Number 96;
e) Sequence ID Number 114;
f) Sequence ID Number 84;
g) Sequence ID Number 59;
h) Sequence ID Number 53; and
i) Sequence ID Number 67.

5. A kit for the identification of bacteria of the genus Mycobacteria, the kit comprising a hybridization reaction container, hybridization buffer, wash buffer and two or more oligonucleotides selected from the group consisting of:
a) SEQ ID NO: 48;
b) SEQ ID NO: 51;
c) SEQ ID NO: 53;
d) SEQ ID NO: 67;
e) SEQ ID NO: 69;
f) SEQ ID NO: 72;
g) SEQ ID NO: 79;
h) SEQ ID NO: 77;
i) SEQ ID NO: 92;
j) SEQ ID NO: 116;
k) SEQ ID NO: 101;
l) SEQ ID NO: 103;
m) SEQ ID NO: 105;
n) SEQ ID NO: 112;
o) SEQ ID NO: 89;
p) SEQ ID NO: 56;
q) SEQ ID NO: 61;
r) oligonucleotides of a) through q) wherein U is substituted for T; and
s) complements of a) through r).

6. A kit for the identification of bacteria of the genus Mycobacteria, the kit comprising a hybridization reaction container, hybridization buffer, wash buffer and a capture/detection oligonucleotide set wherein the capture oligonucleotide is selected from the group consisting of:
a) SEQ ID NO: 48;
b) SEQ ID NO: 51;
c) SEQ ID NO: 53;
d) SEQ ID NO: 67;

e) SEQ ID NO: 69;
f) SEQ ID NO: 72;
g) SEQ ID NO: 79;
h) SEQ ID NO: 77;
i) SEQ ID NO: 92;
j) SEQ ID NO: 116;
k) SEQ ID NO: 101;
l) SEQ ID NO: 103;
m) SEQ ID NO: 105;
n) SEQ ID NO: 112;
o) SEQ ID NO: 89;
p) SEQ ID NO: 56;
q) SEQ ID NO: 61;
r) oligonucleotides of a) through q) wherein U is substituted for T; and
s) complements of a) through r);

and the detection oligonucleotide selected from the group consisting of:
a) Sequence ID Number 110;
b) Sequence ID Number 98;
c) Sequence ID Number 94;
d) Sequence ID Number 96;
e) Sequence ID Number 114;
f) Sequence ID Number 84;
g) Sequence ID Number 59;
h) Sequence ID Number 53; and
i) Sequence ID Number 67.

* * * * *